US008859555B2

(12) United States Patent
Ortega Muñoz et al.

(10) Patent No.: US 8,859,555 B2
(45) Date of Patent: *Oct. 14, 2014

(54) LYSINE SPECIFIC DEMETHYLASE-1 INHIBITORS AND THEIR USE

(75) Inventors: Alberto Ortega Muñoz, Barcelona (ES); Julio Castro-Palomino Laria, Barcelona (ES); Matthew Colin Thor Fyfe, Barcelona (ES)

(73) Assignee: Oryzon Genomics S.A., Barcelona (ES)

( * ) Notice: Subject to any disclaimer, the term of this patent is extended or adjusted under 35 U.S.C. 154(b) by 0 days.

This patent is subject to a terminal disclaimer.

(21) Appl. No.: 13/497,994

(22) PCT Filed: Apr. 19, 2010

(86) PCT No.: PCT/EP2010/055131
§ 371 (c)(1),
(2), (4) Date: Jul. 27, 2012

(87) PCT Pub. No.: WO2011/035941
PCT Pub. Date: Mar. 31, 2011

(65) Prior Publication Data
US 2012/0283266 A1   Nov. 8, 2012

(30) Foreign Application Priority Data

Sep. 25, 2009  (EP) .................................... 09171425
Jan. 15, 2010  (EP) .................................... 10150866

(51) Int. Cl.
| | | |
|---|---|---|
| A61K 31/495 | (2006.01) | |
| C07D 295/13 | (2006.01) | |
| A61K 31/075 | (2006.01) | |
| C07C 211/40 | (2006.01) | |
| C07D 211/14 | (2006.01) | |
| C07D 241/04 | (2006.01) | |
| A61K 45/06 | (2006.01) | |
| C07C 323/25 | (2006.01) | |
| C07C 217/74 | (2006.01) | |
| C07D 207/14 | (2006.01) | |
| A61K 31/40 | (2006.01) | |
| C07C 217/08 | (2006.01) | |
| A61K 31/095 | (2006.01) | |

(52) U.S. Cl.
CPC ............ *C07D 241/04* (2013.01); *A61K 31/075* (2013.01); *C07C 2101/02* (2013.01); *C07C 211/40* (2013.01); *C07D 211/14* (2013.01); *A61K 45/06* (2013.01); *C07C 323/25* (2013.01); *C07C 217/74* (2013.01); *A61K 31/495* (2013.01); *C07D 207/14* (2013.01); *A61K 31/40* (2013.01); *C07C 217/08* (2013.01); *A61K 31/095* (2013.01)
USPC ..................................... 514/252.12; 544/402

(58) Field of Classification Search
USPC ........................................................ 544/402
See application file for complete search history.

(56) References Cited

U.S. PATENT DOCUMENTS

| 3,106,578 A | 10/1963 | Kaiser et al. |
| 3,365,458 A | 1/1968 | Biel et al. |
| 3,471,522 A | 10/1969 | Biel et al. |
| 3,532,712 A | 10/1970 | Biel et al. |

(Continued)

FOREIGN PATENT DOCUMENTS

| EP | 1193268 | 4/2002 |
| EP | 1704859 | 9/2006 |

(Continued)

OTHER PUBLICATIONS

Wermuth, Camille G. Molecular Variations Based on Isosteric Replacements, The Practice of Medicinal Chemistry (Second Edition), Academic Press, London, 2003, pp. 189-214.*

(Continued)

*Primary Examiner* — Golam M M Shameem
*Assistant Examiner* — Laura Daniel
(74) *Attorney, Agent, or Firm* — Finnegan, Henderson, Farabow, Garrett & Dunner, LLP

(57) ABSTRACT

The invention relates to a compound of Formula (I): $(A')_x$-(A)-(B)-(Z)-(L)-(D), wherein: (A) is heteroaryl or aryl; each (A'), if present, is independently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, 2, or 3 substituents independently chosen from halo, haloalkyl, aryl, arylalkoxy, alkyl, alkoxy, cyano, sulfonyl, amido, and sulfinyl; X is 0, 1, 2, or 3; (B) is a cyclopropyl ring, wherein (A) and (Z) are covalently bonded to different carbon atoms of (B); (Z) is —NH—; (L) is chosen from —$CH_2CH_2$—, —$CH_2CH_2CH_2$—, and —$CH_2CH_2CH_2CH_2$—; and (D) is chosen from —N(—R1)-R2, —O—R3, and —S—R3, wherein: R1 and R2 are mutually linked to form a heterocyclic ring together with the nitrogen atom that R1 and R2 are attached to, wherein said heterocyclic ring has 0, 1, 2, or 3 substituents independently chosen from —$NH_2$, —NH($C_1$-$C_6$ alkyl), —N($C_1$-$C_6$ alkyl)($C_1$-$C_6$ alkyl), alkyl, halo, cyano, alkoxy, haloalkyl, and haloalkoxy, or R1 and R2 are independently chosen from —H, alkyl, cycloalkyl, haloalkyl, and heterocyclyl, wherein the sum of substituents on R1 and R2 together is 0, 1, 2, or 3, and the substituents are independently chosen from —$NH_2$, —NH($C_1$-$C_6$ alkyl), —N($C_1$-$C_6$ alkyl)($C_1$-$C_6$ alkyl), and fluoro; and R3 is chosen from —H, alkyl, cycloalkyl, haloalkyl, and heterocyclyl, wherein R3 has 0, 1, 2, or 3 substituents independently chosen from —$NH_2$, —NH($C_1$-$C_6$ alkyl), —N($C_1$-$C_6$ alkyl)($C_1$-$C_6$ alkyl), and fluoro; or an enantiomer, diastereomer, or mixture thereof, or a pharmaceutically acceptable salt or solvate thereof. The compounds of the invention show inhibitory LSD1 activity, which makes them useful in the treatment or prevention of diseases such as cancer.

23 Claims, 7 Drawing Sheets

(56) References Cited

U.S. PATENT DOCUMENTS

| | | |
|---|---|---|
| 3,532,749 A | 10/1970 | Biel et al. |
| 3,758,684 A | 9/1973 | Elion et al. |
| 4,409,243 A | 10/1983 | Lieb |
| 4,522,811 A | 6/1985 | Eppstein et al. |
| 4,530,901 A | 7/1985 | Weissmann |
| 6,043,393 A | 3/2000 | de Meijere et al. |
| 6,211,244 B1 | 4/2001 | Van Wagenen et al. |
| 6,337,074 B1 | 1/2002 | Marsden et al. |
| 6,809,120 B1 | 10/2004 | Warrington et al. |
| 7,399,825 B2 | 7/2008 | Lipps et al. |
| 7,611,704 B2 | 11/2009 | Thorpe et al. |
| 7,628,993 B2 | 12/2009 | Vilalta et al. |
| 7,799,782 B2 | 9/2010 | Munson et al. |
| 8,524,717 B2 | 9/2013 | Guibourt et al. |
| 2003/0008844 A1 | 1/2003 | Spero et al. |
| 2003/0236225 A1 | 12/2003 | Protopopova et al. |
| 2004/0019117 A1 | 1/2004 | Protopopova et al. |
| 2004/0033986 A1 | 2/2004 | Protopopova et al. |
| 2004/0048802 A1 | 3/2004 | Ripka et al. |
| 2004/0132820 A1 | 7/2004 | Gosselin et al. |
| 2004/0147741 A1 | 7/2004 | Sundermann et al. |
| 2004/0162287 A1 | 8/2004 | Sundermann et al. |
| 2004/0176469 A1 | 9/2004 | Thomas |
| 2004/0229872 A1 | 11/2004 | Friderichs et al. |
| 2004/0254158 A1 | 12/2004 | Qiao et al. |
| 2005/0009832 A1 | 1/2005 | Sun et al. |
| 2005/0154056 A1 | 7/2005 | Yang et al. |
| 2006/0116370 A1 | 6/2006 | Dollinger et al. |
| 2006/0148904 A1 | 7/2006 | Protopopova et al. |
| 2006/0211709 A1 | 9/2006 | Buhr et al. |
| 2006/0270673 A1 | 11/2006 | Duggan et al. |
| 2006/0275366 A1 | 12/2006 | Malcolm et al. |
| 2006/0287287 A1 | 12/2006 | Gerritz et al. |
| 2007/0213338 A1 | 9/2007 | Lebsack et al. |
| 2008/0139665 A1 | 6/2008 | Schuele et al. |
| 2008/0242698 A1* | 10/2008 | Flor et al. ................ 514/307 |
| 2008/0269228 A1 | 10/2008 | Moore et al. |
| 2009/0203750 A1 | 8/2009 | Kozikowski et al. |
| 2009/0247530 A1 | 10/2009 | Nolte et al. |
| 2010/0016262 A1 | 1/2010 | Mehal et al. |
| 2010/0240649 A1 | 9/2010 | Zhang |
| 2010/0292225 A1 | 11/2010 | Chamoin et al. |
| 2010/0324147 A1 | 12/2010 | McCafferty et al. |
| 2011/0263604 A1 | 10/2011 | Guibourt et al. |
| 2012/0004262 A1 | 1/2012 | Guibourt et al. |
| 2012/0202810 A1 | 8/2012 | Nolte et al. |
| 2012/0264823 A1 | 10/2012 | Ortega Munoz et al. |
| 2013/0090386 A1 | 4/2013 | Ortega Munoz et al. |
| 2013/0095067 A1 | 4/2013 | Baker et al. |
| 2013/0197013 A1 | 8/2013 | Fyfe et al. |
| 2013/0197095 A1 | 8/2013 | Nolte et al. |
| 2013/0231342 A1 | 9/2013 | Munoz et al. |
| 2013/0274267 A1 | 10/2013 | Cesar Castro Palomino Laria et al. |
| 2013/0289076 A1 | 10/2013 | Laria et al. |
| 2013/0303545 A1 | 11/2013 | Maes et al. |

FOREIGN PATENT DOCUMENTS

| | | |
|---|---|---|
| EP | 1741708 | 1/2007 |
| EP | 2233495 | 9/2010 |
| GB | 1307341 | 2/1973 |
| JP | 2001354563 | 12/2001 |
| SU | 230169 | 10/1968 |
| WO | WO94/27947 | 12/1994 |
| WO | WO96/38141 | 12/1996 |
| WO | WO98/18459 | 5/1998 |
| WO | WO99/05142 | 2/1999 |
| WO | WO99/05143 | 2/1999 |
| WO | WO99/31072 | 6/1999 |
| WO | WO99/54440 | 10/1999 |
| WO | WO99/67203 | 12/1999 |
| WO | WO00/34283 | 6/2000 |
| WO | WO01/92264 | 12/2001 |
| WO | WO02/079152 | 10/2002 |
| WO | WO03/087064 | 10/2003 |
| WO | WO03/093297 | 11/2003 |
| WO | WO03/096989 | 11/2003 |
| WO | WO2004/020415 | 3/2004 |
| WO | WO2004/055010 A2 | 7/2004 |
| WO | WO2004/062601 | 7/2004 |
| WO | WO2004/065367 | 8/2004 |
| WO | WO2004/072086 | 8/2004 |
| WO | WO2005/009941 | 2/2005 |
| WO | WO2005/023761 | 3/2005 |
| WO | WO2005/025558 A1 | 3/2005 |
| WO | WO2005/037843 | 4/2005 |
| WO | WO2005/058808 | 6/2005 |
| WO | WO2005/058883 | 6/2005 |
| WO | WO2005/058884 | 6/2005 |
| WO | WO2005/103003 | 11/2005 |
| WO | WO2006/071608 | 7/2006 |
| WO | WO2006/087206 | 8/2006 |
| WO | WO2007/000248 | 1/2007 |
| WO | WO 2007/005896 A2 | 1/2007 |
| WO | WO2007/015824 | 2/2007 |
| WO | WO2007/025144 | 3/2007 |
| WO | WO2007/025709 | 3/2007 |
| WO | WO2007/021839 | 7/2007 |
| WO | WO2007/106016 | 9/2007 |
| WO | WO2007/134799 | 11/2007 |
| WO | WO2008/033466 | 3/2008 |
| WO | WO2008/116156 | 9/2008 |
| WO | WO2008/127734 | 10/2008 |
| WO | WO2009/001132 | 12/2008 |
| WO | WO2009/023179 | 2/2009 |
| WO | WO2009/039134 | 3/2009 |
| WO | WO2009/052078 | 4/2009 |
| WO | WO2009/097278 | 8/2009 |
| WO | WO2009/109991 | 9/2009 |
| WO | WO2009/117515 | 9/2009 |
| WO | WO2009/145856 | 12/2009 |
| WO | WO2009/153197 | 12/2009 |
| WO | WO2010/011845 | 1/2010 |
| WO | WO2010/014921 | 2/2010 |
| WO | WO2010/030592 | 3/2010 |
| WO | WO2010/043721 | 4/2010 |
| WO | WO2010/084160 | 7/2010 |
| WO | WO2010/085749 | 7/2010 |
| WO | WO2010/099527 | 9/2010 |
| WO | WO2010/139784 | 12/2010 |
| WO | WO2010/143582 | 12/2010 |
| WO | WO2011/022489 | 2/2011 |
| WO | WO2011/031934 | 3/2011 |
| WO | WO2011/035941 | 3/2011 |
| WO | WO2011/042217 | 4/2011 |
| WO | WO2011/057262 | 5/2011 |
| WO | WO2011/106105 | 9/2011 |
| WO | WO2011/106106 | 9/2011 |
| WO | WO2011/113005 | 9/2011 |
| WO | WO2011/131576 | 10/2011 |
| WO | WO2011/131697 | 10/2011 |
| WO | WO2011/132083 | 10/2011 |
| WO | WO2012/001531 | 1/2012 |
| WO | WO2012/013727 | 2/2012 |
| WO | WO2012/013728 | 2/2012 |
| WO | WO2012/034116 | 3/2012 |
| WO | WO2012/042042 | 4/2012 |
| WO | WO2012/045883 | 4/2012 |
| WO | WO2012/072713 | 6/2012 |
| WO | WO2012/107498 | 8/2012 |
| WO | WO2012/107499 | 8/2012 |
| WO | WO2012/135113 | 10/2012 |
| WO | WO2012/156531 | 11/2012 |
| WO | WO2012/156537 | 11/2012 |
| WO | WO2013/057320 | 4/2013 |
| WO | WO2013/057322 | 4/2013 |

OTHER PUBLICATIONS

Vagner, Josef. Current Opinion on Chemical Biology 2008, 12: 292-296.*

(56) References Cited

OTHER PUBLICATIONS

The International Search Report received in the corresponding International Patent Application No. PCT/EP2010/055131, dated Oct. 26, 2010.
Gooden, et al., "Facile synthesis of substituted trans-2-arylcyclopropylamine inhibitors of the human histone demethylase LSD1 and monoamine oxidases A and B", Bioorganic & Medicinal Chemistry Letters, vol. 18, 2008, pp. 3047-3051.
Kaiser, et al., "2-Substituted Cyclopropylamines. I. Derivatives and Analogs of 2-Phenycyclopropylamine", Journal of Medicinal and Pharmaceutical Chemistry, American Chemical Society, vol. 5, 1962, pp. 1243-1265.
Zirkle, et al., "2-Substituted Cyclophopylamines. II. Effect of Structure upon Monoamine Oxidase-Inhibitory Activity as Measured in Vivo Potentiation of Tryptamine Convulsions" Journal of Medicinal and Pharmaceutical Chemistry, American Chemical Society, vol. 5, 1962, pp. 1265-1284.
Ahmed et al, "Ticagrelor: a new reversible oral antiplatelet agent" Int Research Journal of Pharmacy, 2010, 1(1), 62-69.
Arya et al, "Synthesis of 5H-dibenzo[a,d]cycloheptene derivatives with diverse biological activities", Indian J Chemistry B, 1978, 16B,220-225.
Bar-Am et al, "Regulation of Bcl-2 family proteins, neurotrophic factors, and APP processing in the neurorescue activity of propargylamine". FASEB J, 2005, 19(13),1899-1901.
Barlesi et al, "Global histone modifications predict prognosis of resected non small-cell lung cancer",J Clin Oncol,2007,25, 4358-4364.
Benelkebir et al, "Enantioselective synthesis of tranylcypromine analogues as lysine demethylase (LSD1) inhibitors", Bioorg Med Chem, 2011,19(12),3709-3716.
Biljak et al,"Platelet count, mean platelet volume and smoking status in stable chronic obstructive pulmonary disease", Platelets, 2011,22(6), 466-70.
Binda et al, "Biochemical, structural, and biological evaluation of tranylcypromine derivatives as inhibitors of histone demethylases LSD1 and LSD2", J Am Chem Soc,2010,132(19),6827-6833.
Bisi et al, "Multidrug resistance reverting activity and antitumor profile of new phenothiazine derivatives", Bioorg Med Chem, 2008, 16(13), 6474-6482.
Boilard et al, "Platelets amplify inflammation in arthritis via collagen-dependent microparticle production", Science, 2010,327(5965), 580-583.
Bolesov et al, "Cyclopropanes and cyclobutanes LXIX", Zhurnal Organicheskoi Khimii (Eng Tranl), 1974, 10(10), 2122-2128.
Bolesov et al, "Cyclopropanes and cyclobutanes LXVIII. N-mono and N,N-disubstituted 1-amino-2-phenylcyclopropanes", J Organic Chem USSR, 1974, 10(6), Part 01, 1678-84.
Brand and Perrimon, "Targeted gene expression as a means of altering cell fates and generating dominant phenotypes", 1993, Development, 118, 401-415.
Brydon et al, "Platelets, coronary heart disease and stress", Brain, Behavior and Immunity,2006, 20(2), 113-119.
Burakova et al, "N- and O-alkylation of 3-indolylcyclopropylacetic acid derivatives", Russian Chemical Bulletin, 2002, 51(10) 1829-1840.
Burk et al, "Cognitive deficits in spinocerebellar ataxia 2", Brain, 1999,122(4), 769-777.
Cakmak et al, "Platelets: indicator of inflammation in COPD", Int J Med Med Sci, 2009, 1(5), 227-229.
Calogero et al, "Inhibition of cell growth by EGR-1 in human primary cultures from malignant glioma",Cancer Cell International,2004,4, 1.
Casero et al, "Recent advances in the development of polyamine analogues as antitumor agents", J Med Chem, 2009, 52(15),4551-4573.
Chen et al, "Association of insulin resistance and hematologic parameters: study of a middle-aged and elderly chinese population in Taiwan", J Chin Med Assoc,2006, 69(6), 248-253.

Chimenti et al "Synthesis, Stereochemical Identification, and Selective Inhibitory Activity against Human Monoamine Oxidase-B of 2-Methylcyclohexylidene-(4-arylthiazol-2-yl)hydrazones". (2008) J. Med. Chem. 51 (16), 4874-4880.
Choi et al "Histone demethylase LSD1 is required to induce skeletal muscle differentiation by regulating myogenic factors" (2010) Biochemical and Biophysical Research Communications 401(3), 327-332.
Choo et al, "Genetic organization and diversity of the hepatitis C virus", Proc Natl Acad Sci,1991, 88,2451-2455.
Culhane et al, A mechanism-based inactivator for histone demethylase LSD1, J Am Chem Soc, 2006, 128(14), 4536-4537.
Culhane et al, "Comparative analysis of small molecules and histone substrate analogues as LSD1 lysine demethylase inhibitors", J Am Chem Soc, 2010,132(9),3164-3176.
Danese et al, "Platelets in inflammatory bowel disease: clinical, pathogenic and therapeutic implications", Am J Gastroenterol, 2004,99(5), 938-45.
Di Stefano et al, Mutation of Drosophila Lsd1 disrupts H3-K4 methylation, resulting in tissue-specific defects during development, Curr Biol,2007, 17(9), 808-12.
East et al, "An orally bioavailable positive allosteric modulator of the mGlu4 receptor with efficacy in an animal model of motor dysfunction", Bioorg Med Chem Lett, 2010, 20(16), 4901-5.
Ellis et al, "Expression of Drosophila glass protein and evidence for negative regulation of its activity in non-neuronal cells by another DNA-binding protein",Development,1993, 119, 855-865.
Elsheikh et al "Global histone modifications in breast cancer correlate with tumor phenotypes, prognostic factors and patient outcome", Canc Res, 2009,69, 3802-3809.
Erazo et al, "Varicella-zoster virus open reading frame 66 protein kinase is required for efficient viral growth in primary human corneal stromal fibroblast cells", J Virol, 2008,82, 7653-7665.
Faler et al, "The Kulinkovich reaction in the synthesis of constrained N,N-dialkyl neurotransmitter analogues", Organic Letters 2007,9(10),1987-1990.
Ferlay et al, "Estimates of the cancer incidence and mortality in Europe in 2006", Annals of Oncology 2007,18(3), 581-92.
Ferraro et al, "EGR1 predicts PTEN and survival in patients with non-small-cell lung cancer", J Clin Oncol, 2005, 23(9), 1921-26.
Fischer et al, "Recovery of learning and memory is associated with chromatin remodelling", Nature, 2007,447, 178-182.
Forneris et al "LSD1: oxidative chemistry for multifaceted functions in chromatin Regulation." Trends in Biochemical Sciences 2008,33(4), 181-189.
Gawaz et al, "Platelets in inflammation and atherogenesis", J Clin Invest, 2005,115(12), 3378-3384.
Han et al "Modulation of breast cancer resistance protein (BCRP/ABCG2) by non-basic chalcone analogues" Eur. J. Pharma. 2008, 35(1-2) 30-41.
Han et al, "Antidepressants reveal differential effect against 1-methyl-4-phenylpyridinium toxicity in differentiated PC12 cells", Eur J Pharmacol, 2009, 604 (1-3),36-44 (doi:10.1016/j.ejphar.2008. 12.025).
Hayami et al, "Overexpression of LSD1 contributes to human carcinogenesis through chromatin regulation in various cancers", Int J Cancer, 2011, 128(3), 574-86, PMID 20333681.
Hruschka et al, "Fluorinated phenylcyclopropylamines. Part 5:Effect of electron-withdrawing or-donating aryl substituents on the inhibition of monoamine oxidases A and B by 2-aryl-2-fluorocyclopropylamines", Bioorg Med Chem,2008, 16(15), 7148-7166.
Huang et al, "Novel oligoamine analogues inhibit lysine-specific demethylase 1 (LSD1) and induce re-expression of epigeneticall silenced genes",Clin Cancer Res,2009, 15(23), 7217-28.
Huang et al, "p53 is regulated by the lysine demethylase LSD1",Nature,2007,449, 105-108.
Huang et al,"Inhibition of lysine-specific demethylase 1 by polyamine analogues results in reexpression of aberrantly silenced genes", PNAS,2007, 104(19), 8023-8028.
Jackson et al, "Polyglutamine-expanded human Huntingtin transgenes induce degeneration of Drosophila photoreceptor neurons", Neuron, 1998, 21, 633-642.

(56) References Cited

OTHER PUBLICATIONS

Kahl et al, "Androgen receptor coactivators lysine-specific histone demethylase 1 and four and a half LIM domain protein 2 predict risk of prostate cancer recurrence", Cancer Res,2006,66 (23), 11341-11347.
Kiefmann et al, "Red blood cells induce hypoxic lung inflammation", Blood, 2008,111(10),5205-14.
Kornerup et al, "The role of platelets in the pathophysiology of asthma" Platelets, 2007,18(5), 319-28.
Krieger et al, "Enhancement of hepatitis C virus RNA replication by cell culture-adaptive mutations", J Virol, 2001,75, 4614-4624.
Lan et al "Mechanisms involved in the regulation of histone lysine demethylases". Current Opinion in Cell Biology, 2008,20, 316-325.
Lee et al, "Combinatorial lead optimization of [1,2]-diamines based on ethambutol as potential antituberculosis preclinical candidates", J Comb Chem, 2003, 5(2), 172-187.
Lee et al, "Histone H3 lysine 4 demethylation is a target of nonselective antidepressive medications",Chem Biol, 2006,13(6), 563-567.
Li et al, "Association between inflammatory mediators and angiographic morphologic features indicating thrombus formation in patients with acute myocardial infarction", Chin Med J, 2009,122(15), 1738-42.
Liang et al, "Inhibition of the histone demethylase LSD1 blocks alpha-herpesvirus lytic replication and reactivation from latency",Nat Med, 2009,15 (11), 1312-1317.
Lim et al, "Lysine-specific demethylase 1 (LSD1) is highly expressed in ER-negative breast cancers and a biomarker predicting aggressive biology", Carcinogenesis,2010, 31(3), 512-20 epub Dec. 2009, PMID 20042638.
Lucerna et al, "Sustained expression of early growth response protein-1 blocks angiogenesis and tumor growth",Cancer Research,2006, 66,6708-6713.
Lupu Roxana, "Up-to-date in the hematological malignancies treatment", Maedica, 2006,1(1), 63-65.
Maclay et al, "Increased platelet activation in patients with stable and acute exacerbation of COPD", Thorax, 2011,66(9), 769-74.
Mannaioni et al, "Platelets and inflammation: role of platelet-derived growth factor, adhesion molecules and histamine", Inflamm Res, 1997,46(1), 4-18.
McNicol et al, "Beyond hemostasis: the role of platelets in inflammation, malignancy and infection",Cardiovascular & Haematological Disorders-Drug Targets, 2008,8, 99-117.
Meanwell, "Synopsis of some recent tactical application of bioisosteres in drug design", 2011,J Med Chem 54(8),2529-91, PMID 21413808.
Metzger et al, "LSD1 demethylates repressive histone marks to promote androgen-receptor-dependent transcription",Nature,2005, 437(7057),436-9.
Mimasu et al "Crystal structure of histone demethylase LSD1 and tranylcypromine at 2.25 Å" Biochemical and Biophysical Research Communications ,2008,366, 15-22.
Mimasu et al, "Structurally designed trans-2-phenylcyclopropylamine derivatives potently inhibit histone demethylase LSD1/KDM1", Biochemistry,2010,49(30), 6494-6503.
Moritani et al, "Activation of platelets in bronchial asthma", Chest, 1998,113, 452-458.
Neelamegan et al, "Brain-penetrant LSD1 inhibitors can block memory consolidation", ACS Chem Neurosci, 2012, 3(2), 120-128.
Ogasawara et al, "Synthesis and biological activity of optically active NCL-1, a lysine-specific demethylase 1 selective inhibitor",Bioorg Med Chem, 2011, doi:10.1016/j.bmc.2010.12.024.
O'Sullivan et al, "The inflammatory role of platelets in cystic fibrosis", Am J Respir Crit Care Med, 2006,173, 483-90.
Pannala et al "Synthesis and structure—activity relationship of 4-(2-aryl-cyclopropylamino)-quinoline-3-carbonitriles as EGFR tyrosine kinase inhibitors". Bioorg & Med Chem Lett , 2007,17 (21), 5978-5082.
Pitchford et al, "Platelet P-selectin is required for pulmonary eosinophil and lymphocyte recruitment in a murine model of allergic inflammation", Blood, 2005,105, 2074-2081.
Pollock et al, Lysine-specific histone demethylase 1 inhibitors control breast cancer proliferation in ERalpha-dependent and -independent manners, ACS Chem Biol 2012,7,1221-1231.
Ravina et al, "The relationship between CAG repeat length and clinical progression in Huntington's disease", Mov Disord,2008,23(9), 1223-7.
Reddy et al, "Role of lysine-specific demethylase 1 in the proinflammatory phenotype of vascular smooth muscle cells of diabetic mice",Circ Res,2008,103, 615-23.
Riley et al, "Absolute configuration of (+)- and (−)-trans-2-phenylcyclopropylamine hydrochloride",J Med Chem, 1972,15(11), 1187-1188.
Rinder et al, "Correlation of thrombosis with increased platelet turnover in thrombocytosis", Blood, 1998,91(4), 1288-1294.
Schmidt et al,"Trans-2-phenylcyclopropylamine is a mechanism-based inactivator of the histone demethylase LSD1", Biochemistry, 2007,46(14),4408-4416.
Schulte et al, "Lysine-specific demethylase 1 is strongly expressed in poorly differentiated neuroblastoma: implications for therapy", Cancer Res,2009,69(5),2065-71.
Scoumanne et al "Protein methylation: a new mechanism of p53 tumor suppressor regulation" Histol Histopathol 2008,23, 1143-1149.
Scoumanne et al, "The lysine-specific demethylase 1 is required for cell proliferation in both p53-dependent and -independent manners", J Biol Chem, 2007,282(21), 15471-5.
Seligson et al, "Global histone modification patterns predict risk of prostate cancer recurrence",Nature, 2005,435, 1262-1266.
Seligson et al,"Global levels of histone modifications predict prognosis in different cancers" ,Am J Path, 2009,174,1619-28.
Sharma et al, "(Bis)urea and (bis)thiourea inhibitors of lysine-specific demethylase 1 as epigenetic modulators", J Med Chem, 2010,53(14), 5197-5212, PMID 20568780.
Shi et al,"Histone demethylation mediated by the nuclear amine oxidase homolog LSD1", Cell, 2004,119,941-953.
Stephens et al, "The determination of the absolute configurations of chiral molecules using vibrational circular dichroism (VCD) spectroscopy",Chirality, 2008,20(5), 643-663.
Stoffel et al, "Leukocyte count and risk of thrombosis in patients undergoing haematopoietic stem cell transplantation or intensive chemotherapy",Thromb Haemost, 2010,103(6), 1228-32.
Stratmann et al, "Pathobiology and cell interactions of platelets in diabetes", Diab Vasc Dis Res,2005, 2(1), 16-23.
Szewczuk et al, "Mechanistic analysis of a suicide inactivator of histone demethylase LSD1", Biochemistry, 2007,46, 6892-6902.
Tamagawa-Mineoka et al, "Elevated platelet activation in patients with atopic dermatitis and psoriasis: increased plasma levels of beta-thromboglobulin and platelet factor 4", Allergology International,2008, 57, 391-396.
Taylor et al,"Roscovitine, a cyclin-dependent kinase inhibitor, prevents replication of varicella-zoster virus", J Virol, 2004,78, 2853-2862.
Thaulow et al, "Blood platelet count and function are related to total and cardiovascular death in apparently healtht men", Circulation, 1991,84, 613-617.
Ueda et al, "Identification of cell-active lysine specific demethylase 1-selective inhibitors",J Am Chem Soc, 2009,131(48), 17536-17537.
Wagner et al, "Platelets in inflammation and thrombosis", Arteriosclerosis, Thrombosis and Vascular Biology, 2003,23, 2131-2137.
Wang et al "Novel histone demethylase LSD1 inhibitors selectively target cancer cells with pluripotent stem cell properties", Cancer Res, 2011,doi:10.1158/0008-5472.CAN-11-0896.
Wang et al "LSD1 Is a Subunit of the NuRD Complex and Targets the Metastasis Programs in Breast Cancer" Cell 2009, 138, 660-672.
Wang et al, "The lysine demethylase LSD1 (KDM1) is required for maintenance of global DNA methylation", Nature Genetics, 2009,41(1), 125-129.

(56) References Cited

OTHER PUBLICATIONS

Weinreb et al, "Novel neuroprotective mechanism of action of rasagiline is associated with its propargyl moiety: interaction of Bcl-2 family members with PKC pathway", Ann NY Acad Sci, 2005,1053, 348-55.
Wermuth, "Molecular variations based on isosteric replacements", The Practice of Medicinal Chemistry (2nd edition), Academic Press, London, 2003, pp. 189-214.
Westland et al , "N-substituted derivatives of 2-aminoethanethiol and 2-hydraxinoethanethiol", JMedChem 1968, 11(4),824-829.
Whitlow et al,"Recruitment of the transcriptional coactivator HCF-1 to viral immediate-early promoters during initiation of reactivation from latency of herpes simplex virus type 1", J Virol, 2009,83(18):9591-5, epub 0:JV1.01115-09vl.
Willoughby et al, "Platelets and cardiovascular disease",Eur J Cardiovasc Nursing,2002,1, 273-288.
XP002568777 Database chemcats, database accession No. 2088922753, order No. kbsb-0063197, Aurora screening library, Aug. 20, 2009.
Yang et al "Structural Basis for the Inhibition of the LSD1 Histone Demethylase by the Antidepressant trans-2-Phenylcyclopropylamine" Biochemistry 2007,46 (27), 8058-8065.
Yang et al "Structural basis of histone demethylation by LSD1 revealed by suicide inactivation" Nature Structural & Molecular Biology 2007, 14(6), 535-539.
Yoshida et al, "Fluorinated phenylcyclopropylamines. Part 3: inhibition of monoamine oxidase A and B",Bioorg Med Chem,2004,12(10),2645-2652.
M. Nabil Aboul-Enein et al, "Synthesis of some 4-subtituted amino-1-methylpiperidines structurally related to antihistaminics", Pharmaceutica Acta Helvetiae, 1973, 48(3): 151-156.
J. Vagner et al, "Peptidomimetics, a synthetic tool of drug discovery", Current Opinion on Chemical Biology, 2008, 12:292-296.
O. Kinzel et al, "Identification of MK-5710 ((8aS)-8a-methyl-1,3-dioxo-2-[(1S,2R)-2-phenylcyclopropyl]-N-(1-phenyl-1H-pyrazol-5-yl)hexahydro-imidazo[1,5-a]pyrazine-7-(1H)-carboxamide), a potent smoothened antagonist for use in Hedgehog pathway dependent malignancies. Part 2". Bioorg Med Chem Lett 2011, 21(15), 4429-4435.
J Kim et al, "Flavin chemical models for monoamine oxidase inactivation by cyclopropylamines, α-silylamines, and hydrazines", J Am Chem Soc 1995, 117. 100-105.
F. Zaragoza Dorwald, "Side reactions in organic synthesis: A Guide to successful synthesis design", Chapter 1 (Organic synthesis:General remarks), 2005, Wiley-VCH Verlag GmbH & Co KgaA, Weinheim.
Y Shi, "Histone lysine demethylases: emerging roles in development, physiology and disease", Nature Reviews Genetics 2007, 8:829-833.
"Definition of Cancer"—MedicineNetcom Medical references for patients, http://www.medterms.com, 2005.
Johnson et al. CAPLUS, Document No. 157:576967, "Preparation of cyclopropylamines as LSD1 inhibitors in the treatment of cancer", 2012.
Delorme et al, HCAPLUS, Document No. 132:49802, "Preparation of 1-(N-substituted aminomethyl)-4-guanidinomethylcyclohexanes useful in pain management", 1999.
CAS Registry No. RN903487-42-3, entered STN Aug. 23, 2006.
CAS Registry No. RN1251130-23-0, entered STN Nov. 3, 2010.
CAS Registry No. RN1281596-19-7, entered STN Apr. 17, 2011.
CAS Registry No. RN1281615-78-8, entered STN Apr. 17, 2011.
CAS Registry No. RN1282425-35-7, entered STN Apr. 19, 2011.
CAS Registry No. RN220351-33-7, entered STN Mar. 11, 1999.
CAS Registry No. RN844655-03-4, entered STN Mar. 9, 2005.
CAS Registry No. RN846596-02-9, entered STN Mar. 22, 2005.
CAS Registry No. RN848204-13-7, entered STN Apr. 11, 2005.
CAS Registry No. RN848732-87-6, entered STN Apr. 19, 2005.
CAS Registry No. RN848742-47-2, entered STN Apr. 19, 2005.
CAS Registry No. RN848753-47-9, entered STN Apr. 19, 2005.
CAS Registry No. RN918305-55-2, entered STN Jan. 24, 2007.
CAS Registry No. RN959071-98-8, entered STN Dec. 20, 2007.
CAS Registry No. RN1026299-47-7, entered STN Jun. 8, 2008.
CAS Registry No. RN1157140-28-7, entered STN Jun. 14, 2009.
CAS Registry No. RN1218057-33-0, entered STN Apr. 11, 2010.
Co-pending U.S. Appl. No. 13/983,844, 371(c) date Feb. 20, 2014.
Co-pending U.S. Appl. No. 14/118,323, national stage entry Nov. 18, 2013.
Co-pending U.S. Appl. No. 14/118,330, national stage entry Nov. 18, 2013.
Co-pending U.S. Appl. No. 14/096,557, filed Dec. 4, 2013.
Co-pending U.S. Appl. No. 14/184,745, filed Feb. 20, 2014.

\* cited by examiner

LYSINE SPECIFIC DEMETHYLASE-1 INHIBITORS AND THEIR USE

The invention relates to compounds and their use in therapy.

Cancer is prevalent: there were about 3.2 million cancer cases diagnosed (53,% men, 47% women) and 1.7 million deaths from cancer (56% men, 44% women) in Europe (Ferlay et al. (2007) *Ann. Oncol.* 18(3):581-92). In the United States, the probability of developing invasive cancer is 38% for females and 46% for males that live to be 70 years old and older. In the US about 1.4 million new cases of cancer are expected for 2006. Although the five year survival rate for cancer is now 65%, up from about 50% in the mid-nineteen seventies, cancer is deadly. It is estimated that 565,000 people in the United States will die from cancer in 2006 (American Cancer Society, Surveillance Research, 2006). Despite tremendous advances in cancer treatment and diagnosis, cancer remains a major public health concern. Accordingly, there is a need for new therapeutics with activity in cancer.

Another health crisis is facing industrialized nations. As the population in these countries age, neurodegenerative diseases are affecting more and more people, posing a tremendous economic burden to national health systems. Alzheimer's disease is the largest neurodegenerative disease; disease modifying drugs have long been sought, but to-date, none have been identified. Other neurodegenerative conditions include Parkinson's disease, Huntington's disease, Lewy Body dementia, and which are all characterized by disease progression which robs the patients of their ability to perform normal daily activities, eventually leading to death.

One similar characteristic amongst many cancers and neurodegenerative diseases is aberrant gene expression. A number of compounds have been shown to alter gene expression, including histone deacetylase inhibitors which alter the histone acetylation profile of chromatin. Histone deacetylase inhibitors like SAHA, TSA, and many others have been shown to alter gene expression in various in vitro and in vivo animal models. Another modification that is involved in regulating gene expression is histone methylation. Histones can be subject to numerous modifications including lysine and arginine methylation. The methylation status of histone lysines has recently been shown to be important in dynamically regulating gene expression.

A group of enzymes known as histone lysine methyl transferases and histone lysine demethylases are involved in histone lysine modifications. One particular human histone lysine demethylase enzyme called Lysine Specific Demethylase-1 (LSD1) was recently discovered (Shi et al. (2004)*Cell* 119:941) to be involved in this crucial histone modification. Inactivation of LSD1 in Drosophila (dLSD1) strongly affects the global level of mono and dimethyl-H3-K4 methylation but not methyl-H3K9, while the levels of some other histone methylation and acetylation marks remained the same. dLSD1 inactivation resulted in elevated expression of a subset of genes, including neuronal genes in non-neuronal cells analogous to the functions of LSD1 in human cells. In Drosophila, dLsd1 is not an essential gene, but animal viability is strongly reduced in mutant animals in a gender specific manner (Destefano et al. (2007) *Curr Biol.* 17(9):808-12). Mouse homozygous LSD1 knock-outs were embryonic lethal.

LSD1 has a fair degree of structural similarity, and amino acid identity/homology to polyamine oxidases and monoamine oxidases, all of which (i.e., MAO-A, MAO-B and LSD1) are flavin dependent amine oxidases which catalyze the oxidation of nitrogen-hydrogen bonds and/or nitrogen-carbon bonds. Recent experiments with LSD1 have shown that it is involved in diverse processes such as carcinogenesis (Kahl et al. (2006) *Cancer Res.* 66:1341-11347) and vascular inflammation (Reddy et al. (2008) *Circ. Res.* 103:615). It was found that a commercially available antidepressant, Parnate®, which targets monoamine oxidase (MAO), also inhibits LSD1 at clinically relevant concentrations (Lee et al. (2006) *Chem. Biol.* 13:563-567). Schmidt et al. found "$IC_{50}$ values for 2-PCPA of 20.7-2.1 µM for LSD1, 2.3±0.2 µM for MAO A, and 0.95±0.07 µM for MAO B." See Schmidt et al. (2007) *Biochemistry* 46(14)4408-4416. Thus, Parnate (2-PCPA) is a better inhibitor of MAO-A and MAO-B as compared to LSD1. Schmidt et al. note that the IC50 values for irreversible inhibitors of LSD1 like parnate can greatly depend on assay conditions. Additionally, derivatives of Parnate also can inhibit LSD1 (Gooden et al. (2008) *Bioorg. Med. Chem. Let.* 18:3047-3051). Another class of compounds was recently disclosed to inhibit LSD1 activity: polyamines (Huang et al. (2007) *PNAS* 104:8023-8028). These polyamines inhibit LSD1 modestly and were shown to cause the re-expression of genes aberrantly silenced in cancer cells.

LSD1 is also involved in regulating the methylation of lysines of some proteins which are not histones, like P53 and DNMT1 which both have critical roles in cancer.

Lee et al. ((2006) *Chem. Biol.* 13:563-567) reported that tranylcypromine inhibits histone H3K4 demethylation and can derepress Egr1 gene expression in some cancer lines. A body of evidence is accumulating that Egr-1 is a tumor suppressor gene in many contexts. Calogero et al. ((2004) *Cancer Cell International* 4:1) reported that Egr-1 is downregulated in brain cancers and exogenous expression of Egr-1 resulted in growth arrest and eventual cell death in primary cancer cell lines. Lucerna et al. ((2006) *Cancer Research* 66, 6708-6713) showed that sustained expression of Egr-1 causes antiangiogeneic effects and inhibits tumor growth in some models. Ferraro et al. ((2005) *J Clin Oncol.* March 20; 23(9):1921-6) reported that Egr-1 is downregulated in lung cancer patients with a higher risk of recurrence and may be more resistant to therapy. Scoumanne et al. ((2007) *J Biol. Chem.* May 25; 282(21):15471-5) observed that LSD1 is required for cell proliferation. They found that deficiency in LSD1 leads to a partial cell cycle arrest in G2/M and sensitizes cells to growth suppression induced by DNA damage. Kahl et al. ((2006) *Cancer Res.* 66(23):11341-7) found that LSD1 expression is correlated with prostate cancer aggressiveness. Metzger et al. ((2005) *Nature* 15; 437(7057):436-9) reported that LSD1 modulation by siRNA and pargyline regulates androgen receptor (AR) and may have therapeutic potential in cancers where AR plays a role, like prostate, testis, and brain cancers. Thus, a body of evidence has implicated LSD1 in a number of cancers, which suggests that LSD1 is a therapeutic target for cancer.

The phenylcyclopropylamines have been the subject of many studies designed to elucidate a SAR for MAO inhibition. Kaiser et al. ((1962) *J. Med. Chem.* 5:1243-1265); Zirkle et al. ((1962) *J. Med. Chem.* 1265-1284; U.S. Pat. Nos. 3,365,458; 3,471,522; 3,532,749) have disclosed the synthesis and activity of a number of phenylcyclopropylamine related compounds. Zirkle et al. ((1962) *J. Med. Chem.* 1265-1284) reported that mono- and disubstitution of the amino group of trans-2-phenylcyclopropylamine with methyl decreases the activity only slightly whereas monosubstitution with larger groups like alkyl and araalkyl groups results in considerable loss of activity in the tryptamine potentiation assay for MAO activity. Studies have also been conducted with phenylcyclopropylamine related compounds to determine selectivity for MAO-A versus MAO-B since MAO-A inhibitors can cause dangerous side-effects (see e.g., Yoshida et al. (2004) *Bioorg.*

Med. Chem. 12(10):2645-2652; Hruschka et al. (2008) Biorg Med. Chem. (16):7148-7166; Folks et al. (1983) J. Clin. Psychopharmacol. (3)249; and Youdim et al. (1983) Mod. Probl. Pharmacopsychiatry (19):63). Other phenylcyclopropylamine type compounds are disclosed in Bolesov et al. ((1974) Zhurnal Organicheskoi Khimii 10:8 1661-1669), Bolesov et al. ((1974) Zhurnal Organicheskoi Khimii 10:10 2122-2128) and Russian Patent No. 230169 (19681030). Gooden et al. ((2008) Bioorg. Med. Chem. Let. 18:3047-3051) describe the synthesis of phenylcyclopropylamines derivatives and analogs as well as their activity against MAO-A, MAO-B, and LSD1. None of the compound made in Gooden et al. showed a lower Ki for LSD1 as compared to either MAO A or MAO B. Additionally, most of the Gooden et al. phenylcyclopropylamine derivatives were better inhibitors of MAO-A as compared to MAO-B.

Lee et al. ((2003) J. Comb. Chem. 5:172-187, and related patent references including US patent publication no. 2006148904 and WO2007005896) disclose the lead optimization of [1,2] diamines as potential antituberculosis preclinical candidates.

In view of the lack of adequate treatments for conditions such as cancer, there is a desperate need for disease modifying drugs and drugs that work by inhibiting novel targets. There is a need for the development of LSD1 selective inhibitors particularly those which selectively inhibit LSD1.

This problem is solved by the aspects and embodiments of the invention as characterized herein below in the appended examples and claims.

SUMMARY OF THE INVENTION

The present invention relates to the identification of compounds and their use in treating or preventing diseases. The present invention provides compounds of Formula I, pharmaceutical compositions comprising a compound of Formula I or a pharmaceutically acceptable salt or solvate thereof, and a pharmaceutically acceptable carrier, and their use for treating or preventing diseases. One use of the compounds of Formula I is for treating or preventing cancer. Another use for the compounds of Formula I is to inhibit LSD1.

The invention provides a compound of Formula I or a pharmaceutically acceptable salt or solvate thereof:

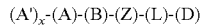

(A')$_x$-(A)-(B)-(Z)-(L)-(D)          I wherein:
(A) is heteroaryl or aryl covalently bonded to (B) and to (A'), if present; each (A'), if present, is independently chosen from aryl, arylalkoxy, arylalkyl, heterocyclyl, aryloxy, halo, alkoxy, haloalkyl, cycloalkyl, haloalkoxy, and cyano, wherein each (A') has 0, 1, 2 or 3 substituents independently chosen from halo, haloalkyl, aryl, arylalkoxy, alkyl, alkoxy, cyano, sulfonyl, amido, and sulfinyl;
X is 0, 1, 2, or 3;
(B) is a cyclopropyl ring which is covalently bonded to (A) and to (Z), wherein (A) and (Z) are covalently bonded to different carbon atoms of (B);
(Z) is —NH—; accordingly (Z) a nitrogen atom covalently bonded to (B), to (L), and to a hydrogen atom;
(L) is a linker covalently bonded to (Z) and to (D), wherein said linker is chosen from —CH$_2$CH$_2$—, —CH$_2$CH$_2$CH$_2$—, and —CH$_2$CH$_2$CH$_2$CH$_2$—; and
(D) is chosen from —N(—R1)-R2, —O—R3, and —S—R3, wherein:
R1 and R2 are mutually linked to form a heterocyclic ring together with the nitrogen atom that R1 and R2 are attached to, wherein said heterocyclic ring has 0, 1, 2, or 3 substituents independently chosen from —NH$_2$, —NH(C$_1$-C$_6$ alkyl), —N(C$_1$-C$_6$ alkyl)(C$_1$-C$_6$ alkyl), alkyl, halo, cyano, alkoxy, haloalkyl, and haloalkoxy, or
R1 and R2 are independently chosen from —H, alkyl, cycloalkyl, haloalkyl, and heterocyclyl, wherein the sum of substituents on R1 and R2 together is 0, 1, 2, or 3 and the substituents are independently chosen from —NH$_2$, —NH (C$_1$-C$_6$ alkyl), —N(C$_1$-C$_6$ alkyl)(C$_1$-C$_6$ alkyl), and fluoro; and
R3 is chosen from —H, alkyl, cycloalkyl, haloalkyl, and heterocyclyl, wherein R3 has 0, 1, 2, or 3 substituents independently chosen from —NH$_2$, —NH(C$_1$-C$_6$ alkyl), —N(C$_1$-C$_6$ alkyl)(C$_1$-C$_6$ alkyl), and fluoro; or an enantiomer, diastereomer, or mixture thereof.

In accordance with the above definition, (D) is thus a nitrogen atom covalently bonded to R1 and to R2,
wherein R1 and R2 are taken together with nitrogen (D) to form a heterocyclic ring having 0, 1, 2, or 3 substituents independently chosen from —NH$_2$, —N(C$_1$-C$_6$ alkyl)(C$_1$-C$_6$ alkyl), —NH(C$_1$-C$_6$ alkyl), alkyl, halo, cyano, alkoxy, haloalkyl, and haloalkoxy, or wherein
R1 and R2 are independently chosen from —H, alkyl, cycloalkyl, haloalkyl, and heterocyclyl, wherein the sum of substituents on R1 and R2 together is 0, 1, 2, or 3 and the substituents are independently chosen from —NH$_2$, —N(C$_1$-C$_6$ alkyl)(C$_1$-C$_6$ alkyl), —NH(C$_1$-C$_6$ alkyl), and fluoro, or
(D) is an oxygen or sulfur atom covalently bonded to (L) and has one substituent R3 chosen from —H, alkyl, cycloalkyl, haloalkyl, and heterocyclyl, wherein said one substituent R3 has 0, 1, 2, or 3 substituents independently chosen from —NH$_2$, —N(C$_1$-C$_6$ alkyl)(C$_1$-C$_6$ alkyl), —NH(C$_1$-C$_6$ alkyl), and fluoro.

The following compounds are excluded from the scope of Formula I:
N1-[(trans)-2-phenylcyclopropyl]-N2-undecyl-rel-1,2-ethanediamine;
N1-[(trans)-2-phenylcyclopropyl]-N2-tricyclo[3.3.1.13,7]dec-2-yl-rel-1,2-ethanediamine;
N1-cyclooctyl-N2-[(trans)-2-phenylcyclopropyl]-rel-1,2-ethanediamine;
N1,N1-dimethyl-N2-(2-phenylcyclopropyl)-1,3-propanediamine;
N1,N1-dimethyl-N2-(2-phenylcyclopropyl)-1,2-ethanediamine; and trans-1-phenyl-2-[(2-hydroxyethyl)amino]cyclopropane;

In a first aspect, the invention provides a compound of Formula I or a pharmaceutically acceptable salt or solvate thereof:

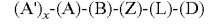

(A')$_x$-(A)-(B)-(Z)-(L)-(D)          I wherein:
(A) is heteroaryl or aryl covalently bonded to (B) and to (A'), if present; each (A'), if present, is independently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, or 2 substituents independently chosen from halo, haloalkyl, aryl, arylalkoxy, alkyl, alkoxy, cyano, sulfonyl, and sulfinyl;
X is 0, 1, 2, or 3;
(B) is a cyclopropyl ring which is covalently bonded to (A) and to (Z), wherein (A) and (Z) are covalently bonded to different carbon atoms of (B);
(Z) is —NH—; accordingly (7) is a nitrogen atom covalently bonded to (B), to (L), and to a hydrogen atom;
(L) is a linker covalently bonded to (Z) and to (D), wherein said linker is chosen from —CH$_2$CH$_2$—, —CH$_2$CH$_2$CH$_2$—, and —CH$_2$CH$_2$CH$_2$CH$_2$—;

(D) is chosen from —N(—R1)-R2, —O—R3, and —S—R3, wherein:

R1 and R2 are mutually linked to form a heterocyclic ring together with the nitrogen atom that R1 and R2 are attached to, wherein said heterocyclic ring has 0, 1, 2, or 3 substituents independently chosen from —NH$_2$, —N(C$_1$-C$_6$ alkyl)(C$_1$-C$_6$ alkyl), alkyl, halo, cyano, alkoxy, haloalkyl, and haloalkoxy, or R1 and R2 are independently chosen from —H, alkyl, cycloalkyl, haloalkyl, and heterocyclyl, wherein the sum of substituents on R1 and R2 together is 0, 1, 2, or 3 and the substituents are independently chosen from —NH$_2$, —N(C$_1$-C$_6$ alkyl)(C$_1$-C$_6$ alkyl), and fluoro; and R3 is chosen from —H, alkyl, cycloalkyl, haloalkyl, and heterocyclyl, wherein R3 has 0, 1, 2, or 3 substituents independently chosen from —NH$_2$, —N(C$_1$-C$_6$ alkyl)(C$_1$-C$_6$ alkyl), and fluoro;

or an enantiomer, diastereomer or mixture thereof;

with the proviso that the compound of Formula I is not:

N1-[(trans)-2-phenylcyclopropyl]-N2-undecyl-rel-1,2-ethanediamine;

N1-[(trans)-2-phenylcyclopropyl]-N2-tricyclo[3.3.1.13,7]dec-2-yl-rel-1,2-ethanediamine;

N1-cyclooctyl-N2-[(trans)-2-phenylcyclopropyl]-rel-1,2-ethanediamine;

N1,N1-dimethyl-N2-(2-phenylcyclopropyl)-1,2-ethanediamine;

N1,N1-dimethyl-N2-(2-phenylcyclopropyl)-1,3-propanediamine;

trans-1-phenyl-2-[(2-hydroxyethyl)amino]cyclopropane;

or an enantiomer, diastereomer, or mixture thereof of said compound.

In accordance with the above definition, (D) is thus a nitrogen atom covalently bonded to R1, to R2, and to (L);

wherein R1 and R2 are taken together with nitrogen (D) to form a heterocyclic ring having 0, 1, 2, or 3 substituents independently chosen from —NH$_2$, —N(C$_1$-C$_6$ alkyl)(C$_1$-C$_6$ alkyl), alkyl, halo, cyano, alkoxy, haloalkyl, and haloalkoxy, or wherein R1 and R2 are independently chosen from —H, alkyl, cycloalkyl, haloalkyl, and heterocyclyl, wherein the sum of substituents on R1 and R2 together is 0, 1, 2, or 3 and the substituents are independently chosen from —NH$_2$, —N(C$_1$-C$_6$ alkyl)(C$_1$-C$_6$ alkyl), and fluoro, or (D) is an oxygen or sulfur atom covalently bonded to (L) and has one substituent R3 chosen from —H, alkyl, cycloalkyl, haloalkyl, and heterocyclyl, wherein said one substituent R3 has 0, 1, 2, or 3 substituents independently chosen from —N(C$_1$-C$_6$ alkyl)(C$_1$-C$_6$ alkyl), and fluoro.

In a related aspect, the invention provides a pharmaceutical composition comprising a compound of Formula I as defined above or a pharmaceutically acceptable salt or solvate thereof and a pharmaceutically acceptable carrier.

In one embodiment of the first aspect, the invention provides a compound of Formula I or a pharmaceutically acceptable salt or solvate thereof, wherein (A) is aryl and the other variables are as defined above in the broadest definition of the first aspect of the invention.

In one embodiment of the first aspect, the invention provides a compound of Formula I or a pharmaceutically acceptable salt or solvate thereof, wherein (A) is phenyl and the other variables are as defined above in the broadest definition of the first aspect of the invention.

In one embodiment of the first aspect, the invention provides a compound of Formula I or a pharmaceutically acceptable salt or solvate thereof, wherein X is 1 or 2 and the other variables are as defined above in the broadest definition of the first aspect of the invention.

In one embodiment of the first aspect, the invention provides a compound of Formula I or a pharmaceutically acceptable salt or solvate thereof, wherein X is 1; and (A') is chosen from aryl and arylalkoxy wherein said aryl or arylalkoxy has 0 or 1 substituent chosen from halo and haloalkyl, and the other variables are as defined above in the broadest definition of the first aspect of the invention.

In one embodiment of the first aspect, the invention provides a compound of Formula I or a pharmaceutically acceptable salt or solvate thereof, wherein R1 and R2 are taken together with nitrogen (D) to give a 4, 5, 6, 7, 8, or 9 membered heterocyclic ring having 0, 1, 2, or 3 substituents independently chosen from —NH$_2$, —N(C$_1$-C$_6$ alkyl)(C$_1$-C$_6$ alkyl), alkyl, halo, cyano, alkoxy, haloalkyl, and haloalkoxy, and the other variables are as defined above in the broadest definition of the first aspect of the invention.

In one embodiment of the first aspect, the invention provides a compound of Formula I or a pharmaceutically acceptable salt or solvate thereof, wherein R1 and R2 are independently chosen from —H, alkyl, cycloalkyl, and haloalkyl wherein the sum of substituents on R1 and R2 together is 0, 1, 2, or 3 wherein the substituents are independently chosen from —NH$_2$, —N(C$_1$-C$_6$ alkyl)(C$_1$-C$_6$ alkyl), and fluoro and the other variables are as defined above in the broadest definition of the first aspect of the invention.

In one embodiment of the first aspect, the invention provides a compound of Formula I or a pharmaceutically acceptable salt or solvate thereof, wherein R1 is —H and R2 is chosen from a 3, 4, 5, 6, or 7 membered cycloalkyl group having 0 or 1 substituent chosen from —NH$_2$ and —N(C$_1$-C$_6$ alkyl)(C$_1$-C$_6$ alkyl) and the other variables are as defined above in the broadest definition of the first aspect of the invention.

In one embodiment of the first aspect, the invention provides a compound of Formula I or a pharmaceutically acceptable salt or solvate thereof, wherein R1 and R2 are independently chosen from —H, C3-C7 cycloalkyl, C2-C10 alkyl, haloalkyl, and heterocyclyl, wherein the sum of substituents on R1 and R2 together is from 0-3 wherein the substituents are independently chosen from —NH$_2$, —N(C$_1$-C$_6$ alkyl)(C$_1$-C$_6$ alkyl), and fluoro and the other variables are as defined above in the broadest definition of the first aspect of the invention.

In one embodiment of the first aspect, the invention provides a compound of Formula I or a pharmaceutically acceptable salt or solvate thereof, wherein R1 and R2 are taken together with nitrogen (D) to give a heterocyclic ring chosen from azetidinyl, pyrrolidinyl, piperidinyl, and morpholino wherein said heterocyclic ring has 0 or 1 substituent chosen from —NH$_2$, —N(C$_1$-C$_6$ alkyl)(C$_1$-C$_6$ alkyl), alkyl, halo, cyano, alkoxy, haloalkyl, and haloalkoxy and the other variables are as defined above in the broadest definition of the first aspect of the invention.

In one embodiment of the first aspect, the invention provides a compound of Formula I or a pharmaceutically acceptable salt or solvate thereof, wherein (A) is heteroaryl and the other variables are as defined above in the broadest definition of the first aspect of the invention.

In one embodiment of the first aspect, the invention provides a compound of Formula I or a pharmaceutically acceptable salt or solvate thereof, wherein (A) is a heteroaryl chosen from pyridyl, pyrimidinyl, and thiophenyl and the other variables are as defined above in the broadest definition of the first aspect of the invention.

In one embodiment of the first aspect, the invention provides a compound of Formula I or a pharmaceutically acceptable salt or solvate thereof, wherein (L) is a linker chosen from —CH₂CH₂— and —CH₂CH₂CH₂— and the other variables are as defined above in the broadest definition of the first aspect of the invention.

In one embodiment of the first aspect, the invention provides a compound of Formula I or a pharmaceutically acceptable salt or solvate thereof, wherein (L) is —CH₂CH₂— and the other variables are as defined above in the broadest definition of the first aspect of the invention.

In one embodiment of the first aspect, the invention provides a compound of Formula I or a pharmaceutically acceptable salt or solvate thereof, wherein (B) is a cyclopropyl ring which is covalently bonded to (A) and to (Z), wherein (A) and (Z) are covalently bonded to different carbon atoms of (B), and wherein (A) and (Z) are in the trans orientation with respect to the cyclopropyl ring (B) and the other variables are as defined above in the broadest definition of the first aspect of the invention.

In one embodiment of the first aspect, the invention provides a compound of Formula I or a pharmaceutically acceptable salt or solvate thereof, wherein (B) is a cyclopropyl ring which is covalently bonded to (A) and to (Z), wherein (A) and (Z) are covalently bonded to different carbon atoms of (B), and wherein (A) and (Z) are in the trans orientation with respect to the cyclopropyl ring (B), and wherein 1 (A') group is present (X=1) and said (A') group is in the meta or para position with respect to the cyclopropyl ring and the other variables are as defined above in the broadest definition of the first aspect of the invention. Preferably the one (A') group is in the para position with respect to the cyclopropyl ring wherein said (A') group is chosen from aryl and arylalkoxy wherein said aryl or arylalkoxy group has 0, 1, or 2 substituents independently chosen from halo, haloalkyl, aryl, arylalkoxy, alkyl, alkoxy, cyano, sulfonyl, and sulfinyl. Preferably the 0, 1, or 2 substituents on (A') are independently chosen from halo and haloalkyl.

In one embodiment of the first aspect of the invention, a compound of Formula I or a pharmaceutically acceptable salt or solvate thereof is provided wherein (D) is an oxygen or sulphur atom having one substituent R3 chosen from —H, alkyl, cycloalkyl, haloalkyl, and heterocyclyl, wherein said one substituent R3 has 0, 1, 2, or 3 substituents independently chosen from —NH₂, —N(C₁-C₆ alkyl)(C₁-C₆ alkyl), and fluoro, provided that when (D) is an oxygen R3 is not a hydrogen.

In a second aspect, the invention provides a compound of Formula I or a pharmaceutically acceptable salt or solvate thereof:

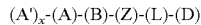

(A')ₓ-(A)-(B)-(Z)-(L)-(D)    I wherein:
(A) is heteroaryl or aryl covalently bonded to (B) and to (A'), if present; each (A'), if present, is independently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, or 2 substituents independently chosen from halo, haloalkyl, aryl, arylalkoxy, alkyl, alkoxy, cyano, sulfonyl, and sulfinyl;
X is 0, 1, 2, or 3;
(B) is a cyclopropyl ring which is covalently bonded to (A) and to (Z), wherein (A) and (Z) are covalently bonded to different carbon atoms of (B);
(Z) is —NH—; accordingly (Z) is a nitrogen atom covalently bonded to (B), to (L), and to a hydrogen atom;

(L) is a linker covalently bonded to (Z) and to (D), wherein said linker is chosen from —CH₂CH₂—, —CH₂CH₂CH₂—, and —CH₂CH₂CH₂CH₂—;
(D) is a nitrogen atom covalently bonded to R1, to R2, and to (L),
wherein R1 and R2 are taken together with nitrogen (D) to form a heterocyclic ring having 0, 1, 2, or 3 substituents independently chosen from —NH₂, —N(C₁-C₆ alkyl)(C₁-C₆ alkyl), alkyl, halo, cyano, alkoxy, haloalkyl, and haloalkoxy, or wherein
R1 and R2 are independently chosen from —H, alkyl, cycloalkyl, haloalkyl, and heterocyclyl, wherein the sum of substituents on R1 and R2 together is 0, 1, 2, or 3 and the substituents are independently chosen from —NH₂, —N(C₁-C₆ alkyl)(C₁-C₆ alkyl), and fluoro, or
(D) is an oxygen or sulfur atom covalently bonded to (L) and has one substituent R3 chosen from alkyl, cycloalkyl, haloalkyl, and heterocyclyl, wherein said one substituent has 0, 1, 2, or 3 substituents independently chosen from —NH₂, —N(C₁-C₆ alkyl)(C₁-C₆ alkyl), and fluoro;
or an enantiomer, diastereomer, or mixture thereof;
with the proviso that the compound of formula (I) is not:
N1-[(trans)-2-phenylcyclopropyl]-N2-undecyl-rel-1,2-ethanediamine;
N1-[(trans)-2-phenylcyclopropyl]-N2-tricyclo[3.3.1.13,7]dec-2-yl-rel-1,2-ethanediamine;
N1-cyclooctyl-N2-[(trans)-2-phenylcyclopropyl]-rel-1,2-ethanediamine;
N1,N1-dimethyl-N2-(2-phenylcyclopropyl)-1,2-ethanediamine;
N,N-dimethyl-N'-(2-phenylcyclopropyl)-1,3-propanediamine;
or an enantiomer, diastereomer, or mixture thereof of said compound.

In a related aspect, the invention provides a pharmaceutical composition comprising a compound of Formula I or a pharmaceutically acceptable salt or solvate thereof as defined above and a pharmaceutically acceptable carrier.

In a third aspect, the invention provides a method of treating or preventing a disease or condition comprising administering, to a subject/patient (preferably, a human) in need of treatment or prevention, a therapeutically effective amount of a composition comprising a compound of Formula I or a pharmaceutically acceptable salt or solvate thereof as defined above in said first or second aspect of the invention or embodiment thereof and a pharmaceutically acceptable carrier. This aspect can be reformulated as a compound of Formula I or a pharmaceutically acceptable salt or solvate thereof for use as a medicine. Accordingly, the invention provides a pharmaceutical composition comprising a compound of Formula I or a pharmaceutically acceptable salt or solvate thereof, as defined above in said first or second aspect of the invention or any embodiment thereof, and a pharmaceutically acceptable carrier.

In a fourth aspect, the invention provides a method of inhibiting LSD1 activity comprising administering, to a subject/patient (preferably, a human) in need of treatment, an amount of a pharmaceutical composition comprising a compound of Formula I' or a pharmaceutically acceptable salt thereof:

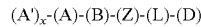

(A')ₓ-(A)-(B)-(Z)-(L)-(D)    I' wherein:
(A) is heteroaryl or aryl covalently bonded to (B) and to (A'), if present; each (A'), if present, is independently chosen from aryl, arylalkoxy, arylalkyl, heterocyclyl, aryloxy, halo, alkoxy, haloalkyl, cycloalkyl, haloalkoxy, and cyano, wherein each (A') has 0, 1, or 2 substituents independently chosen from halo, haloalkyl, aryl, arylalkoxy, alkyl, alkoxy, cyano, sulfonyl, and sulfinyl;

X is 0, 1, 2, or 3;

(B) is a cyclopropyl ring which is covalently bonded to (A) and to (Z), wherein (A) and (Z) are covalently bonded to different carbon atoms of (B);

(Z) is —NH—; accordingly Z is a nitrogen atom covalently bonded to (B), to (L), and to a hydrogen atom;

(L) is a linker covalently bonded to (Z) and to (D), wherein said linker is chosen from —$CH_2CH_2$—, —$CH_2CH_2CH_2$—, and —$CH_2CH_2CH_2CH_2$—;

(D) is a nitrogen atom covalently bonded to R1, to R2, and to (L);

wherein R1 and R2 are taken together with nitrogen (D) to form a heterocyclic ring having 0, 1, 2, or 3 substituents independently chosen from —$NH_2$, —$N(C_1$-$C_6$ alkyl)($C_1$-$C_6$ alkyl), alkyl, halo, cyano, alkoxy, haloalkyl, and haloalkoxy, or wherein R1 and R2 are independently chosen from —H, alkyl, cycloalkyl, haloalkyl, and heterocyclyl, wherein the sum of substituents on R1 and R2 together is 0, 1, 2, or 3 and the substituents are independently chosen from —$NH_2$, —$N(C_1$-$C_6$ alkyl)($C_1$-$C_6$ alkyl), and fluoro, or (D) is an oxygen or sulfur atom covalently bonded to (L) and has one substituent R3 chosen from —H, alkyl, cycloalkyl, haloalkyl, and heterocyclyl, wherein said one substituent R3 has 0, 1, 2, or 3 substituents independently chosen from —$NH_2$, —$N(C_1$-$C_6$ alkyl)($C_1$-$C_6$ alkyl), and fluoro; and a pharmaceutically acceptable carrier in an amount sufficient to inhibit LSD1 activity.

The above definition provided for (D) can be reformulated as follows: (D) is chosen from —N(—R1)-R2, —O—R3, and —S—R3, wherein:

R1 and R2 are mutually linked to form a heterocyclic ring together with the nitrogen atom that R1 and R2 are attached to, wherein said heterocyclic ring has 0, 1, 2, or 3 substituents independently chosen from —$NH_2$, —$N(C_1$-$C_6$ alkyl)($C_1$-$C_6$ alkyl), alkyl, halo, cyano, alkoxy, haloalkyl, and haloalkoxy, or R1 and R2 are independently chosen from —H, alkyl, cycloalkyl, haloalkyl, and heterocyclyl, wherein the sum of substituents on R1 and R2 together is 0, 1, 2, or 3 and the substituents are independently chosen from —$NH_2$, —$N(C_1$-$C_6$ alkyl)($C_1$-$C_6$ alkyl), and fluoro; and R3 is chosen from —H, alkyl, cycloalkyl, haloalkyl, and heterocyclyl, wherein R3 has 0, 1, 2, or 3 substituents independently chosen from —$NH_2$, —$N(C_1$-$C_6$ alkyl)($C_1$-$C_6$ alkyl), and fluoro.

This aspect can be reformulated as a compound of Formula I' as herein defined for use as a LSD1 inhibitor. This aspect can also be reformulated as a compound of Formula I' for use in the treatment or prevention of a disease associated with LSD1.

In a fifth aspect, the invention provides a method of treating or preventing cancer comprising administering, to a subject/patient (preferably, a human) in need of treatment or prevention, a therapeutically effectively amount of a composition comprising a compound of Formula I' which is an LSD1 inhibitor as defined above in the fourth aspect of the invention and a pharmaceutically acceptable carrier. This aspect can be reformulated as a compound of Formula I' as defined above in the fourth aspect of the invention for use in treating or preventing cancer. This aspect can be reformulated as a compound of Formula I' as defined in the fourth aspect of the invention for use in treating or preventing cancer. Preferably, the cancer is chosen from breast cancer, colorectal cancer, lung cancer, prostate cancer, skin cancer, testicular cancer, blood cancer, and brain cancer.

In a sixth aspect, the invention provides a method of treating or preventing cancer comprising administering, to a subject/patient (preferably, a human) in need of treatment or prevention, a therapeutically effectively amount of a composition comprising a compound of Formula I or a pharmaceutically acceptable salt or solvate thereof, as defined above in said first or second aspect of the invention and their respective embodiments, and a pharmaceutically acceptable carrier. This aspect can be reformulated as a compound of Formula I or a pharmaceutically acceptable salt or solvate thereof, as defined above in said first or second aspect of the invention and their respective embodiments, for use in treating or preventing cancer. Preferably, the cancer is chosen from breast cancer, colorectal cancer, lung cancer, prostate cancer, skin cancer, testicular cancer, blood cancer, and brain cancer.

In another aspect, the invention provides a pharmaceutical composition comprising a pharmaceutically acceptable carrier and a compound of Formula I which is a selective inhibitor of LSD1 as defined in the first or second aspect of the invention and their respective embodiments. LSD1 selective inhibitors have Ki values for LSD1 which are at least 2-fold lower than the Ki value for MAO-A and/or MAO-B. In one embodiment of this aspect, the LSD1 Ki value is at least 5-fold lower than the Ki value for MAO-A and/or MAO-B. In one aspect of this embodiment, the LSD1 Ki value is at least 10-fold lower than the Ki value for MAO-A and MAO-B. In one embodiment of this aspect, the pharmaceutical composition comprising a LSD1 selective inhibitor of Formula I or a pharmaceutically acceptable salt or solvate thereof is useful for treating or preventing a disease in an individual (preferably, a human). In a more specific aspect, the disease is cancer. In an even more specific aspect, the disease is a cancer chosen from prostate, brain, colorectal, lung, breast, testicular, skin, and blood cancer. In one specific aspect, the cancer is prostate cancer. In one specific aspect, the cancer is lung cancer. In one specific aspect, the cancer is brain cancer. In one specific aspect, the cancer is blood cancer (e.g., leukemia). In one specific aspect, the cancer is breast cancer. In one specific aspect, the cancer is colorectal cancer. In one specific aspect, the cancer is skin cancer. In one specific aspect, the cancer is testicular cancer.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION OF THE INVENTION

Figure 1:
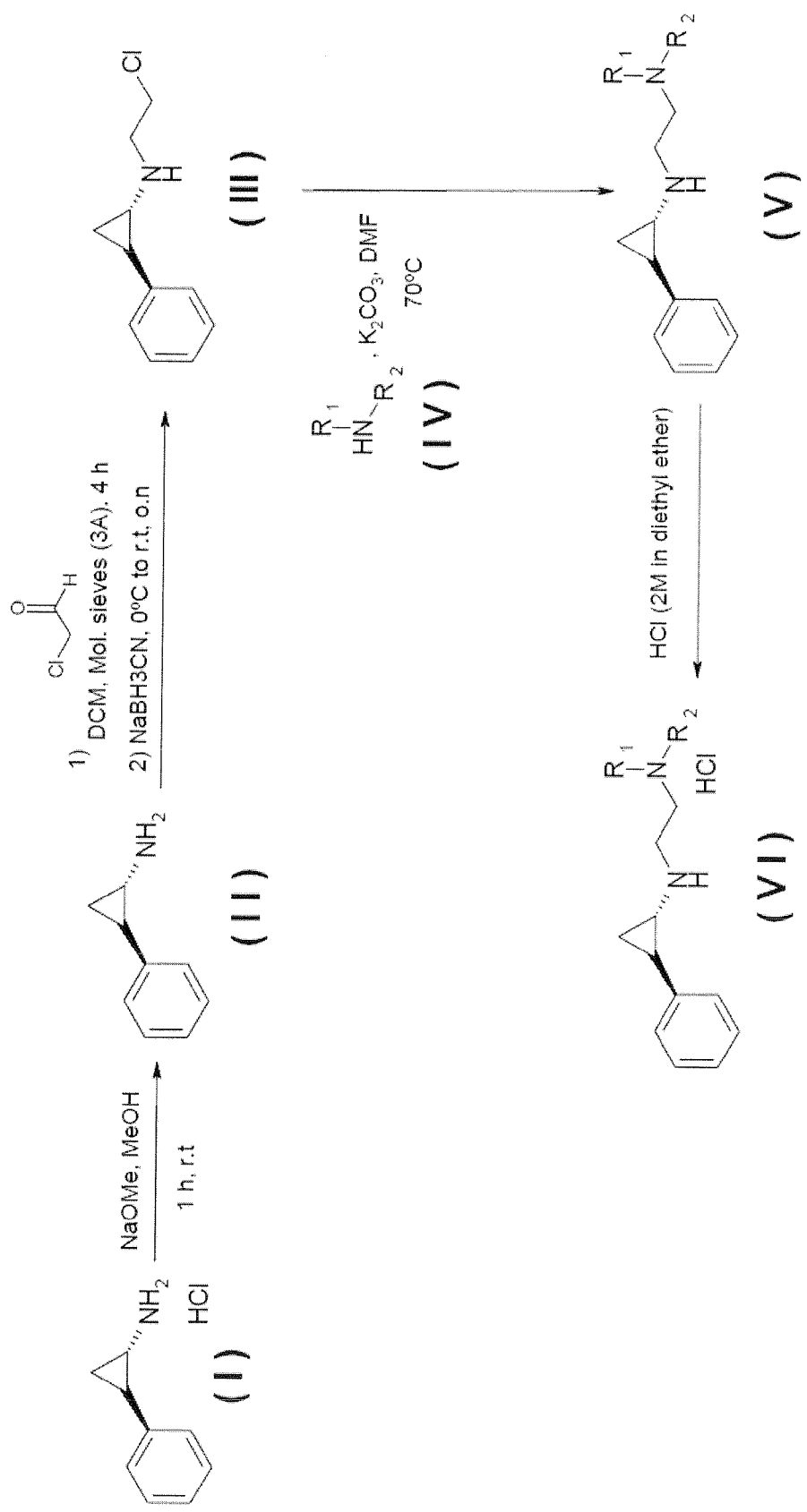
FIG. 1: The compounds of the invention can be synthesized by the general route described in the scheme shown in this figure (Scheme 1). DCM: dichloromethane; DMF: N,N-dimethylformamide.

The present invention relates to the identification of compounds and their use in treating or preventing diseases. The present invention provides a compound of Formula I, pharmaceutical compositions comprising a compound of Formula I or a pharmaceutically acceptable salt or solvate thereof and a pharmaceutically acceptable carrier, and their use for treating or preventing diseases. One use of the compounds of Formula I is for treating or preventing cancer. The compounds of Formula I can be used as LSD1 selective inhibitors that inhibit LSD1 to a greater extent than MAO-A and MAO-B. In particular it was found that (hetero)arylcyclopropylamine derivatives of Formula I, and in particular phenylcyclopropylamine derivatives encompassed by Formula I, yield compounds with unexpectedly potent LSD1 inhibition. The Examples described herein show that compounds of Formula I have Ki values for LSD1 inhibition under 500 nanomolar (see Table 1) which makes them about at least to 50-fold or more potent than tranylcypromine for LSD1 inhibition. These compounds are LSD1 selective in that they inhibit LSD1 to an extent greater than MAO-A and MAO-B.

Accordingly, the invention provides a compound of Formula I or a pharmaceutically acceptable salt or solvate thereof:

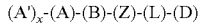   I wherein:
(A) is heteroaryl or aryl covalently bonded to (B) and to (A'), if present; each (A'), if present, is independently chosen from aryl, arylalkoxy, arylalkyl, heterocyclyl, aryloxy, halo, alkoxy, haloalkyl, cycloalkyl, haloalkoxy, and cyano, wherein each (A') has 0, 1, 2 or 3 substituents independently chosen from halo, haloalkyl, aryl, arylalkoxy, alkyl, alkoxy, cyano, sulfonyl, amido, and sulfinyl;
X is 0, 1, 2, or 3;
(B) is a cyclopropyl ring which is covalently bonded to (A) and to (Z), wherein (A) and (Z) are covalently bonded to different carbon atoms of (B);
(Z) is —NH—; accordingly (Z) a nitrogen atom covalently bonded to (B), to (L), and to a hydrogen atom;
(L) is a linker covalently bonded to (Z) and to (D), wherein said linker is chosen from —CH$_2$CH$_2$—, —CH$_2$CH$_2$CH$_2$—, and —CH$_2$CH$_2$CH$_2$CH$_2$—;
(D) is a nitrogen atom covalently bonded to R1 and to R2, wherein R1 and R2 are taken together with nitrogen (D) to form a heterocyclic ring having 0, 1, 2, or 3 substituents independently chosen from —NH$_2$, —N(C$_1$-C$_6$ alkyl)(C$_1$-C$_6$ alkyl), —NH(C$_1$-C$_6$ alkyl), alkyl, halo, cyano, alkoxy, haloalkyl, and haloalkoxy, or wherein
R1 and R2 are independently chosen from —H, alkyl, cycloalkyl, haloalkyl, and heterocyclyl, wherein the sum of substituents on R1 and R2 together is 0, 1, 2, or 3 and the substituents are independently chosen from —NH$_2$, —N(C$_1$-C$_6$ alkyl)(C$_1$-C$_6$ alkyl), —NH(C$_1$-C$_6$ alkyl), and fluoro, or
(D) is an oxygen or sulfur atom covalently bonded to (L) and has one substituent R3 chosen from —H, alkyl, cycloalkyl, haloalkyl, and heterocyclyl, wherein said one substituent R3 has 0, 1, 2, or 3 substituents independently chosen from —NH$_2$, —N(C$_1$-C$_6$ alkyl)(C$_1$-C$_6$ alkyl), —NH(C$_1$-C$_6$ alkyl), and fluoro; or an enantiomer, diastereomer, or mixture thereof,
wherein when X is 0 and
when (D) is oxygen then R3 is chosen from alkyl, cycloalkyl, haloalkyl, heterocyclyl or
when X is 0 and when (L) is —CH$_2$CH$_2$— or —CH$_2$CH$_2$CH$_2$— and (D) is a nitrogen then R1 and R2 both are not methyl or
when (L) is —CH$_2$CH$_2$— and one of R1 and R2 is —H the other of R1 and R2 is not undecyl or tricyclo[3.3.1.13,7]dec-2-yl.

In a first aspect, the invention provides a compound of Formula I or a pharmaceutically acceptable salt or solvate thereof:

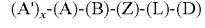   I wherein:
(A) is heteroaryl or aryl covalently bonded to (B) and to (A'), if present; each (A'), if present, is independently chosen from aryl, arylalkoxy, arylalkyl, heterocyclyl, aryloxy, halo, alkoxy, haloalkyl, cycloalkyl, haloalkoxy, and cyano, wherein each (A') has 0, 1, or 2 substituents independently chosen from halo, haloalkyl, aryl, arylalkoxy, alkyl, alkoxy, cyano, sulfonyl, and sulfinyl;
X is 0, 1, 2, or 3;
(B) is a cyclopropyl ring which is covalently bonded to (A) and to (Z), wherein (A) and (Z) are covalently bonded to different carbon atoms of (B);
(Z) is —NH—; accordingly (Z) a nitrogen atom covalently bonded to (B), to (L), and to a hydrogen atom;
(L) is a linker covalently bonded to (Z) and to (D), wherein said linker is chosen from —CH$_2$CH$_2$—, —CH$_2$CH$_2$CH$_2$—, and —CH$_2$CH$_2$CH$_2$CH$_2$—;
(D) is a nitrogen atom covalently bonded to R1 and to R2, wherein R1 and R2 are taken together with nitrogen (D) to form a heterocyclic ring having 0, 1, 2, or 3 substituents independently chosen from —NH$_2$, —N(C$_1$-C$_6$ alkyl)(C$_1$-C$_6$ alkyl), alkyl, halo, cyano, alkoxy, haloalkyl, and haloalkoxy, or wherein
R1 and R2 are independently chosen from —H, alkyl, cycloalkyl, haloalkyl, and heterocyclyl, wherein the sum of substituents on R1 and R2 together is 0, 1, 2, or 3 and the substituents are independently chosen from —NH$_2$, —N(C$_1$-C$_6$ alkyl)(C$_1$-C$_6$ alkyl), and fluoro, or
(D) is an oxygen or sulfur atom covalently bonded to (L) and has one substituent R3 chosen from —H, alkyl, cycloalkyl, haloalkyl, and heterocyclyl, wherein said one substituent R3 has 0, 1, 2, or 3 substituents independently chosen from —NH$_2$, —N(C$_1$-C$_6$ alkyl)(C$_1$-C$_6$ alkyl), and fluoro; or an enantiomer, diastereomer, or mixture thereof, with the proviso that the compound of formula (I) is not:
N1-[(trans)-2-phenylcyclopropyl]-N2-undecyl-rel-1,2-ethanediamine;
N1-[(trans)-2-phenylcyclopropyl]-N2-tricyclo[3.3.1.13,7]dec-2-yl-rel-1,2-ethanediamine;
N1-cyclooctyl-N2-[(trans)-2-phenylcyclopropyl]-rel-1,2-ethanediamine;
N1,N1-dimethyl-N2-(2-phenylcyclopropyl)-1,2-ethanediamine;
N1,N1-dimethyl-N2-(2-phenylcyclopropyl)-1,3-propanediamine;
trans-1-phenyl-2-[(2-hydroxyethyl)amino]cyclopropane;
or an enantiomer, diastereomer, or mixture thereof.

In a related aspect, the invention provides a pharmaceutical composition comprising a compound of Formula I or a pharmaceutically acceptable salt or solvate thereof as defined above and a pharmaceutically acceptable carrier. In a preferred aspect, the composition of this aspect is used for treating or preventing cancer.

In one embodiment of the first aspect, the invention provides a compound of Formula I or a pharmaceutically acceptable salt or solvate thereof, wherein (A) is aryl and the other variables are as defined above in the broadest definition of the first aspect of the invention.

In one embodiment of the first aspect, the invention provides a compound of Formula I or a pharmaceutically acceptable salt or solvate thereof, wherein (A) is phenyl and the other variables are as defined above in the broadest definition of the first aspect of the invention.

In one embodiment of the first aspect, the invention provides a compound of Formula I or a pharmaceutically acceptable salt or solvate thereof, wherein X is 1 or 2 and the other variables are as defined above in the broadest definition of the first aspect of the invention.

In one embodiment of the first aspect, the invention provides a compound of Formula I or a pharmaceutically acceptable salt or solvate thereof, wherein X is 1; and (A') is chosen from aryl and arylalkoxy wherein said aryl or arylalkoxy group has 0 or 1 substituent chosen from halo and haloalkyl and the other variables are as defined above in the broadest definition of the first aspect of the invention.

In one embodiment of the first aspect, the invention provides a compound of Formula I or a pharmaceutically acceptable salt or solvate thereof, wherein R1 and R2 are taken together with nitrogen (D) to give a 4, 5, 6, 7, 8, or 9 membered heterocyclic ring having 0, 1, 2, or 3 substituents independently chosen from —$NH_2$, —$N(C_1$-$C_6$ alkyl)($C_1$-$C_6$ alkyl), alkyl, halo, cyano, alkoxy, haloalkyl, and haloalkoxy and the other variables are as defined above in the broadest definition of the first aspect of the invention.

In one embodiment of the first aspect, the invention provides a compound of Formula I or a pharmaceutically acceptable salt or solvate thereof, wherein R1 and R2 are independently chosen from —H, alkyl, cycloalkyl, and haloalkyl wherein the sum of substituents on R1 and R2 together is 0, 1, 2, or 3 wherein the substituents are independently chosen from —$NH_2$, —$N(C_1$-$C_6$ alkyl)($C_1$-$C_6$ alkyl), and fluoro and the other variables are as defined above in the broadest definition of the first aspect of the invention.

In one embodiment of the first aspect, the invention provides a compound of Formula I or a pharmaceutically acceptable salt or solvate thereof, wherein R1 is —H and R2 is chosen from a 3, 4, 5, 6, or 7 membered cycloalkyl group having 0 or 1 substituent chosen from —$NH_2$ and —$N(C_1$-$C_6$ alkyl)($C_1$-$C_6$ alkyl) and the other variables are as defined above in the broadest definition of the first aspect of the invention.

In one embodiment of the first aspect, the invention provides a compound of Formula I or a pharmaceutically acceptable salt or solvate thereof, wherein R1 and R2 are independently chosen from —H, $C_3$-$C_7$ cycloalkyl, $C_2$-$C_{10}$ alkyl, haloalkyl, and heterocyclyl, wherein the sum of substituents on R1 and R2 together is 0, 1, 2, or 3 wherein the substituents are independently chosen from —$NH_2$, —$N(C_1$-$C_6$ alkyl)($C_1$-$C_6$ alkyl), and fluoro and the other variables are as defined above in the broadest definition of the first aspect of the invention.

In one embodiment of the first aspect, the invention provides a compound of Formula I or a pharmaceutically acceptable salt or solvate thereof, wherein R1 and R2 are taken together with nitrogen (D) to give a heterocyclic ring chosen from azetidinyl, pyrrolidinyl, piperidinyl, and morpholino wherein said heterocyclic ring has 0 or 1 substituent chosen from —$NH_2$, —$N(C_1$-$C_6$ alkyl)($C_1$-$C_6$ alkyl), alkyl, halo, cyano, alkoxy, haloalkyl, and haloalkoxy and the other variables are as defined above in the broadest definition of the first aspect of the invention.

In one embodiment of the first aspect, the invention provides a compound of Formula I or a pharmaceutically acceptable salt or solvate thereof, wherein (A) is heteroaryl and the other variables are as defined above in the broadest definition of the first aspect of the invention.

In one embodiment of the first aspect, the invention provides a compound of Formula I or a pharmaceutically acceptable salt or solvate thereof, wherein (A) is a heteroaryl chosen from pyridyl, pyrimidinyl, and thiophenyl and the other variables are as defined above in the broadest definition of the first aspect of the invention.

In one embodiment of the first aspect, the invention provides a compound of Formula I or a pharmaceutically acceptable salt or solvate thereof, wherein (L) is a linker chosen from —$CH_2CH_2$— and —$CH_2CH_2CH_2$— and the other variables are as defined above in the broadest definition of the first aspect of the invention.

In one embodiment of the first aspect, the invention provides a compound of Formula I or a pharmaceutically acceptable salt or solvate thereof, wherein (L) is —$CH_2CH_2$— and the other variables are as defined above in the broadest definition of the first aspect of the invention.

In one embodiment of the first aspect, the invention provides a compound of Formula I or a pharmaceutically acceptable salt or solvate thereof, wherein (B) is a cyclopropyl ring which is covalently bonded to (A) and to (Z), wherein (A) and (Z) are covalently bonded to different carbon atoms of (B), and wherein (A) and (Z) are in the trans orientation with respect to the cyclopropyl ring (B) and the other variables are as defined above in the broadest definition of the first aspect of the invention.

In one embodiment of the first aspect, the invention provides a compound of Formula I or a pharmaceutically acceptable salt or solvate thereof, wherein (B) is a cyclopropyl ring which is covalently bonded to (A) and to (Z), wherein (A) and (Z) are covalently bonded to different carbon atoms of (B), and wherein (A) and (Z) are in the trans orientation with respect to the cyclopropyl ring (B), and wherein 1 (A') group is present (X=1) and said (A') group is in the meta or para position with respect to the cyclopropyl ring and the other variables are as defined above in the broadest definition of the first aspect of the invention. Preferably the one (A') group is in the para position with respect to the cyclopropyl ring wherein said (A') group is chosen from aryl and arylalkoxy wherein said aryl or arylalkoxy group can have 0, 1, or 2 substituents independently chosen from halo, haloalkyl, aryl, arylalkoxy, alkyl, alkoxy, cyano, sulfonyl, and sulfinyl. Preferably the 0, 1, or 2 substituents on the (A') group are independently chosen from halo and haloalkyl.

In one embodiment of the first aspect of the invention, a compound of Formula I or a pharmaceutically acceptable salt or solvate thereof is provided wherein (D) is an oxygen or sulphur atom having one substituent R3 chosen from —H, alkyl, cycloalkyl, haloalkyl, and heterocyclyl, wherein said one substituent R3 has 0, 1, 2, or 3 substituents independently chosen from —NH$_2$, —N(C$_1$-C$_6$ alkyl)(C$_1$-C$_6$ alkyl), and fluoro, provided that when (D) is an oxygen R3 is not a hydrogen.

Compounds of Formula I, when (D) is a nitrogen atom have a general structure of:

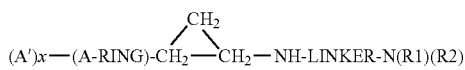

Compounds of Formula I, when (D) is an oxygen atom have a general structure of:

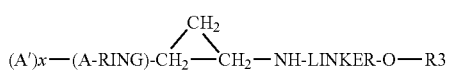

Compounds of Formula I, when (D) is a sulphur atom have a general structure of:

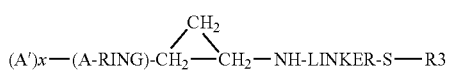

In one embodiment of the first aspect, the invention provides a compound of Formula I chosen from:
N-[2-(4-methylpiperazin-1-yl)ethyl]-N-[(trans)-2-phenylcyclopropyl]amine;
N-cyclopropyl-N'-[(trans)-2-phenylcyclopropyl]ethane-1,2-diamine;
N,N-dimethyl-N'-(2-{[(trans)-2-phenylcyclopropyl]amino}ethyl)ethane-1,2-diamine;
(3R)-1-(2-{[(trans)-2-phenylcyclopropyl]amino}ethyl)pyrrolidin-3-amine;
(3S)—N,N-dimethyl-1-(2-{[(trans)-2-phenylcyclopropyl]amino}ethyl)pyrrolidin-3-amine;
(3R)—N,N-dimethyl-1-(2-{[(trans)-2-phenylcyclopropyl]amino}ethyl)pyrrolidin-3-amine;
N-[(trans)-2-phenylcyclopropyl]-N-(2-piperazin-1-ylethyl)amine;
N1,N1-diethyl-N2-((trans)-2-phenylcyclopropyl)ethane-1,2-diamine;
N-[(trans)-2-phenylcyclopropyl]-N-(2-piperidin-1-ylethyl)amine;
(trans)-2-(4-(benzyloxy)phenyl)-N-(2-(4-methylpiperazin-1-yl)ethyl)cyclopropanamine;
(trans)-N-(2-(4-methylpiperazin-1-yl)ethyl)-2-(3'-(trifluoromethyl) biphenyl-4-yl)cyclopropanamine;
(trans)-2-(3'-chlorobiphenyl-4-yl)-N-(2-(4-methylpiperazin-1-yl)ethyl)cyclopropanamine;
(R)-1-(2-((trans)-2-(3'-(trifluoromethyl)biphenyl-4-yl)cyclopropylamino)ethyl)pyrrolidin-3-amine; and
N$^1$-cyclopropyl-N$^2$-((trans)-2-(3'-(trifluoromethyl)biphenyl-4-yl)cyclopropyl)ethane-1,2-diamine;
or a pharmaceutically acceptable salt or solvate thereof.

In one embodiment of the first aspect, the invention provides a compound of Formula I chosen from:
N-(trans)-2-(isobutylthio)ethyl-2-phenylcyclopropanamine,
N-trans-(2-ethoxyethyl)-2-phenylcyclopropanamine, and
N-trans-(2-methoxyethyl)-2-phenylcyclopropanamine;
or a pharmaceutically acceptable salt or solvate thereof.

In one embodiment of the first aspect, the invention provides a compound of Formula I chosen from:
N1-((trans)-2-(4-(3-bromobenzyloxy)phenyl)cyclopropyl)-N2-cyclopropylethane-1,2-diamine;
N1-((trans)-2-(3'-chlorobiphenyl-4-yl)cyclopropyl)-N2-cyclopropylethane-1,2-diamine;
N1-cyclopropyl-N2-((trans)-2-(4-phenethoxyphenyl)cyclopropyl)ethane-1,2-diamine;
N1,N1-diethyl-N2-((trans)-2-(4-(3-fluorobenzyloxy)phenyl)cyclopropyl)ethane-1,2-diamine;
(trans)-2-(4-bromophenyl)-N-(2-(4-methylpiperazin-1-yl)ethyl)cyclopropanamine;
N1-((trans)-2-(terphenyl-4-yl)cyclopropyl)-N2-cyclopropylethane-1,2-diamine;
(trans)-N-(2-(piperidin-1-yl)ethyl)-2-(3'-(trifluoromethyl) biphenyl-4-yl)cyclopropanamine;
N1,N1-diethyl-N2-((trans)-2-(3'-(trifluoromethyl)biphenyl-4-yl)cyclopropyl)ethane-1,2-diamine;
(trans)-N-(2-(piperazin-1-yl)ethyl)-2-(3'-(trifluoromethyl) biphenyl-4-yl)cyclopropanamine;
(S)-1-(2-((trans)-2-(3'-(trifluoromethyl)biphenyl-4-yl)cyclopropylamino)ethyl)pyrrolidin-3-amine;
(R)-1-(2-((trans)-2-(3'-chlorobiphenyl-4-yl)cyclopropylamino)ethyl)pyrrolidin-3-amine;
(R)-1-(2-((trans)-2-(4'-chlorobiphenyl-4-yl)cyclopropylamino)ethyl)pyrrolidin-3-amine;
(R)-1-(2-((trans)-2-(3'-methoxybiphenyl-4-yl)cyclopropylamino)ethyl)pyrrolidin-3-amine;
(R)-1-(2-((trans)-2-(4-(3-bromobenzyloxy)phenyl)cyclopropylamino)ethyl)pyrrolidin-3-amine; and
(R)-1-(2-((trans)-2-(6-(3-(trifluoromethyl)phenyl)pyridin-3-yl)cyclopropylamino)ethyl)pyrrolidin-3-amine;
or a pharmaceutically acceptable salt or solvate thereof.

In one embodiment of the first aspect, the invention provides a compound of Formula I chosen from:
(R)-1-(2-((trans)-2-(4-(4-bromobenzyloxy)phenyl)cyclopropylamino)ethyl)pyrrolidin-3-amine;
(R)-1-(2-((trans)-2-(4-(4-chlorobenzyloxy)phenyl)cyclopropylamino)ethyl)pyrrolidin-3-amine;
(R)-1-(2-((trans)-2-(4-(biphenyl-4-ylmethoxy)phenyl)cyclopropylamino)ethyl)pyrrolidin-3-amine;
(R)-1-(2-((trans)-2-(3',5'-dichlorobiphenyl-4-yl)cyclopropylamino)ethyl)pyrrolidin-3-amine;
N1-((trans)-2-(2-[1,1';4',1"]terphenyl-4"-yl-cyclopropyl)-N2-cyclopropylethane-1,2-diamine;
(R)-1-(2-((trans)-2-(6-(benzyloxy)-4'-(trifluoromethyl)biphenyl-3-yl)cyclopropylamino)ethyl)pyrrolidin-3-amine; and
(R)-1-(2-((trans)-2-(6-(benzyloxy)biphenyl-3-yl)cyclopropylamino)ethyl)pyrrolidin-3-amine;
or a pharmaceutically acceptable salt or solvate thereof.

In one embodiment of the first aspect, the invention provides a compound of Formula I chosen from:
(R)-1-(2-((trans)-2-(4-phenethoxyphenyl)cyclopropylamino)ethyl)pyrrolidin-3-amine;
(R)-1-(2-((trans)-2-(6-(3-methoxyphenyl)pyridin-3-yl)cyclopropylamino)ethyl)pyrrolidin-3-amine;
(R)-1-(2-((trans)-2-(6-(4-chlorophenyl)pyridin-3-yl)cyclopropylamino)ethyl)pyrrolidin-3-amine; and
4-((4-((trans)-2-(2-((R)-3-aminopyrrolidin-1-yl)ethylamino)cyclopropyl)phenoxy)methyl)benzonitrile;
or a pharmaceutically acceptable salt or solvate thereof.

In one specific embodiment of the first aspect, the invention provides a compound of Formula I:

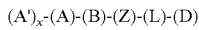

wherein:
(A) is heteroaryl or aryl covalently bonded to (B) and to (A'), if present; each (A'), if present, is independently chosen from aryl, arylalkoxy, arylalkyl, heterocyclyl, aryloxy, halo, alkoxy, haloalkyl, cycloalkyl, haloalkoxy, and cyano, wherein each (A') has 0, 1, or 2 substituents independently chosen from halo, haloalkyl, aryl, arylalkoxy, alkyl, alkoxy, cyano, sulfonyl, and sulfinyl;
X is 0, 1, 2, or 3;
(B) is a cyclopropyl ring which is covalently bonded to (A) and to (Z), wherein (A) and (Z) are covalently bonded to different carbon atoms of (B);
(Z) is —NH—; accordingly (Z) is a nitrogen atom covalently bonded to (B), to (L), and to a hydrogen atom;
(L) is a linker covalently bonded to (Z) and to (D), wherein said linker is chosen from —CH$_2$CH$_2$—, —CH$_2$CH$_2$CH$_2$—, and —CH$_2$CH$_2$CH$_2$CH$_2$—;
(D) is a nitrogen atom covalently bonded to R1, to R2, and to (L),
wherein R1 and R2 with the nitrogen (D) are taken together to form a 4, 5, or 6 membered heterocyclic ring having 0, 1, 2, or 3 substituents independently chosen from —NH$_2$, —N(C$_1$-C$_6$ alkyl)(C$_1$-C$_6$ alkyl), alkyl, halo, cyano, alkoxy, haloalkyl, and haloalkoxy;
or a pharmaceutically acceptable salt or solvate thereof.

In a related aspect, the invention provides a pharmaceutical composition comprising a compound of Formula I or a pharmaceutically acceptable salt or solvate thereof as defined above and a pharmaceutically acceptable carrier.

In a more specific embodiment, R1 and R2 with the nitrogen (D) are taken together to form a 4, 5, or 6 membered heterocyclic ring having 0, 1, 2, or 3 substituents chosen from —NH$_2$, —N(C$_1$-C$_6$ alkyl)(C$_1$-C$_6$ alkyl), and alkyl.

In a more specific aspect, the 4, 5, or 6 membered heterocyclic ring is chosen from azetidinyl, pyrrolidinyl, piperidinyl, and morpholino having 0 or 1 substituent chosen from —NH$_2$, —N(C$_1$-C$_6$ alkyl)(C$_1$-C$_6$ alkyl), and alkyl.

Preferably, the compound or pharmaceutically acceptable salt or solvate thereof of this embodiment and more specific embodiments is used for treating or preventing cancer.

In one specific embodiment of the first aspect, the invention provides a compound of Formula I or a pharmaceutically acceptable salt or solvate thereof:

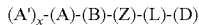

wherein:
(A) is heteroaryl or aryl covalently bonded to (B) and to (A'), if present; each (A'), if present, is independently chosen from aryl, arylalkoxy, arylalkyl, heterocyclyl, aryloxy, halo, alkoxy, haloalkyl, cycloalkyl, haloalkoxy, and cyano, wherein each (A') has 0, 1, or 2 substituents chosen from halo, haloalkyl, aryl, arylalkoxy, alkyl, alkoxy, cyano, sulfonyl, and sulfinyl;
X is 0, 1, 2, or 3;
(B) is a cyclopropyl ring which is covalently bonded to (A) and to (Z), wherein (A) and (Z) are covalently bonded to different carbon atoms of (B);
(Z) is —NH—; accordingly (Z) is a nitrogen atom covalently bonded to (B), to (L), and to a hydrogen atom;
(L) is a linker covalently bonded to (Z) and to (D), wherein said linker is chosen from —CH$_2$CH$_2$—, —CH$_2$CH$_2$CH$_2$—, and —CH$_2$CH$_2$CH$_2$CH$_2$—;
(D) is a nitrogen atom covalently bonded to R1, to R2, and to (L),
wherein R1 and R2 are independently chosen from —H, alkyl, and cycloalkyl, wherein said alkyl or cycloalkyl group has 0, 1, or 2 substituents independently chosen from —NH$_2$ and —N(C$_1$-C$_6$ alkyl)(C$_1$-C$_6$ alkyl).

In a more specific embodiment, one of R1 and R2 is an alkyl group chosen from methyl, ethyl, propyl, isopropyl, butyl, isobutyl, tert-butyl, pentyl, isopentyl, and hexyl wherein said alkyl group has 0 or 1 substituent chosen from —NH$_2$ and —N(C$_1$-C$_6$ alkyl)(C$_1$-C$_6$ alkyl).

In another specific embodiment, one of R1 and R2 is a cycloalkyl group chosen from cyclopropyl, cyclobutyl, cyclopentyl, and cyclohexyl wherein said cycloalkyl group has 0 or 1 substituent chosen from —NH$_2$ and —N(C$_1$-C$_6$ alkyl)(C$_1$-C$_6$ alkyl).

In another embodiment, the invention provides a pharmaceutical composition comprising a compound of Formula I or a pharmaceutically acceptable salt or solvate thereof as defined above and a pharmaceutically acceptable carrier.

In yet another specific embodiment of the first aspect of the invention, one of R1 and R2 is —H and the other is a cycloalkyl group having 0, 1, or 2 substituents independently chosen from —NH$_2$ and —N(C$_1$-C$_6$ alkyl)(C$_1$-C$_6$ alkyl) and the other variables are as defined above in the broadest definition of the first aspect of the invention. In a more specific embodiment, the cycloalkyl group is chosen from cyclopropyl, cyclobutyl, cyclopentyl, and cyclohexyl. In a specific aspect of this embodiment the cycloalkyl group has 0 or 1 substituent chosen from —NH$_2$ and —N(C$_1$-C$_6$ alkyl)(C$_1$-C$_6$ alkyl). In a related aspect, the compound of this embodiment or a pharmaceutically acceptable salt or solvate thereof is used for treating or preventing cancer.

In yet another specific embodiment of the first aspect, the invention provides a compound of Formula I or a pharmaceutically acceptable salt or solvate thereof:

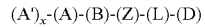

wherein:
(A) is heteroaryl or aryl covalently bonded to (B) and to (A');
(A') is chosen from aryl and arylalkoxy, wherein (A') is substituted with 0, 1, or 2 substituents independently chosen from halo and haloalkyl;
X is 1;
(B) is a cyclopropyl ring which is covalently bonded to (A) and to (Z), wherein (A) and (Z) are covalently bonded to different carbon atoms of (B);
(Z) is —NH—; accordingly (Z) is a nitrogen atom covalently bonded to (B), to (L), and to a hydrogen atom;
(L) is a linker covalently bonded to (Z) and to (D), wherein said linker is chosen from —CH$_2$CH$_2$—, —CH$_2$CH$_2$CH$_2$—, and —CH$_2$CH$_2$CH$_2$CH$_2$—;
(D) is a nitrogen atom covalently bonded to R1, to R2, and to (L);
wherein R1 and R2 are taken together with nitrogen (D) to form a 3, 4, 5, 6 or 7 membered heterocyclic ring having 0, 1, 2, or 3 substituents independently chosen from —NH$_2$, —N(C$_1$-C$_6$ alkyl)(C$_1$-C$_6$ alkyl), alkyl, halo, cyano, alkoxy, haloalkyl, and haloalkoxy, or wherein
R1 and R2 are independently chosen from —H, alkyl, cycloalkyl, haloalkyl, and heterocyclyl, wherein the sum of substituents on R1 and R2 together is 0, 1, 2, or 3 and the substituents are independently chosen from —NH$_2$, —N(C$_1$-C$_6$ alkyl)(C$_1$-C$_6$ alkyl), and fluoro, or
(D) is an oxygen or sulfur atom covalently bonded to (L) and has one substituent R3 chosen from —H, alkyl, cycloalkyl, haloalkyl, and heterocyclyl, wherein said one substituent R3 has 0, 1, 2, or 3 substituents independently chosen from —$NH_2$, —$N(C_1$-$C_6$ alkyl)($C_1$-$C_6$ alkyl), and fluoro.

In a more preferred embodiment, (A') is a phenyl group or a benzyloxy group para to the cyclopropyl ring wherein (A') has 0, 1, or 2 substituents independently chosen from halo and haloalkyl, and (D) is a nitrogen atom.

In an even more preferred embodiment, (A') is a phenyl group or a benzyloxy group para to the cyclopropyl ring wherein (A') has 0, 1, or 2 substituents independently chosen from halo and haloalkyl, (D) is a nitrogen atom, R1 is —H, and R2 is a cycloalkyl group chosen from cyclopropyl, cyclobutyl, cyclopentyl, cyclohexyl, and cycloheptyl, wherein said cycloalkyl group has 0, 1, 2, or 3 substituents independently chosen from —$NH_2$, —$N(C_1$-$C_6$ alkyl)($C_1$-$C_6$ alkyl).

In another related embodiment, the invention provides a pharmaceutical composition comprising a compound of Formula I or pharmaceutically acceptable salt or solvate as defined above in the embodiments described in this paragraph and a pharmaceutically acceptable carrier. In yet another related embodiment, the invention provides for the use of a pharmaceutical composition comprising a compound of Formula I or pharmaceutically acceptable salt or solvate as defined above in the embodiments described in this paragraph and a pharmaceutically acceptable carrier for use in treating or preventing cancer.

In another specific embodiment of the first aspect, the invention provides a compound of Formula I or a pharmaceutically acceptable salt or solvate thereof:

$$(A')_x\text{-}(A)\text{-}(B)\text{-}(Z)\text{-}(L)\text{-}(D) \qquad I$$

wherein:
(A) is phenyl covalently bonded to (B) and to (A');
(A') is a phenyl having 0 or 1 substituent chosen from aryl and arylalkoxy wherein said aryl and arylalkoxy group is substituted with 0, 1, or 2 groups independently chosen from halo and haloalkyl;
X is 1;
(B) is a cyclopropyl ring which is covalently bonded to (A) and to (Z), wherein (A) and (Z) are covalently bonded to different carbon atoms of (B),
wherein the stereochemistry around the cyclopropyl ring and the (A) and (Z) groups is trans;
(Z) is —NH—; accordingly (Z) is a nitrogen atom covalently bonded to (B), to
(L) and to a hydrogen atom;
(L) is a linker covalently bonded to (Z) and to (D), wherein said linker is chosen from —$CH_2CH_2$— and —$CH_2CH_2CH_2$—;
(D) is a nitrogen atom covalently bonded to R1, to R2, and to (L),
wherein R1 and R2 are taken together to form a 4, 5, or 6 membered heterocyclic ring having 0, 1, 2, or 3 substituents independently chosen from —$NH_2$, —$N(C_1$-$C_6$ alkyl)($C_1$-$C_6$ alkyl), and alkyl, or wherein
R1 and R2 are independently chosen from —H, alkyl, haloalkyl, and cycloalkyl wherein the sum of substituents on R1 and R2 together is 0, 1, 2, or 3 and the substituents are independently chosen from —$NH_2$, —$N(C_1$-$C_6$ alkyl)($C_1$-$C_6$ alkyl), and fluoro.

In a related aspect, the invention provides a pharmaceutical composition comprising a compound of Formula I or a pharmaceutically acceptable salt or solvate thereof as defined above and a pharmaceutically acceptable carrier.

In one embodiment of the first aspect, the invention provides a compound of Formula I or a pharmaceutically acceptable salt or solvate thereof for use in treating or preventing cancer $$(A')_x\text{-}(A)\text{-}(B)\text{-}(Z)\text{-}(L)\text{-}(D) \qquad I$$

wherein:
(A) is phenyl covalently bonded to (B) and to (A');
(A') is chosen from aryl and arylalkoxy, wherein said aryl or arylalkoxy has 0, 1, or 2 substituents independently chosen from halo and haloalkyl;
X is 1;
(B) is a cyclopropyl ring which is covalently bonded to (A) and to (Z), wherein (A) and (Z) are covalently bonded to different carbon atoms of (B) and wherein the stereochemistry around the cyclopropyl ring and the (A) and
(Z) groups is trans;
(Z) is —NH—; accordingly (Z) is a nitrogen atom covalently bonded to (B), to
(L) and to a hydrogen atom;
(L) is a linker covalently bonded to (Z) and to (D), wherein said linker is chosen from —$CH_2CH_2$— and —$CH_2CH_2CH_2$—;
(D) is a nitrogen atom covalently bonded to R1, to R2, and to (L),
wherein R1 and R2 are taken together to form a 4, 5, or 6 membered heterocyclic ring having 0, 1, 2, or 3 substituents independently chosen from —$NH_2$, —$N(C_1$-$C_6$ alkyl)($C_1$-$C_6$ alkyl), and alkyl; or wherein
R1 and R2 are independently chosen from —H, alkyl, haloalkyl, and cycloalkyl wherein the sum of substituents on R1 and R2 together is 0, 1, 2, or 3 and the substituents are independently chosen from —$NH_2$, —$N(C_1$-$C_6$ alkyl)($C_1$-$C_6$ alkyl), and fluoro.

In a related aspect, the invention provides a pharmaceutical composition for use in treating or preventing cancer, the pharmaceutical composition comprising a compound of Formula I or a pharmaceutically acceptable salt or solvate thereof as defined above in this paragraph and a pharmaceutically acceptable carrier.

In one embodiment, the invention provides a compound of Formula I or a pharmaceutically acceptable salt or solvate thereof:

$$(A')_x\text{-}(A)\text{-}(B)\text{-}(Z)\text{-}(L)\text{-}(D) \qquad I$$

wherein:
(A) is heteroaryl covalently bonded to (B) and to (A'), if present;
each (A'), if present, is covalently bonded to (A) and is independently chosen from aryl, arylalkoxy, arylalkyl, heterocyclyl, aryloxy, halo, alkoxy, haloalkyl, cycloalkyl, haloalkoxy, and cyano, wherein (A') is substituted with 0, 1, or 2 substituents independently chosen from halo, haloalkyl, aryl, arylalkoxy, alkyl, alkoxy, cyano, sulfonyl, and sulfinyl;
X is 0, 1, 2, or 3;
(B) is a cyclopropyl ring which is covalently bonded to (A) and to (Z), wherein (A) and (Z) are covalently bonded to different carbon atoms of (B);
(Z) is —NH—; accordingly (Z) is a nitrogen atom covalently bonded to (B), to (L), and to a hydrogen atom;
(L) is a linker covalently bonded to (Z) and to (D), wherein said linker is chosen from —$CH_2CH_2$—, —$CH_2CH_2CH_2$—, and —$CH_2CH_2CH_2CH_2$—;
(D) is a nitrogen atom covalently bonded to R1, to R2, and to (L),
wherein R1 and R2 are taken together with nitrogen (D) to form a heterocyclic ring having 0, 1, 2, or 3 substituents independently chosen from —NH$_2$, —N(C$_1$-C$_6$ alkyl)(C$_1$-C$_6$ alkyl), alkyl, halo, cyano, alkoxy, haloalkyl, and haloalkoxy, or wherein R1 and R2 are independently chosen from —H, alkyl, cycloalkyl, haloalkyl, and heterocyclyl, wherein the sum of substituents on R1 and R2 together is 0, 1, 2, or 3 and the substituents are independently chosen from —NH$_2$, —N(C$_1$-C$_6$ alkyl)(C$_1$-C$_6$ alkyl), and fluoro, or (D) is an oxygen or sulfur atom having one substituent R3 chosen from —H, alkyl, cycloalkyl, haloalkyl, and heterocyclyl, wherein said one substituent R3 has 0, 1, 2, or 3 substituents independently chosen from —NH$_2$, —N(C$_1$-C$_6$ alkyl)(C$_1$-C$_6$ alkyl), and fluoro;

or a pharmaceutically acceptable salt or solvate thereof.

In a related aspect, the invention provides a pharmaceutical composition comprising a compound of Formula I or a pharmaceutically acceptable salt or solvate thereof as defined above and a pharmaceutically acceptable carrier.

In a second aspect, the invention provides a compound of Formula I or a pharmaceutically acceptable salt or solvate thereof:

$$(A')_x\text{-}(A)\text{-}(B)\text{-}(Z)\text{-}(L)\text{-}(D) \qquad I$$

wherein:

(A) is heteroaryl or aryl covalently bonded to (B) and to (A'), if present; each (A'), if present, is covalently bonded to (A) and is independently chosen from aryl, arylalkoxy, arylalkyl, heterocyclyl, aryloxy, halo, alkoxy, haloalkyl, cycloalkyl, haloalkoxy, and cyano, wherein (A') is substituted with 0, 1, or 2 substituents independently chosen from halo, haloalkyl, aryl, arylalkoxy, alkyl, alkoxy, cyano, sulfonyl, and sulfinyl; X is 0, 1, 2, or 3;

(B) is a cyclopropyl ring which is covalently bonded to (A) and to (Z), wherein (A) and (Z) are covalently bonded to different carbon atoms of (B);

(Z) is —NH—; accordingly (Z) is a nitrogen atom covalently bonded to (B), to (L), and to a hydrogen atom;

(L) is a linker covalently bonded to (Z) and to (D), wherein said linker is chosen from —CH$_2$CH$_2$—, —CH$_2$CH$_2$CH$_2$—, and —CH$_2$CH$_2$CH$_2$CH$_2$—;

(D) is a nitrogen atom covalently bonded to R1, to R2, and to (L), wherein R1 and R2 are taken together with nitrogen (D) to form a heterocyclic ring having 0, 1, 2, or 3 substituents independently chosen from —NH$_2$, —N(C$_1$-C$_6$ alkyl)(C$_1$-C$_6$ alkyl), alkyl, halo, cyano, alkoxy, haloalkyl, and haloalkoxy, or wherein R1 and R2 are independently chosen from —H, alkyl, cycloalkyl, haloalkyl, and heterocyclyl, wherein the sum of substituents on R1 and R2 together is 0, 1, 2, or 3 and the substituents are independently chosen from —NH$_2$, —N(C$_1$-C$_6$ alkyl)(C$_1$-C$_6$ alkyl), and fluoro, or (D) is an oxygen or sulfur atom having one substituent R3 independently chosen from alkyl, cycloalkyl, haloalkyl, and heterocyclyl, wherein said one substituent R3 has 0, 1, 2, or 3 substituents independently chosen from —NH$_2$, —N(C$_1$-C$_6$ alkyl)(C$_1$-C$_6$ alkyl), and fluoro; or an enantiomer, diastereomer, or mixture thereof, with the proviso that the compound of formula (I) is not:

N1-[(trans)-2-phenylcyclopropyl]-N2-undecyl-rel-1,2-ethanediamine;

N1-[(trans)-2-phenylcyclopropyl]-N2-tricyclo[3.3.1.13,7]dec-2-yl-rel-1,2-ethanediamine;

N1-cyclooctyl-N2-[(trans)-2-phenylcyclopropyl]-rel-1,2-ethanediamine;

N1,N1-dimethyl-N2-(2-phenylcyclopropyl)-1,2-ethanediamine;

N,N-dimethyl-N'-(2-phenylcyclopropyl)-1,3-propanediamine;

or an enantiomer, diastereomer, or mixture thereof.

In a related aspect, the invention provides a pharmaceutical composition comprising a compound of Formula I or a pharmaceutically acceptable salt or solvate thereof as defined above and a pharmaceutically acceptable carrier. In a preferred aspect, the compound or pharmaceutically acceptable salt or solvate thereof, or pharmaceutical composition as described in this paragraph is used for treating or preventing cancer. Thus, this related aspect provides a method of treating or preventing cancer by administering to a subject/patient (preferably, a human) in need of such treatment or prevention a therapeutically effective amount of a compound or pharmaceutically acceptable salt or solvate thereof, or a pharmaceutical composition as described in this paragraph.

In one embodiment of the second aspect, the invention provides a compound of Formula I or a pharmaceutically acceptable salt or solvate thereof, wherein (A) is an aryl group and the other variables are as defined above in the broadest definition of the second aspect of the invention. In a preferred embodiment, (A) is phenyl. In another preferred embodiment, (A) is naphthy. In yet another preferred embodiment, X=1.

In one embodiment of the second aspect, the invention provides a compound of Formula I or a pharmaceutically acceptable salt or solvate thereof, wherein (A) is a phenyl group and the other variables are as defined above in the broadest definition of the second aspect of the invention. In a preferred embodiment, (A) is a phenyl group having 0, 1, 2, or 3 substituents (A') independently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, I, or 2 substituents independently chosen from halo, haloalkyl, aryl, arylalkoxy, alkyl, alkoxy, cyano, sulfonyl, and sulfinyl. In another preferred embodiment, (A) is a phenyl group having 1, 2, or 3 substituents (A') independently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, or 2 substituents independently chosen from halo, haloalkyl, aryl, arylalkoxy, alkyl, alkoxy, cyano, sulfonyl, and sulfinyl. In a related preferred embodiment, the invention relates to a method of treating or preventing cancer comprising administering to an individual (preferably, a human) a compound or a pharmaceutically acceptable salt or solvate thereof as described in this paragraph.

In one embodiment of the second aspect, the invention provides a compound of Formula I or a pharmaceutically acceptable salt or solvate thereof, wherein X is 1 or 2 and the other variables are as defined above in the broadest definition of the second aspect of the invention. In a preferred embodiment, the 1 or 2 (A') groups are independently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, or 2 substituents independently chosen from halo, haloalkyl, aryl, arylalkoxy, alkyl, alkoxy, cyano, sulfonyl, and sulfinyl. In a more preferred embodiment, the 1 or 2 (A') groups are independently chosen from aryl and arylalkoxy wherein said (A') groups have 0, 1, or 2 substituents independently chosen from halo, haloalkyl, aryl, arylalkoxy, alkyl, alkoxy, cyano, sulfonyl, and sulfinyl. In an even more preferred embodiment, the 1 or 2 (A') groups are independently chosen from phenyl, benzyloxy, and phenethyloxy, wherein said (A') has 0, 1, or 2 substituents independently chosen from halo, haloalkyl, alkyl, alkoxy, cyano, sulfonyl, and sulfinyl. In a related preferred embodiment, the invention relates to a method of treating or preventing cancer comprising administering to an individual (preferably, a human) a compound or a pharmaceutically acceptable salt or solvate thereof as described in this paragraph.

In one embodiment of the second aspect, the invention provides a compound of Formula I or a pharmaceutically acceptable salt or solvate thereof, wherein X is 1; and (A') is chosen from aryl and arylalkoxy, wherein said aryl or arylalkoxy has 0, 1, or 2 substituents independently chosen from halo and haloalkyl and the other variables are as defined above in the broadest definition of the second aspect of the invention. In a preferred embodiment, (A') is a phenyl group or a benzyloxy group having 0, 1, or 2 substituents independently chosen from halo and haloalkyl. In a related preferred embodiment, the invention relates to a method of treating or preventing cancer comprising administering to an individual (preferably, a human) a compound or a pharmaceutically acceptable salt or solvate thereof as described in this paragraph.

In one embodiment of the second aspect, the invention provides a compound of Formula I, wherein R1 and R2 are taken together with nitrogen (D) to give a 4, 5, 6, 7, 8, or 9 membered heterocyclic ring having 0, 1, 2, or 3 substituents independently chosen from —$NH_2$, —$N(C_1$-$C_6$ alkyl)($C_1$-$C_6$ alkyl), alkyl, halo, cyano, alkoxy, haloalkyl, and haloalkoxy and the other variables are as defined above in the broadest definition of the second aspect of the invention. In a preferred embodiment, the 4, 5, 6, 7, 8, or 9 membered heterocyclic ring is not fully aromatic and has 0, 1, 2, or 3 substituents independently chosen from —$NH_2$, —$N(C_1$-$C_6$ alkyl)($C_1$-$C_6$ alkyl), alkyl, halo, cyano, alkoxy, haloalkyl, and haloalkoxy. In a more preferred embodiment, the 4, 5, 6, 7, 8, or 9 membered heterocyclic ring is chosen from pyrrolidinyl, imidazolidinyl, pyrazolidinyl, piperidinyl, morpholino, and homopiperidinyl wherein said 4, 5, 6, 7, 8, or 9 membered heterocyclic ring has 0, 1, 2 or 3 substituents independently chosen from —$NH_2$, —$N(C_1$-$C_6$ alkyl)($C_1$-$C_6$ alkyl), alkyl, halo, cyano, alkoxy, haloalkyl, and haloalkoxy. In a related preferred embodiment, the invention relates to a method of treating or preventing cancer comprising administering to an individual (preferably, a human) a compound or a pharmaceutically acceptable salt or solvate thereof as described in this paragraph.

In one embodiment of the second aspect, the invention provides a compound of Formula I or a pharmaceutically acceptable salt or solvate thereof, wherein R1 and R2 are independently chosen from —H, alkyl, cycloalkyl, and haloalkyl wherein the sum of substituents on R1 and R2 together are 0, 1, 2, or 3 and the substituents are independently chosen from —$NH_2$, —$N(C_1$-$C_6$ alkyl)($C_1$-$C_6$ alkyl), and fluoro and the other variables are as defined above in the broadest definition of the second aspect of the invention. In a related preferred embodiment, the invention relates to a method of treating or preventing cancer comprising administering to an individual (preferably, a human) a compound or pharmaceutically acceptable salt or solvate thereof as described in this paragraph.

In one embodiment of the second aspect, the invention provides a compound of Formula I or a pharmaceutically acceptable salt or solvate thereof, wherein R1 is —H and R2 is chosen from a 3, 4, 5, 6, or 7 membered cycloalkyl group having 0 or 1 substituent chosen from —$NH_2$ and —$N(C_1$-$C_6$ alkyl)($C_1$-$C_6$ alkyl) and the other variables are as defined above in the broadest definition of the second aspect of the invention. In a preferred embodiment, R1 is —H and R2 is a cyclopropyl group. In another preferred aspect, R1 is —H and R2 is a cyclobutyl group. In another preferred aspect, R1 is —H and R2 is a cyclopentyl group. In another preferred aspect, R1 is —H and R2 is a cyclohexyl group. Preferred substituents on the cycloalkyl group of this embodiment are —$NH_2$, dimethyl amino, and/or diethylamino. In a related preferred embodiment, the invention relates to a method of treating or preventing cancer comprising administering to an individual (preferably, a human) a compound or a pharmaceutically acceptable salt or solvate thereof as described in this paragraph.

In one embodiment of the second aspect, the invention provides a compound of Formula I or a pharmaceutically acceptable salt or solvate thereof, wherein (D) is a nitrogen atom and wherein R1 and R2 are independently chosen from —H, $C_3$-$C_7$ cycloalkyl, $C_2$-$C_{10}$ alkyl, haloalkyl, and heterocyclyl, wherein the sum of substituents on R1 and R2 together is 0, 1, 2, or 3 and the substituents are independently chosen from —$NH_2$, —$N(C_1$-$C_6$ alkyl)($C_1$-$C_6$ alkyl), and fluoro and the other variables are as defined above in the broadest definition of the second aspect of the invention. In a preferred aspect of this embodiment, R1 is —H and R2 is chosen from $C_3$-$C_7$ cycloalkyl, $C_2$-$C_8$ alkyl, haloalkyl, and heterocyclyl wherein said R2 has 0, 1, 2, or 3 substituents independently chosen from —$NH_2$, and —$N(C_1$-$C_6$ alkyl)($C_1$-$C_6$ alkyl). In a related preferred embodiment, the invention relates to a method of treating or preventing cancer comprising administering to an individual (preferably, a human) a compound or a pharmaceutically acceptable salt or solvate thereof as described in this paragraph.

In one embodiment of the second aspect, the invention provides a compound of Formula I or a pharmaceutically acceptable salt or solvate thereof, wherein R1 and R2 are taken together with nitrogen (D) to give a heterocyclic ring chosen from azetidinyl, pyrrolidinyl, piperidinyl, and morpholino wherein said heterocyclic ring has 0 or 1 substituent chosen from —$NH_2$, —$N(C_1$-$C_6$ alkyl)($C_1$-$C_6$ alkyl), alkyl, halo, cyano, alkoxy, haloalkyl, and haloalkoxy and the other variables are as defined above in the broadest definition of the second aspect of the invention. In a preferred embodiment, (L) is chosen from —$CH_2CH_2$— and —$CH_2CH_2CH_2$—. In another preferred embodiment, (L) is chosen from —$CH_2$— and —$CH_2CH_2$—, (A) is a phenyl group substituted by an (A') group chosen from phenyl or arylalkoxy wherein said (A') phenyl or (A') arylalkoxy group has 0, 1, or 2 substituents independently chosen from halo, haloalkyl, alkyl, alkoxy, cyano, sulfonyl, and sulfinyl. In a related preferred embodiment, the invention relates to a method of treating or preventing cancer comprising administering to an individual (preferably, a human) a compound or a pharmaceutically acceptable salt or solvate thereof as described in this paragraph.

In one embodiment of the second aspect, the invention provides a compound of Formula I or a pharmaceutically acceptable salt or solvate thereof, wherein (A) is a heteroaryl and the other variables are as defined above in the broadest definition of the second aspect of the invention. In a preferred aspect, (A) is a heteroaryl chosen from pyridyl, pyrimidinyl, and thiophenyl. In a related preferred embodiment, the invention relates to a method of treating or preventing cancer comprising administering to an individual (preferably, a human) a compound or a pharmaceutically acceptable salt or solvate thereof as described in this paragraph.

In one embodiment of the second aspect, the invention provides a compound of Formula I or a pharmaceutically acceptable salt or solvate thereof, wherein (A) is a heteroaryl chosen from pyridyl, pyrimidinyl, and thiophenyl and the other variables are as defined above in the broadest definition of the second aspect of the invention. In a preferred aspect of this embodiment, X is 0 or 1. In another preferred aspect X is 0 or 1 and (A') is an aryl or arylalkoxy group wherein said (A') group, if present, has from 0, 1, or 2 substituents independently chosen from halo, haloalkyl, alkyl, alkoxy, cyano, sulfonyl, and sulfinyl. In a related preferred embodiment, the invention relates to a method of treating or preventing cancer comprising administering to an individual (preferably, a human) a compound or a pharmaceutically acceptable salt or solvate thereof as described in this paragraph.

In one embodiment of the second aspect, the invention provides a compound of Formula I or a pharmaceutically acceptable salt or solvate thereof, wherein (L) is a linker chosen from —$CH_2CH_2$— and —$CH_2CH_2CH_2$— and the other variables are as defined above in the broadest definition of the second aspect of the invention. In one more preferred embodiment, X=1. In another preferred embodiment, (D) is a nitrogen atom and R1 and R2 are taken together to form a heterocyclic ring having 0 or 1 substituent chosen from —$NH_2$, and —$N(C_1\text{-}C_6 \text{ alkyl})(C_1\text{-}C_6 \text{ alkyl})$. In a related preferred embodiment, the invention relates to a method of treating or preventing cancer comprising administering to an individual a compound or a pharmaceutically acceptable salt or solvate thereof as described in this paragraph.

In one embodiment of the second aspect, the invention provides a compound of Formula I or a pharmaceutically acceptable salt or solvate thereof, wherein (L) is —$CH_2CH_2$— and the other variables are as defined above in the broadest definition of the second aspect of the invention. In one more preferred embodiment, X=1. In another preferred embodiment, (D) is a nitrogen atom and R1 and R2 are taken together to form a heterocyclic ring having 0 or 1 substituent chosen from —$NH_2$, and —$N(C_1\text{-}C_6 \text{ alkyl})(C_1\text{-}C_6 \text{ alkyl})$. In a related preferred embodiment, the invention relates to a method of treating or preventing cancer comprising administering to an individual (preferably, a human) a compound or a pharmaceutically acceptable salt or solvate thereof as described in this paragraph.

In one embodiment of the second aspect, the invention provides a compound of Formula I or a pharmaceutically acceptable salt or solvate thereof, wherein (B) is a cyclopropyl ring which is covalently bonded to (A) and to (Z), wherein (A) and (Z) are covalently bonded to different carbon atoms of (B), and wherein (A) and (Z) are in the trans orientation with respect to the cyclopropyl ring (B) and the other variables are as defined above in the broadest definition of the second aspect of the invention. In a more preferred embodiment, X=1, 2, or 3. In a related preferred embodiment, the invention relates to a method of treating or preventing cancer comprising administering to an individual (preferably, a human) a compound or a pharmaceutically acceptable salt or solvate thereof as described in this paragraph.

In one embodiment of the second aspect, the invention provides a compound of Formula I or a pharmaceutically acceptable salt or solvate thereof, wherein (B) is a cyclopropyl ring which is covalently bonded to (A) and to (Z), wherein (A) and (Z) are covalently bonded to different carbon atoms of (B), and wherein (A) and (Z) are in the trans orientation with respect to the cyclopropyl ring (B), and wherein 1 (A') group is present (X=1) and said (A') group is in the meta or para position with respect to the cyclopropyl ring and the other variables are as defined above in the broadest definition of the second aspect of the invention. Preferably the one (A') group is in the para position with respect to the cyclopropyl ring wherein said (A') group is chosen from aryl and arylalkoxy wherein said aryl or arylalkoxy group can have from 0, 1, or 2 substituents chosen from halo, haloalkyl, aryl, arylalkoxy, alkyl, alkoxy, cyano, sulfonyl, and sulfinyl. Preferably the 0, 1, or 2 substituents on (A') are chosen from halo and haloalkyl. In a related preferred embodiment, the invention relates to a method of treating or preventing cancer comprising administering to an individual (preferably, a human) a compound or a pharmaceutically acceptable salt or solvate thereof as described in this paragraph.

In a third aspect, the invention provides a method of treating or preventing a disease or condition comprising administering, to a subject/patient (preferably, a human) in need of treatment or prevention, a therapeutically effective amount of a composition comprising a compound of Formula I or a pharmaceutically acceptable salt or solvate thereof, and a pharmaceutically acceptable carrier, wherein the compound of Formula I is defined above in the first or second aspect of the invention or embodiment thereof. This aspect can be reformulated as a compound of Formula I or a pharmaceutically acceptable salt or solvate thereof for use as a medicine.

In a fourth aspect, the invention provides a method of inhibiting LSD1 activity comprising administering, to a subject/patient (preferably, a human) in need of treatment, an amount of a composition comprising a compound of Formula I' or a pharmaceutically acceptable salt or solvate thereof:

$$(A')_x\text{-}(A)\text{-}(B)\text{-}(Z)\text{-}(L)\text{-}(D) \quad\quad\quad I'$$

wherein:

(A) is heteroaryl or aryl covalently bonded to (B) and to (A'), if present; each (A'), if present, is independently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, or 2 substituents independently chosen from halo, haloalkyl, aryl, arylalkoxy, alkyl, alkoxy, cyano, sulfonyl, and sulfinyl;

X is 0, 1, 2, or 3;

(B) is a cyclopropyl ring which is covalently bonded to (A) and to (Z), wherein (A) and (Z) are covalently bonded to different carbon atoms of (B);

(Z) is —NH—; accordingly, (Z) is a nitrogen atom covalently bonded to (B), to (L), and to a hydrogen atom;

(L) is a linker covalently bonded to (Z) and to (D), wherein said linker is chosen from —$CH_2CH_2$—, —$CH_2CH_2CH_2$—, and —$CH_2CH_2CH_2CH_2$—;

(D) is a nitrogen atom covalently bonded to R1, to R2, and to (L);

wherein R1 and R2 are taken together with nitrogen (D) to form a heterocyclic ring having 0, 1, 2, or 3 substituents independently chosen from —$NH_2$, —$N(C_1\text{-}C_6 \text{ alkyl})(C_1\text{-}C_6 \text{ alkyl})$, alkyl, halo, cyano, alkoxy, haloalkyl, and haloalkoxy, or wherein R1 and R2 are independently chosen from —H, alkyl, cycloalkyl, haloalkyl, and heterocyclyl, wherein the sum of substituents on R1 and R2 together is 0, 1, 2, or 3 and the substituents are independently chosen from —$NH_2$, —$N(C_1\text{-}C_6 \text{ alkyl})(C_1\text{-}C_6 \text{ alkyl})$, and fluoro, or (D) is an oxygen or sulfur atom covalently bound to (L), wherein said (D) group has one substituent R3 chosen from —H, alkyl, cycloalkyl, haloalkyl, and heterocyclyl, wherein said one substituent R3 has 0, 1, 2, or 3 substituents independently chosen from —$NH_2$, —$N(C_1\text{-}C_6 \text{ alkyl})(C_1\text{-}C_6 \text{ alkyl})$, and fluoro; and a pharmaceutically acceptable carrier sufficient to inhibit LSD1 activity. This aspect can be reformulated as a compound of Formula I' or a pharmaceutically acceptable salt or solvate thereof as herein defined for use as an LSD1 inhibitor. This aspect can also be reformulated as a compound of Formula I' or a pharmaceutically acceptable salt or solvate thereof, for use in the treatment or prevention of a disease associated with LSD1.

In a fifth aspect, the invention provides a method of treating or preventing cancer comprising administering, to a subject/patient (preferably, a human) in need of treatment or prevention, a therapeutically effective amount of a composition comprising a compound of Formula I' which is an LSD1 inhibitor as defined above in the fourth aspect of the invention or a pharmaceutically acceptable salt or solvate thereof, and a pharmaceutically acceptable carrier. This aspect can be reformulated as a compound of Formula I' which is an LSD1 inhibitor as defined above in the fourth aspect of the invention or a pharmaceutically acceptable salt or solvate thereof, for use in treating or preventing cancer. Preferably, the cancer is chosen from breast cancer, colorectal cancer, lung cancer, prostate cancer, skin cancer, testicular cancer, blood cancer, and brain cancer.

In a sixth aspect, the invention provides a method of treating or preventing cancer comprising administering, to a subject/patient (preferably, a human) in need of treatment or prevention, a therapeutically effective amount of a composition comprising a compound of Formula I as defined above in said first or second aspect of the invention and their respective embodiments or a pharmaceutically acceptable salt or solvate thereof, and a pharmaceutically acceptable carrier. This aspect can be reformulated as a compound of Formula I as defined above in said first or second aspect of the invention and their respective subembodiments or a pharmaceutically acceptable salt or solvate thereof, for use in treating or preventing cancer. Preferably, the cancer is chosen from breast cancer, colorectal cancer, lung cancer, prostate cancer, skin cancer, testicular cancer, blood cancer, and brain cancer. In one preferred embodiment, the invention provides a method of treating or preventing breast cancer comprising administering, to a subject/patient (preferably, a human) in need of treatment or prevention, a therapeutically effective amount of a composition comprising a compound of Formula I as defined above in said first or second aspect of the invention and their respective embodiments or a pharmaceutically acceptable salt or solvate thereof, and a pharmaceutically acceptable carrier. In one preferred embodiment, the invention provides a method of treating or preventing prostate cancer comprising administering, to a subject/patient (preferably, a human) in need of treatment or prevention, a therapeutically effective amount of a composition comprising a compound of Formula I as defined above in said first or second aspect of the invention and their respective embodiments or a pharmaceutically acceptable salt or solvate thereof, and a pharmaceutically acceptable carrier. In one preferred embodiment, the invention provides a method of treating or preventing colorectal cancer comprising administering, to a subject/patient (preferably, a human) in need of treatment or prevention, a therapeutically effective amount of a composition comprising a compound of Formula I as defined above in said first or second aspect of the invention and their respective embodiments or a pharmaceutically acceptable salt or solvate thereof, and a pharmaceutically acceptable carrier. In one preferred embodiment, the invention provides a method of treating or preventing brain cancer comprising administering, to a subject/patient (preferably, a human) in need of treatment or prevention, a therapeutically effective amount of a composition comprising a compound of Formula I as defined above in said first or second aspect of the invention and their respective embodiments or a pharmaceutically acceptable salt or solvate thereof, and a pharmaceutically acceptable carrier. In one preferred embodiment, the invention provides a method of treating or preventing lung cancer comprising administering, to a subject/patient (preferably, a human) in need of treatment or prevention, a therapeutically effective amount of a composition comprising a compound of Formula I as defined above in said first or second aspect of the invention and their respective embodiments or a pharmaceutically acceptable salt or solvate thereof, and a pharmaceutically acceptable carrier.

In another aspect, the invention provides a pharmaceutical composition comprising a pharmaceutically acceptable carrier and a compound of Formula I which is a selective inhibitor of LSD1 as defined in the first or second aspect of the invention and their respective embodiments or a pharmaceutically acceptable salt or solvate thereof. LSD1 selective inhibitors have Ki values for LSD1 which are at least 2-fold lower than the Ki value for MAO-A and/or MAO-B. In one embodiment of this aspect, the LSD1 Ki value is at least 5-fold lower than the Ki value for MAO-A and/or MAO-B. In one aspect of this embodiment, the LSD1 Ki value is at least 10-fold lower than the Ki value for MAO-A and MAO-B. In one embodiment of this aspect, the pharmaceutical composition comprising a LSD1 selective inhibitor of Formula I or a pharmaceutically acceptable salt or solvate thereof is useful for treating or preventing a disease in an individual (preferably, a human). In a more specific aspect, the disease is cancer. In an even more specific aspect, the disease is a cancer chosen from prostate, brain, colorectal, lung, breast, skin, testicular, and blood cancer. In one specific aspect, the cancer is prostate cancer. In one specific aspect, the cancer is lung cancer. In one specific aspect, the cancer is brain cancer. In one specific aspect, the cancer is blood cancer (e.g., leukemia). In one specific aspect, the cancer is breast cancer. In one specific aspect, the cancer is colorectal cancer. In one specific aspect, the cancer is testicular cancer. In one specific aspect, the cancer is skin cancer.

In some aspects and embodiments of the invention, the compounds of the invention of Formula I do not include:
N1-[(trans)-2-phenylcyclopropyl]-N2-undecyl-rel-1,2-ethanediamine (corresponding to CAS reg. no. 627525-03-5);
N1-[(trans)-2-phenylcyclopropyl]-N2-tricyclo[3.3.1.13,7]dec-2-yl-rel-1,2-ethanediamine (corresponding to CAS reg. no. 627519-38-4);
N1-cyclooctyl-N2-[(trans)-2-phenylcyclopropyl]-rel-1,2-ethanediamine (corresponding to CAS reg. no. 627519-36-2);
N1,N1-dimethyl-N2-(2-phenylcyclopropyl)-1,2-ethanediamine (corresponding to CAS reg. no. 106572-06-9);
N,N-dimethyl-N'-(2-phenylcyclopropyl)-1,3-propanediamine (corresponding to CAS reg. no. 100407-49-6); and
trans-1-phenyl-2-[(2-hydroxyethyl)amino]cyclopropane (corresponding to CAS reg. no. 32752-04-8);
or an enantiomer, diastereomer, or mixture thereof.

In one specific aspect, the invention provides a compound of Formula I:

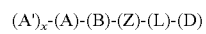

$$(A')_x\text{-}(A)\text{-}(B)\text{-}(Z)\text{-}(L)\text{-}(D) \qquad I$$

or an enantiomer, diastereomer, or mixture thereof, or a pharmaceutically acceptable salt or solvate thereof, wherein (A'), X, (A), (B), (Z), (L) and (D) have the meanings or preferred meanings defined in the following.

(A) is heteroaryl or aryl.

Said aryl is preferably phenyl or naphthyl. More preferably, said aryl is phenyl.

Said heteroaryl is preferably chosen from thienyl (thiophenyl), benzo[b]thienyl, naphtho[2,3-b]thienyl, thianthrenyl, furyl (furanyl), isobenzofuranyl, chromenyl, xanthenyl, phenoxanthiinyl, pyrrolyl, including without limitation 2H-pyrrolyl, imidazolyl, pyrazolyl, pyridyl (pyridinyl), including without limitation 2-pyridyl, 3-pyridyl, and 4-pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, beta-carbolinyl, phenanthridinyl, acrindinyl, perimidinyl, phenanthrolinyl, phenazinyl, isothiazolyl, phenothiazinyl, isoxazolyl, furazanyl, phenoxazinyl, isocoumarin, pyrido[1,2-a]pyrimidin-4-one, pyrazolo[1,5-a]pyrimidinyl, including without limitation pyrazolo[1,5-a]pyrimidin-3-yl, 1,2-benzoisoxazol-3-yl, benzimidazolyl, 2-oxindolyl, and 2-oxobenzimidazolyl. More preferably, said heteroaryl is chosen from pyridyl, pyrimidinyl, and thiophenyl.

Preferably, (A) is aryl. More preferably, (A) is phenyl or naphthyl. Even more preferably, (A) is phenyl.

Each (A'), if present, is independently chosen from aryl, arylalkoxy, arylalkyl, heterocyclyl, aryloxy, halo, alkoxy, haloalkyl, cycloalkyl, haloalkoxy, and cyano; preferably, each (A'), if present, is independently chosen from aryl and arylalkoxy; more preferably, each (A'), if present, is independently chosen from phenyl, benzyloxy, and phenethyloxy; even more preferably, each (A'), if present, is independently chosen from phenyl and benzyloxy.

Furthermore, each (A') is substituted with 0, 1, 2 or 3 substituents (preferably, 0, 1, or 2 substituents; more preferably, 0 or 1 substituent) independently chosen from halo, haloalkyl, aryl, arylalkoxy, alkyl, alkoxy, cyano, sulfonyl, amido, and sulfinyl. Preferably, said substituents are independently chosen from halo, haloalkyl, aryl, arylalkoxy, alkyl, alkoxy, cyano, sulfonyl, and sulfinyl. More preferably, said substituents are independently chosen from halo and haloalkyl.

Accordingly, it is particularly preferred that each (A'), if present, is independently chosen from aryl and arylalkoxy (in particular, from phenyl, benzyloxy, and phenethyloxy), wherein said aryl or arylalkoxy (or, accordingly, said phenyl, said benzyloxy, or said phenethyloxy) is substituted with 0 or 1 substituent chosen from halo, haloalkyl, aryl, arylalkoxy, alkyl, alkoxy, cyano, sulfonyl, amido, and sulfinyl (in particular, from halo and haloalkyl).

X is 0, 1, 2, or 3.

Preferably, X is 1, 2, or 3. More preferably, X is 1 or 2. Even more preferably, X is 1.

It is particularly preferred that X is 1 and the one (A') group is in the meta or in the para position with respect to the cyclopropyl ring (B). It is even more preferred that X is 1 and the one (A') group is in the para position with respect to the cyclopropyl ring (B).

(B) is a cyclopropyl ring, wherein (A) and (Z) are covalently bonded to different carbon atoms of (B).

It is preferred that (A) and (Z) are in the trans orientation with respect to the cyclopropyl ring (B).

(Z) is —NH—.

(L) is chosen from —CH$_2$CH$_2$—, —CH$_2$CH$_2$CH$_2$—, and —CH$_2$CH$_2$CH$_2$CH$_2$—.

Preferably, (L) is chosen from —CH$_2$CH$_2$— and —CH$_2$CH$_2$CH$_2$—. More preferably, (L) is —CH$_2$CH$_2$—.

(D) is chosen from —N(—R1)-R2, —O—R3, and —S—R3.

Preferably, (D) is —N(—R1)-R2.

In one embodiment of this specific aspect, R1 and R2 are mutually linked to form a heterocyclic ring together with the nitrogen atom that R1 and R2 are attached to. Said heterocyclic ring has 0, 1, 2, or 3 substituents (preferably, 0, 1, or 2 substituents; more preferably, 0 or 1 substituent) independently chosen from —NH$_2$, —NH(C$_1$-C$_6$ alkyl), —N(C$_1$-C$_6$ alkyl)(C$_1$-C$_6$ alkyl), alkyl, halo, cyano, alkoxy, haloalkyl, and haloalkoxy.

Preferably, said heterocyclic ring is a 4, 5, 6, 7, 8, or 9 membered heterocyclic ring (i.e., a heterocyclic ring having 4, 5, 6, 7, 8, or 9 ring atoms), which is preferably aliphatic and more preferably saturated. More preferably, said heterocyclic ring is a 4, 5, or 6 membered heterocyclic ring (i.e., a heterocyclic ring having 4, 5, or 6 ring atoms), which is preferably aliphatic and more preferably saturated. Even more preferably, said heterocyclic ring is chosen from azetidinyl, pyrrolidinyl, imidazolidinyl, pyrazolidinyl, piperidinyl, morpholino, and homopiperidinyl (i.e., azepanyl). Yet even more preferably, said heterocyclic ring is chosen from azetidinyl, pyrrolidinyl, piperidinyl, and morpholino.

Preferably, said substituent(s) on the heterocyclic ring are/is independently chosen from —NH$_2$, —N(C$_1$-C$_6$ alkyl)(C$_1$-C$_6$ alkyl), alkyl, halo, cyano, alkoxy, haloalkyl, and haloalkoxy. Preferably, said substituent(s) on the heterocyclic ring are/is independently chosen from —NH$_2$, —N(C$_1$-C$_6$ alkyl)(C$_1$-C$_6$ alkyl), and alkyl.

Accordingly, it is particularly preferred that said heterocyclic ring is chosen from azetidinyl, pyrrolidinyl, imidazolidinyl, pyrazolidinyl, piperidinyl, morpholino, and homopiperidinyl (in particular, from azetidinyl, pyrrolidinyl, piperidinyl, and morpholino) and that said heterocyclic ring has 0 or 1 substituent chosen from —NH$_2$, —N(C$_1$-C$_6$ alkyl)(C$_1$-C$_6$ alkyl), alkyl, halo, cyano, alkoxy, haloalkyl, and haloalkoxy. It is even more preferred that said heterocyclic ring is chosen from azetidinyl, pyrrolidinyl, imidazolidinyl, pyrazolidinyl, piperidinyl, morpholino, and homopiperidinyl (in particular, from azetidinyl, pyrrolidinyl, piperidinyl, and morpholino) and that said heterocyclic ring has 0 or 1 substituent chosen from —NH$_2$, —N(C$_1$-C$_6$ alkyl)(C$_1$-C$_6$ alkyl), and alkyl.

In another embodiment of this specific aspect, R1 and R2 are independently chosen from —H, alkyl, cycloalkyl, haloalkyl, and heterocyclyl, wherein the sum of substituents on R1 and R2 together is 0, 1, 2, or 3 (preferably, the sum of substituents on R1 and R2 together is 0, 1, or 2; more preferably, the sum of substituents on R1 and R2 together is 0 or 1) and the substituents are independently chosen from —NH$_2$, —NH(C$_1$-C$_6$ alkyl), —N(C$_1$-C$_6$ alkyl)(C$_1$-C$_6$ alkyl), and fluoro.

Preferably, R1 and R2 are independently chosen from —H, alkyl (e.g., a C$_2$-C$_8$ alkyl), cycloalkyl (e.g., a C$_3$-C$_7$ cycloalkyl), and haloalkyl. More preferably, R1 and R2 are independently chosen from —H, alkyl (e.g., a C$_2$-C$_8$ alkyl), and cycloalkyl (e.g., a C$_3$-C$_7$ cycloalkyl).

Preferably, said substituents on R1 and/or R2 are independently chosen from —NH$_2$, —N(C$_1$-C$_6$ alkyl)(C$_1$-C$_6$ alkyl), and fluoro. More preferably, said substituents on R1 and/or R2 are independently chosen from —NH$_2$ and —N(C$_1$-C$_6$ alkyl)(C$_1$-C$_6$ alkyl).

Accordingly, it is preferred that, in this embodiment of the present specific aspect, R1 and R2 are independently chosen from —H, alkyl, cycloalkyl, and haloalkyl (in particular, from —H, alkyl, and cycloalkyl) and that the sum of substituents on R1 and R2 together is 0 or 1, wherein the 0 or 1 substituent on R1 or R2 is chosen from —NH$_2$, —N(C$_1$-C$_6$ alkyl)(C$_1$-C$_6$ alkyl), and fluoro (in particular, from —NH$_2$ and —N(C$_1$-C$_6$ alkyl)(C$_1$-C$_6$ alkyl)).

Furthermore, it is particularly preferred that R2 is a cycloalkyl group chosen from cyclopropyl, cyclobutyl, cyclopentyl, cyclohexyl, and cycloheptyl (preferably chosen from cyclopropyl, cyclobutyl, cyclopentyl, and cyclohexyl), wherein said cycloalkyl group has 0 or 1 substituent chosen from —NH$_2$ and —N(C$_1$-C$_6$ alkyl)(C$_1$-C$_6$ alkyl). Said 0 or 1 substituent is preferably chosen from —NH$_2$, dimethylamino, and diethylamino. It is even more preferred that R1 is —H and R2 is a cycloalkyl group chosen from cyclopropyl, cyclobutyl, cyclopentyl, cyclohexyl, and cycloheptyl (preferably chosen from cyclopropyl, cyclobutyl, cyclopentyl, and cyclohexyl), wherein said cycloalkyl group has 0 or 1 substituent chosen from —NH$_2$ and —N(C$_1$-C$_6$ alkyl)(C$_1$-C$_6$ alkyl) or, more preferably, chosen from —NH$_2$, dimethylamino, and diethylamino.

R3 is chosen from —H, alkyl, cycloalkyl, haloalkyl, and heterocyclyl, wherein R3 has 0, 1, 2, or 3 substituents (preferably, 0, 1, or 2 substituents; more preferably, 0 or 1 substituent) independently chosen from —NH$_2$, —NH(C$_1$-C$_6$ alkyl), —N(C$_1$-C$_6$ alkyl)(C$_1$-C$_6$ alkyl), and fluoro.

Preferably, R3 is chosen from —H, alkyl, cycloalkyl, and haloalkyl. More preferably, R3 is chosen from alkyl, cycloalkyl, and haloalkyl.

Preferably, said substituent(s) on R3 are/is independently chosen from —NH$_2$, —N(C$_1$-C$_6$ alkyl)(C$_1$-C$_6$ alkyl), and fluoro.

Accordingly, it is particularly preferred that R3 is chosen from alkyl, cycloalkyl, and haloalkyl, wherein R3 has 0 or 1 substituent chosen from —NH$_2$, —N(C$_1$-C$_6$ alkyl)(C$_1$-C$_6$ alkyl), and fluoro.

In this specific aspect, the following compounds are excluded:
N1-[(trans)-2-phenylcyclopropyl]-N2-undecyl-rel-1,2-ethanediamine;
N1-[(trans)-2-phenylcyclopropyl]-N2-tricyclo[3.3.1.13,7] dec-2-yl-rel-1,2-ethanediamine;
N1-cyclooctyl-N2-[(trans)-2-phenylcyclopropyl]-rel-1,2-ethanediamine;
N1,N1-dimethyl-N2-(2-phenylcyclopropyl)-1,3-propanediamine;
N1,N1-dimethyl-N2-(2-phenylcyclopropyl)-1,2-ethanediamine; and
trans-1-phenyl-2-[(2-hydroxyethyl)amino]cyclopropane.

In accordance with this specific aspect, the invention provides a compound of Formula I or an enantiomer, diastereomer, or mixture thereof, or a pharmaceutically acceptable salt or solvate thereof, as described and defined herein above, for use as a medicament. Accordingly, the invention provides a pharmaceutical composition comprising a pharmaceutically acceptable carrier and a compound of Formula I or a pharmaceutically acceptable salt or solvate thereof, as described and defined herein above. Also, the invention provides a method of treating or preventing a disease or condition comprising administering, to a subject/patient (preferably, a human) in need of treatment or prevention, a therapeutically effective amount of a compound of Formula I or a pharmaceutically acceptable salt or solvate thereof, as described and defined herein above, or a pharmaceutical composition comprising a pharmaceutically acceptable carrier and said compound of Formula I or a pharmaceutically acceptable salt or solvate thereof. Moreover, the invention provides a compound of Formula I or a pharmaceutically acceptable salt or solvate thereof, as described and defined herein above, or a pharmaceutical composition comprising a pharmaceutically acceptable carrier and said compound of Formula I or a pharmaceutically acceptable salt or solvate thereof, for use in treating or preventing cancer. Accordingly, the invention provides a method of treating or preventing cancer comprising administering, to a subject/patient (preferably, a human) in need of treatment or prevention (i.e., of such treatment or prevention), a therapeutically effective amount of a compound of Formula I or a pharmaceutically acceptable salt or solvate thereof, as described and defined herein above, or a pharmaceutical composition comprising a pharmaceutically acceptable carrier and said compound of Formula I or a pharmaceutically acceptable salt or solvate thereof. The cancer to be treated or prevented in accordance with the invention is preferably chosen from breast cancer, colorectal cancer, lung cancer, prostate cancer, skin cancer, testicular cancer, blood cancer, and brain cancer.

It is to be understood that, if a group is defined to have 0 substituents (or to be substituted with 0 substituents) selected from a number of substituents, then the respective group is not substituted with any substituent from this number of substituents but instead is substituted with hydrogen.

It is further to be understood that hydrogen (or a group —H) cannot be substituted. Accordingly, when a number of different groups, including hydrogen, are stated to have n substituents (e.g., 0, 1, or 2 substituents), then the hydrogen always has 0 substituents.

DEFINITIONS

As used herein, the term "alkyl" refers to a saturated aliphatic hydrocarbon, including straight chain and/or branched chain groups, having from 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc. up to and including 20 carbon atoms). Preferably, the "alkyl" has from 1 to 10 carbon atoms. More preferably, the "alkyl" or "lower alkyl" has from 1 to 6 carbon atoms, and even more preferably 1 to 4 carbon atoms.

As used herein, the term "halo" refers to chloro, fluoro, bromo, and iodo.

As used herein, the term "hydro" refers to a hydrogen atom (—H group).

As used herein, the term "alkoxy" refers to an —O-alkyl group, wherein "alkyl" has the meaning provided above. "Lower alkoxy" refers to —O-lower alkyl groups, having the term "lower alkyl" the same meaning as above.

As used herein, the term "haloalkyl" refers to an alkyl group substituted with 1 to 6 halo groups. In a specific embodiment, haloalkyl is a —CX$_3$ group wherein X is a halo group. The halo groups can be independently selected. In a more specific embodiment, haloalkyl refers to a —CF$_3$ group.

As used herein, the term "haloalkoxy" refers to an alkoxy group substituted with 1 to 6 halo groups. In a specific embodiment, haloalkyl is a —OCX$_3$ group wherein X is a halo group. The halo groups can be independently selected. Preferably the halo is fluoro.

As used herein, the term "cyano" refers to a —C≡N group.

As used herein, the term "sulfinyl" refers to a —S(=O)R" group, R" is a C$_1$-C$_6$ alkyl.

As used herein, the term "sulfonyl" refers to a —S(=O)$_2$R" group, R" is a C$_1$-C$_6$ alkyl.

As used herein, the term "amido" refers to a —C(=O)NH$_2$ group.

As used herein, the term "carbocycle", "carbocyclic" or "carbocyclyl" means a radical derived from one of the known ring systems having from 1 to 4 fused rings (i.e., rings which share an adjacent pair of ring carbon atoms), wherein each one of the rings forming said ring system is saturated or partially unsaturated, and has 3-8 carbon atoms. Examples, without limitation, of carbocyclic groups are cycloalkyls such as cyclopropane, cyclobutane, cyclopentane, cyclohexane, cycloheptane and cycloalkenes such as cycloheptatriene, cyclopentene, and cyclohexadiene as well as groups like indane.

As used herein, the term "cycloalkyl" refers to a cyclic saturated aliphatic (i.e., non-aromatic) hydrocarbon group which does not comprise any carbon-to-carbon double bond or any carbon-to-carbon triple bond. Preferably, the cycloalkyl has 3 to 7 carbon atoms. Non-limiting examples of cycloalkyl groups are cyclopropyl, cyclobutyl, cyclopentyl, cyclohexyl or cycloheptyl.

As used herein, the term "heterocyclyl" or "heterocyclic" refers to ring or ring system having from 1 ring or 2 to 4 fused rings (preferably a known saturated or partially saturated 3-7 membered monocyclic ring, or known 7-10 membered bicyclic ring system) which consists of carbon atoms and from one to four heteroatoms independently selected from the group consisting of O, N, and S, wherein the nitrogen and sulfur heteroatoms can be optionally oxidized, and the nitrogen can be optionally quaternized (including e.g., any bicyclic group in which any of the above-defined heterocyclic rings is fused to a benzene ring). Non-limiting examples of saturated or partially saturated heterocyclic groups include tetrahydrofuranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl, pyrazolinyl, tetronoyl and tetramoyl groups. Example of "heterocyclyls" or "heterocyclic" rings also include, but are not limited to, morpholino, piperidyl, piperazinyl, pyrrolidinyl, thiomorpholino, homopiperazinyl, imidazolyl, imidazolidinyl, pyrazolidinyl, dioxanyl and dioxolanyl. "Heterocyclyl" can include heteroaryls when the pi-electron system of a heterocyclyl is completely conjugated.

As used herein, the term "aryl" is a radical derived from one of the known ring systems having from 1 to 4 fused rings, wherein each one of the rings forming said ring system is aromatic, and has 5-6 carbon atoms. Examples, without limitation, of aryl groups are phenyl, naphthalenyl and anthracenyl.

As used herein, the term "aryloxy" refers to an —O-aryl, wherein "aryl" is as defined above.

As used herein, the term "heteroaryl" refers to a radical derived from one of the known ring systems having from 1 ring or 2 to 4 fused rings, wherein at least one of the rings forming said ring system (preferably, each one of the rings forming said ring system) is aromatic, and at least one ring having 5-6 members (preferably, each one of the rings forming said ring system has 5 or 6 members), being each member independently selected from C, CH, N, O, S, being at least one of the members of each ring a N, O, or S. Non-limiting examples of heteroaryl groups include thienyl (thiophenyl), benzo[b]thienyl, naphtho[2,3-b]thienyl, thianthrenyl, furyl (furanyl), isobenzofuranyl, chromenyl, xanthenyl, phenoxanthiinyl, pyrrolyl, including without limitation 2H-pyrrolyl, imidazolyl, pyrazolyl, pyridyl (pyridinyl), including without limitation 2-pyridyl, 3-pyridyl, and 4-pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, beta-carbolinyl, phenanthridinyl, acrindinyl, perimidinyl, phenanthrolinyl, phenazinyl, isothiazolyl, phenothiazinyl, isoxazolyl, furazanyl, phenoxazinyl, isocoumarin, pyrido[1,2-a]pyrimidin-4-one, pyrazolo[1,5-a]pyrimidinyl, including without limitation pyrazolo[1,5-a]pyrimidin-3-yl, 1,2-benzoisoxazol-3-yl, benzimidazolyl, 2-oxindolyl and 2-oxobenzimidazolyl. When the heteroaryl group contains a nitrogen ring atom, such nitrogen ring atom may be in the form of an N-oxide, e.g., a pyridyl N-oxide, pyrazinyl N-oxide and pyrimidinyl N-oxide.

As used herein, the term "arylalkyl" refers to any of the $C_{1-10}$ alkyl groups substituted by any of the above-mentioned aryl groups as defined above. Non-limiting examples of arylalkyl group include benzyl, phenethyl, and naphthylmethyl.

As used herein, the term "arylalkoxy" refers to any of the $C_{1-10}$ alkoxy groups substituted by any of the aryl groups as defined herein. Examples of arylalkoxy groups include benzyloxy and phenethyloxy.

As used herein, the term "aryloxy" refers to oxygen substituted by any of the aryl groups defined above.

As used herein, the term "preventing an increase in a symptom" refers to both not allowing a symptom to increase or worsen, as well as reducing the rate of increase in the symptom. For example, a symptom can be measured as the amount of particular disease marker, i.e., a protein. In another example the symptom can be cognitive decline. Preventing an increase, according to the definition provided herein, means that the amount of symptom (e.g., protein or cognitive decline) does not increase or that the rate at which it increases is reduced.

As used herein, the term "treating a disease or disorder" refers to a slowing of or a reversal of the progress of the disease. Treating a disease or disorder includes treating a symptom and/or reducing the symptoms of the disease.

"Treatment of a disorder or disease" implies that a disorder or disease is suspected or has been diagnosed in a patient/subject. A patient/subject suspected of suffering from a disorder or disease typically shows specific clinical and/or pathological symptoms which a skilled person can easily attribute to a specific pathological condition (i.e., diagnose a disorder or disease).

"Treatment of a disorder or disease" may, for example, lead to a halt in the progression of the disorder or disease (e.g., no deterioration of symptoms) or a delay in the progression of the disorder or disease (in case the halt in progression is of a transient nature only). "Treatment of a disorder or disease" may also lead to a partial response (e.g., amelioration of symptoms) or complete response (e.g., disappearance of symptoms) of the subject/patient suffering from the disorder or disease. "Amelioration" of a disorder or disease may, for example, lead to a halt in the progression of the disorder or disease or a delay in the progression of the disorder or disease. Such a partial or complete response may be followed by a relapse. It is to be understood that a subject/patient may experience a broad range of responses to a treatment (e.g., the exemplary responses as described herein above).

Treatment of a disorder or disease may, inter alia, comprise curative treatment (preferably leading to a complete response and eventually to healing of the disorder or disease) and palliative treatment (including symptomatic relief).

As used herein, the term "preventing a disease or disorder" refers to a slowing of the disease or of the onset of the disease or the symptoms thereof. Preventing a disease or disorder can include stopping the onset of the disease or symptoms thereof. As used herein, the term "unit dosage form" refers to a physically discrete unit, such as a capsule or tablet suitable as a unitary dosage for a human patient. Each unit contains a predetermined quantity of a compound of Formula I, which was discovered or believed to produce the desired pharmacokinetic profile which yields the desired therapeutic effect. The dosage unit is composed of a compound of Formula I in association with at least one pharmaceutically acceptable carrier, salt, excipient, or combination thereof.

For example, a patient/subject suspected of being prone to suffer from a disorder or disease as defined herein may, in particular, benefit from a prevention of the disorder or disease. The subject/patient may have a susceptibility or predisposition for a disorder or disease, including but not limited to hereditary predisposition. Such a predisposition can be determined by standard assays, using, for example, genetic markers or phenotypic indicators. It is to be understood that a disorder or disease to be prevented in accordance with the present invention has not been diagnosed or cannot be diagnosed in the patient/subject (for example, the patient/subject does not show any clinical or pathological symptoms). Thus, the term "prevention" comprises the use of compounds of the present invention before any clinical and/or pathological symptoms are diagnosed or determined or can be diagnosed or determined by the attending physician.

As used herein, the term "dose" or "dosage" refers the amount of active ingredient that an individual takes or is administered at one time. For example, a 40 mg dose of a compound of Formula I refers to, in the case of a twice-daily dosage regimen, a situation where the individual takes 40 mg of a compound of Formula I twice a day, e.g., 40 mg in the morning and 40 mg in the evening. The 40 mg of a compound of Formula I dose can be divided into two or more dosage units, e.g., two 20 mg dosage units of a compound of Formula I in tablet form or two 20 mg dosage units of a compound of Formula I in capsule form.

As used herein, a "pharmaceutically acceptable prodrug" is a compound that may be converted under physiological conditions or by solvolysis to the specified compound or to a pharmaceutically acceptable salt of such compound.

The present invention also encompasses pharmaceutically acceptable prodrugs of the compounds described and defined herein, in particular prodrugs of the compounds of Formula I. Prodrugs of the compounds of Formula I are derivatives which have chemically or metabolically cleavable groups and become, by solvolysis or under physiological conditions, the compounds of the present invention which are pharmaceutically active in vivo. Prodrugs of compounds of Formula I according to the present invention may be formed in a conventional manner with a functional group of the compounds such as with an amino, hydroxy or carboxy group. The prodrug derivative form often offers advantages of solubility, tissue compatibility or delayed release in a mammalian organism (see, Bundgaard, H., Design of Prodrugs, pp. 7-9, 21-24, Elsevier, Amsterdam 1985). Prodrugs include acid derivatives well known to the person skilled in the art, such as, for example, esters prepared by reaction of the parent acidic compound with a suitable alcohol, or amides prepared by reaction of the parent acid compound with a suitable amine. When a compound employed in the present invention has a carboxyl group, an ester derivative prepared by reacting the carboxyl group with a suitable alcohol or an amide derivative prepared by reacting the carboxyl group with a suitable amine is exemplified as a prodrug. An especially preferred ester derivative as a prodrug is methylester, ethylester, n-propylester, isopropylester, n-butylester, isobutylester, tert-butylester, morpholinoethylester, N,N-diethylglycolamidoester or α-acetoxyethylester. When a compound employed in the present invention has a hydroxy group, an acyloxy derivative prepared by reacting the hydroxyl group with a suitable acyl-halide or a suitable acid anhydride is exemplified as a prodrug. An especially preferred acyloxy derivative as a prodrug is —OC(=O)—CH$_3$, —OC(=O)—C$_2$H$_5$, —OC(=O)-(tert-Bu), —OC(=O)—C$_{15}$H$_{31}$, —OC(=O)-(m-COONa-Ph), —OC(=O)—CH$_2$CH$_2$COONa, —O(C=O)—CH (NH$_2$)CH$_3$ or —OC(=O)—CH$_2$—N(CH$_3$)$_2$. When a compound employed in the present invention has an amino group, an amide derivative prepared by reacting the amino group with a suitable acid halide or a suitable mixed anhydride is exemplified as a prodrug. An especially preferred amide derivative as a prodrug is —NHC(=O)—(CH$_2$)$_2$OCH$_3$ or —NHC(=O)—CH(NH$_2$)CH$_3$.

As used herein, a "pharmaceutically active metabolite" is intended to mean a pharmacologically active product produced through metabolism in the body of a specified compound or salt thereof. Metabolites of a compound may be identified using routine techniques known in the art and their activities determined using tests such as those described herein.

As used herein, a "pharmaceutically acceptable salt" is intended to mean a salt that retains the biological effectiveness of the free acids and bases of the specified compound and that is not biologically or otherwise undesirable. A compound for use in the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sulfates, pyrosulfates, bisulfates, sulfites, bisulfites, phosphates, monohydrophosphates, dihydrophosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4 dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, gamma-hydroxybutyrates, glycollates, tartrates, methane-sulfonates, propanesulfonates, naphthalene-1-sulfonates, naphthalene-2-sulfonates, and mandelates.

As used herein, a "pharmaceutically acceptable carrier" refers to a non-API (API refers to Active Pharmaceutical Ingredient) substances such as disintegrators, binders, fillers, and lubricants used in formulating pharmaceutical products. They are generally safe for administering to humans according to established governmental standards, including those promulgated by the United States Food and Drug Administration and the European Medical Agency.

The present invention also embraces solid forms of the compounds of Formula I in any solvated form, including e.g. solvates with water, for example hydrates, or with organic solvents such as, e.g., methanol, ethanol or acetonitrile, i.e. as a methanolate, ethanolate or acetonitrilate, respectively; or in the form of any polymorph.

As is understood by the skilled artisan, certain variables in the list of substituents are repetitive (different name for the same substituent), generic to other terms in the list, and/or partially overlap in content with other terms. In the compounds of the invention, the skilled artisan recognizes that substituents may be attached to the remainder of the molecule via a number of positions and the preferred positions are as illustrated in the Examples.

Additionally, the compounds of Formula I or I' can contain asymmetric carbon atoms and can therefore exist in racemic and optically active forms. Thus, optical isomers or enantiomers, racemates, tautomers, and diastereomers are also encompassed in the compounds of Formula I or I'. The methods of the present invention include the use of all such isomers and mixtures thereof. Methods of separation of enantiomeric and diastereomeric mixtures are well known to one skilled in the art. Furthermore, racemic forms can be resolved by physical methods, such as, e.g., fractional crystallization, separation or crystallization of diastereomeric derivatives or separation by chiral column chromatography. The individual optical isomers can be obtained from the racemates using conventional methods, such as, e.g., salt formation with an optically active acid followed by crystallization. The present invention encompasses any isolated racemic or optically active form of compounds described in Formula I or I', or any mixture thereof. In one aspect, the compounds of the invention have a trans configuration around the cyclopropyl ring as in trans-phenylcyclopropylamine. In one aspect, the compounds of the invention have a cis configuration around the cyclopropyl ring as in cis-phenylcyclopropylamine. In a preferred aspect, the compounds of Formula I or I' have the trans configuration.

Typically, compounds according to Formula I or I' can be effective at an amount of from about 0.01 µg/kg to about 100 mg/kg per day based on total body weight. The active ingredient may be administered at once, or may be divided into a number of smaller doses to be administered at predetermined intervals of time. The suitable dosage unit for each administration can be, e.g., from about 1 µg to about 2000 mg, preferably from about 5 g to about 1000 mg.

It should be understood that the dosage ranges set forth above are exemplary only and are not intended to limit the scope of this invention. The therapeutically effective amount for each active compound can vary with factors including but not limited to the activity of the compound used, stability of the active compound in the patient's body, the severity of the conditions to be alleviated, the total weight of the patient treated, the route of administration, the ease of absorption, distribution, and excretion of the active compound by the body, the age and sensitivity of the patient to be treated, and the like, as will be apparent to a skilled artisan. The amount of administration can be adjusted as the various factors change over time.

For oral delivery, the active compounds can be incorporated into a formulation that includes pharmaceutically acceptable carriers such as binders (e.g., gelatin, cellulose, gum tragacanth), excipients (e.g., starch, lactose), lubricants (e.g., magnesium stearate, silicon dioxide), disintegrating agents (e.g., alginate, Primogel, and corn starch), and sweetening or flavoring agents (e.g., glucose, sucrose, saccharin, methyl salicylate, and peppermint). The formulation can be orally delivered in the form of enclosed gelatin capsules or compressed tablets. Capsules and tablets can be prepared in any conventional techniques. The capsules and tablets can also be coated with various coatings known in the art to modify the flavors, tastes, colors, and shapes of the capsules and tablets. In addition, liquid carriers such as fatty oil can also be included in capsules.

Suitable oral formulations can also be in the form of suspension, syrup, chewing gum, wafer, elixir, and the like. If desired, conventional agents for modifying flavors, tastes, colors, and shapes of the special forms can also be included. In addition, for convenient administration by enteral feeding tube in patients unable to swallow, the active compounds can be dissolved in an acceptable lipophilic vegetable oil vehicle such as olive oil, corn oil and safflower oil.

The active compounds can also be administered parenterally in the form of solution or suspension, or in lyophilized form capable of conversion into a solution or suspension form before use. In such formulations, diluents or pharmaceutically acceptable carriers such as sterile water and physiological saline buffer can be used. Other conventional solvents, pH buffers, stabilizers, anti-bacteria agents, surfactants, and anti-oxidants can all be included. For example, useful components include sodium chloride, acetates, citrates or phosphates buffers, glycerin, dextrose, fixed oils, methyl parabens, polyethylene glycol, propylene glycol, sodium bisulfate, benzyl alcohol, ascorbic acid, and the like. The parenteral formulations can be stored in any conventional containers such as vials and ampoules.

Routes of topical administration include nasal, bucal, mucosal, rectal, or vaginal applications. For topical administration, the active compounds can be formulated into lotions, creams, ointments, gels, powders, pastes, sprays, suspensions, drops and aerosols. Thus, one or more thickening agents, humectants, and stabilizing agents can be included in the formulations. Examples of such agents include, but are not limited to, polyethylene glycol, sorbitol, xanthan gum, petrolatum, beeswax, or mineral oil, lanolin, squalene, and the like. A special form of topical administration is delivery by a transdermal patch. Methods for preparing transdermal patches are disclosed, e.g., in Brown, et al. (1988) *Ann. Rev. Med.* 39:221-229 which is incorporated herein by reference.

Subcutaneous implantation for sustained release of the active compounds may also be a suitable route of administration. This entails surgical procedures for implanting an active compound in any suitable formulation into a subcutaneous space, e.g., beneath the anterior abdominal wall. See, e.g., Wilson et al. (1984) *J. Clin. Psych.* 45:242-247. Hydrogels can be used as a carrier for the sustained release of the active compounds. Hydrogels are generally known in the art. They are typically made by crosslinking high molecular weight biocompatible polymers into a network, which swells in water to form a gel like material. Preferably, hydrogels are biodegradable or biosorbable. For purposes of this invention, hydrogels made of polyethylene glycols, collagen, or poly (glycolic-co-L-lactic acid) may be useful. See, e.g., Phillips et al. (1984) *J. Pharmaceut. Sci.*, 73: 1718-1720.

Accordingly, the compounds of Formula I or I' or the pharmaceutical compositions comprising a compound of Formula I or I' and a pharmaceutically acceptable carrier may be administered to a subject by any convenient route of administration, whether systemically/peripherally or at the site of desired action, including but not limited to one or more of: oral (e.g. as a tablet, capsule, or as an ingestible solution), topical (e.g., transdermal, intranasal, ocular, buccal, and sublingual), parenteral (e.g., using injection techniques or infusion techniques, and including, for example, by injection, e.g. subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, or intrasternal by, e.g., implant of a depot, for example, subcutaneously or intramuscularly), pulmonary (e.g., by inhalation or insufflation therapy using, e.g., an aerosol, e.g. through mouth or nose), gastrointestinal, intrauterine, intraocular, subcutaneous, ophthalmic (including intravitreal or intracameral), rectal, and vaginal.

The active compounds can also be conjugated, to a water soluble non-immunogenic non-peptidic high molecular weight polymer to form a polymer conjugate. For example, an active compound is covalently linked to polyethylene glycol to form a conjugate. Typically, such a conjugate exhibits improved solubility, stability, and reduced toxicity and immunogenicity. Thus, when administered to a patient, the active compound in the conjugate can have a longer half-life in the body, and exhibit better efficacy. See generally, Burnham (1994) *Am. J. Hosp. Pharm.* 15:210-218. PEGylated proteins are currently being used in protein replacement therapies and for other therapeutic uses. For example, PEGylated interferon (PEG-INTRON A®) is clinically used for treating Hepatitis B. PEGylated adenosine deaminase (ADAGEN®) is being used to treat severe combined immunodeficiency disease (SCIDS). PEGylated L-asparaginase (ONCAPSPAR®) is being used to treat acute lymphoblastic leukemia (ALL). It is preferred that the covalent linkage between the polymer and the active compound and/or the polymer itself is hydrolytically degradable under physiological conditions. Such conjugates known as "prodrugs" can readily release the active compound inside the body. Controlled release of an active compound can also be achieved by incorporating the active ingredient into microcapsules, nanocapsules, or hydrogels generally known in the art. Other pharmaceutically acceptable prodrugs of the compounds of this invention include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters.

Liposomes can also be used as carriers for the active compounds of the present invention. Liposomes are micelles made of various lipids such as cholesterol, phospholipids, fatty acids, and derivatives thereof. Various modified lipids can also be used. Liposomes can reduce the toxicity of the active compounds, and increase their stability. Methods for preparing liposomal suspensions containing active ingredients therein are generally known in the art. See, e.g., U.S. Pat. No. 4,522,811; Prescott, Ed., Methods in Cell Biology, Volume XIV, Academic Press, New York, N.Y. (1976).

The active compounds can also be administered in combination with another active agent that synergistically treats or prevents the same symptoms or is effective for another disease or symptom in the patient treated so long as the other active agent does not interfere with or adversely affect the effects of the active compounds of this invention. Such other active agents include but are not limited to anti-inflammation agents, antiviral agents, antibiotics, antifungal agents, antithrombotic agents, cardiovascular drugs, cholesterol lowering agents, anti-cancer drugs, hypertension drugs, and the like.

Examples of antineoplastic agents that can be used in combination with the compounds and methods of the present invention include, in general, and as appropriate, alkylating agents, anti-metabolites, epidophyllotoxins, antineoplastic enzymes, topoisomerase inhibitors, procarbazines, mitoxantrones, platinum coordination complexes, biological response modifiers and growth inhibitors, hormonal/anti-hormonal therapeutic agents and haematopoietic growth factors. Exemplary classes of antineoplastic include the anthracyclines, vinca drugs, mitomycins, bleomycins, cytotoxic nucleosides, epothilones, discodermolides, pteridines, diynenes and podophyllotoxins. Particularly useful members of those classes include, for example, caminomycin, daunorubicin, aminopterin, methotrexate, methopterin, dichloromethotrexate, mitomycin C, porfiromycin, 5-fluorouracil, 6-mercaptopurine, gemcitabine, cytosine arabinoside, podophyllotoxin or podo-phyllotoxin derivatives such as etoposide, etoposide phosphate or teniposide, melphalan, vinblastine, vincristine, leurosidine, vindesine, leurosine, paclitaxel and the like. Other useful antineoplastic agents include estramustine, carboplatin, cyclophosphamide, bleomycin, gemcitibine, ifosamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons and interleukins.

Thus, in one embodiment the compound of the present invention, in particular the compound of Formula I or I', can be used in combination with other therapeutic agents. When the compound is used in combination with a second therapeutic agent active against the same disease, the dose of each compound may differ from that when the compound is used alone. The combination of a compound of this invention with (an) other drug(s) may comprise the administration of the drug(s) with the compound of the invention. Such an administration may comprise simultaneous/concomitant administration. However, sequential/separate administration is also envisaged.

Preferably, the second therapeutic agent to be administered in combination with the compound of the present invention is an anticancer drug. The anticancer drug to be administered in combination with the compound of the invention may be: a tumor angiogenesis inhibitor (for example, a protease inhibitor, an epidermal growth factor receptor kinase inhibitor, or a vascular endothelial growth factor receptor kinase inhibitor); a cytotoxic drug (for example, an antimetabolite, such as purine and pyrimidine analogue antimetabolites); an antimitotic agent (for example, a microtubule stabilizing drug or an antimitotic alkaloid); a platinum coordination complex; an anti-tumor antibiotic; an alkylating agent (for example, a nitrogen mustard or a nitrosourea); an endocrine agent (for example, an adrenocorticosteroid, an androgen, an anti-androgen, an estrogen, an anti-estrogen, an aromatase inhibitor, a gonadotropin-releasing hormone agonist, or a somatostatin analogue); or a compound that targets an enzyme or receptor that is overexpressed and/or otherwise involved in a specific metabolic pathway that is misregulated in the tumor cell (for example, ATP and GTP phosphodiesterase inhibitors, histone deacetylase inhibitors, protein kinase inhibitors (such as serine, threonine and tyrosine kinase inhibitors (for example, Abelson protein tyrosine kinase)) and the various growth factors, their receptors and kinase inhibitors therefor (such as epidermal growth factor receptor kinase inhibitors, vascular endothelial growth factor receptor kinase inhibitors, fibroblast growth factor inhibitors, insulin-like growth factor receptor inhibitors and platelet-derived growth factor receptor kinase inhibitors)); methionine; aminopeptidase inhibitors; proteasome inhibitors; cyclooxygenase inhibitors (for example, cyclooxygenase-1 or cyclooxygenase-2 inhibitors); or topoisomerase inhibitors (for example, topoisomerase I inhibitors or topoisomerase II inhibitors).

An alkylating agent which can be used as an anticancer drug in combination with a compound of the present invention may be, for example, a nitrogen mustard (such as cyclophosphamide, mechlorethamine (chlormethine), uramustine, melphalan, chlorambucil, ifosfamide, bendamustine, or trofosfamide), a nitrosourea (such as carmustine, streptozocin, fotemustine, lomustine, nimustine, prednimustine, ranimustine, or semustine), an alkyl sulfonate (such as busulfan, mannosulfan, or treosulfan), an aziridine (such as hexamethylmelamine (altretamine), triethylenemelamine, ThioTEPA (N,N'N'-triethylenethiophosphoramide), carboquone, or triaziquone), a hydrazine (such as procarbazine), a triazene (such as dacarbazine), or an imidazotetrazines (such as temozolomide).

A platinum coordination complex which can be used as an anticancer drug in combination with a compound of the present invention may be, for example, cisplatin, carboplatin, nedaplatin, oxaliplatin, satraplatin, or triplatin tetranitrate.

A cytotoxic drug which can be used as an anticancer drug in combination with a compound of the present invention may be, for example, an antimetabolite, including folic acid analogue antimetabolites (such as aminopterin, methotrexate, pemetrexed, or raltitrexed), purine analogue antimetabolites (such as cladribine, clofarabine, fludarabine, 6-mercaptopurine (including its prodrug form azathioprine), pentostatin, or 6-thioguanine), and pyrimidine analogue antimetabolites (such as cytarabine, decitabine, 5-fluorouracil (including its prodrug forms capecitabine and tegafur), floxuridine, gemcitabine, enocitabine, or sapacitabine).

An antimitotic agent which can be used as an anticancer drug in combination with a compound of the present invention may be, for example, a taxane (such as docetaxel, larotaxel, ortataxel, paclitaxel/taxol, or tesetaxel), a Vinca alkaloid (such as vinblastine, vincristine, vinflunine, vindesine, or vinorelbine), an epothilone (such as epothilone A, epothilone B, epothilone C, epothilone D, epothilone E, or epothilone F) or an epothilone B analogue (such as ixabepilone/aza-epothilone B).

An anti-tumor antibiotic which can be used as an anticancer drug in combination with a compound of the present invention may be, for example, an anthracycline (such as aclarubicin, daunorubicin, doxorubicin, epirubicin, idarubicin, amrubicin, pirarubicin, valrubicin, or zorubicin), an anthracenedione (such as mitoxantrone, or pixantrone) or an anti-tumor antibiotic isolated from Streptomyces (such as actinomycin (including actinomycin D), bleomycin, mritomycin (including mitomycin C), or plicamycin).

A tyrosine kinase inhibitor which can be used as an anticancer drug in combination with a compound of the present invention may be, for example, axitinib, bosutinib, cediranib, dasatinib, erlotinib, gefitinib, imatinib, lapatinib, lestaurtinib, nilotinib, semaxanib, sorafenib, sunitinib, or vandetanib.

A topoisomerase-inhibitor which can be used as an anticancer drug in combination with a compound of the present invention may be, for example, a topoisomerase I inhibitor (such as irinotecan, topotecan, camptothecin, belotecan, rubitecan, or lamellarin D) or a topoisomerase II inhibitor (such as amsacrine, etoposide, etoposide phosphate, teniposide, or doxorubicin).

Further anticancer drugs may be used in combination with a compound of the present invention. The anticancer drugs may comprise biological or chemical molecules, like TNF-related apoptosis-inducing ligand (TRAIL), tamoxifen, amsacrine, bexarotene, estramustine, irofulven, trabectedin, cetuximab, panitumumab, tositumomab, alemtuzumab, bevacizumab, edrecolomab, gemtuzumab, alvocidib, seliciclib, aminolevulinic acid, methyl aminolevulinate, efaproxiral, porfimer sodium, talaporfin, temoporfin, verteporfin, alitretinoin, tretinoin, anagrelide, arsenic trioxide, atrasentan, bortezomib, carmofur, celecoxib, demecolcine, elesclomol, elsamitrucin, etoglucid, lonidamine, lucanthone, masoprocol, mitobronitol, mitoguazone, mitotane, oblimersen, omacetaxine, sitimagene, ceradenovec, tegafur, testolactone, tiazofurine, tipifarnib, and vorinostat.

Also biological drugs, like antibodies, antibody fragments, antibody constructs (for example, single-chain constructs), and/or modified antibodies (like CDR-grafted antibodies, humanized antibodies, "full humanized" antibodies, etc.) directed against cancer or tumor markers/factors/cytokines involved in proliferative diseases can be employed in co-therapy approaches with the compounds of the invention. Examples of such biological molecules are anti-HER2 antibodies (e.g. trastuzumab, Herceptin®), anti-CD20 antibodies (e.g. Rituximab, Rituxan®, MabThera®, Reditux®), anti-CD19/CD3 constructs (see, e.g., EP-A-1 071 752) and anti-TNF antibodies (see, e.g., Taylor PC. Antibody therapy for rheumatoid arthritis. Curr Opin Pharmacol. 2003. 3(3):323-328). Further antibodies, antibody fragments, antibody constructs and/or modified antibodies to be used in co-therapy approaches with the compounds of the invention can be found in Taylor PC. Curr Opin Pharmacol. 2003. 3(3):323-328; Roxana A. Maedica. 2006. 1(1):63-65.

The combinations referred to above may conveniently be presented for use in the form of a pharmaceutical formulation. The individual components of such combinations may be administered either sequentially or simultaneously/concomitantly in separate or combined pharmaceutical formulations by any convenient route. When administration is sequential, either the present compound or the second therapeutic agent may be administered first. When administration is simultaneous, the combination may be administered either in the same or different pharmaceutical composition. When combined in the same formulation it will be appreciated that the two compounds must be stable and compatible with each other and the other components of the formulation. When formulated separately they may be provided in any convenient formulation, conveniently in such manner as are known for such compounds in the art.

In another embodiment, the compounds of the present invention, in particular the compounds of Formula I or I', are administered in combination with physical therapy, such as radiotherapy. Radiotherapy may commence before, after, or simultaneously with administration of the compounds. For example, radiotherapy may commence 1 to 10 minutes, 1 to 10 hours or 24 to 72 hours after administration of the compounds. Yet, these time frames are not to be construed as limiting. The subject is exposed to radiation, preferably gamma radiation, whereby the radiation may be provided in a single dose or in multiple doses that are administered over several hours, days and/or weeks. Gamma radiation may be delivered according to standard radiotherapeutic protocols using standard dosages and regimens. Without being bound by theory, the compounds of the present invention may be used to render cells, in particular undesired proliferative/hyperproliferative cells like cancer or tumor cells, more susceptible to such a physical therapy, e.g. radiotherapy.

Accordingly, the present invention relates to a compound of Formula I or I' or a pharmaceutically acceptable salt or solvate thereof, or a pharmaceutical composition comprising any of the aforementioned entities in combination with a pharmaceutically acceptable carrier, for use in the treatment or prevention of cancer, whereby the compound or the pharmaceutical composition is to be administered in combination with an anti-proliferative drug, an anticancer drug, a cytostatic drug, a cytotoxic drug and/or radiotherapy.

In the context of the present invention, the "subject" or "patient" or "individual", such as the subject/patient in need of treatment or prevention, may be an animal, a vertebrate animal, a mammal, a rodent (e.g. a guinea pig, a hamster, a rat, a mouse), a murine (e.g. a mouse), a canine (e.g. a dog), a feline (e.g. a cat), an equine (e.g. a horse), a primate, a simian (e.g. a monkey or ape), a monkey (e.g. a marmoset, a baboon), an ape (e.g. gorilla, chimpanzee, orangutang, gibbon), or a human. The meaning of the terms "animal", "mammal", etc. is well known in the art and can, for example, be deduced from Wehner und Gehring (1995; Thieme Verlag). In the context of this invention, it is particularly envisaged that animals are to be treated which are economically, agronomically or scientifically important. Scientifically important organisms include, but are not limited to, mice, rats, and rabbits. Non-limiting examples of agronomically important animals are sheep, cattle and pig, while, for example, cats and dogs may be considered as economically important animals. Preferably, the subject/patient/individual is a mammal. More preferably, the subject/patient/individual is a human.

General Synthetic Route Description

The compounds of the invention can be synthesized by the general routes described in Schemes 1, 2, 3, 4, 5, 6, and 7.

As illustrated in FIG. 1 (Scheme 1, wherein: DCM (dichloromethane), DMF (N,N-dimethylformamide)), the reaction of commercially available (trans)-2-phenylcyclopropanamine hydrochloride salt with commercially available sodium methoxide at room temperature using methanol as a solvent leads the to the (trans)-2-phenylcyclopropanamine free base of formula (II). It is contemplated that the corresponding cis phenylcyclopropylamine derivatives as well as the individual diastereomers ((1S,2S), (1R,2R), (1S,2R), and (1R,2S)) can be used to generate the compounds of the invention having the corresponding stereochemical configuration. These cyclopropanamine reacts with commercially available chloroacetaldehyde in presence of dried molecular sieves using dichloromethane as a solvent to get the corresponding imine derivative, which reacts with sodium cyanoborohydride as a reducing agent leading the formation of N-(2-chloroethyl)-N-[(trans)-2-phenylcyclopropyl]amine of formula (III). Alkylation of commercially available amines of formula (IV) using this chloro derivative, potassium carbonate as a base and N,N-dimethylformamide as a solvent results in the formation of the N-[(trans)-2-phenylcyclopropyl] ethane-1,2-diamine derivatives of formula (V), which are also the subject of the present invention. Addition of hydrochloric acid 2M in diethyl ether using diethyl ether as a solvent leads to the formation of the corresponding hydrochloride salts of the N-[(trans)-2-phenylcyclopropyl]ethane-1,2-diamine derivatives of formula (VI), which are subject of the present invention as defined above.

The derivatives containing a phenylcyclopropyl group substituted at the phenyl moiety (R different from a hydrogen atom in Scheme 2) or containing a heteroarylcyclopropyl group can be synthesized following the general route described in Scheme 2 using the appropriate starting materials.

Figure 2:
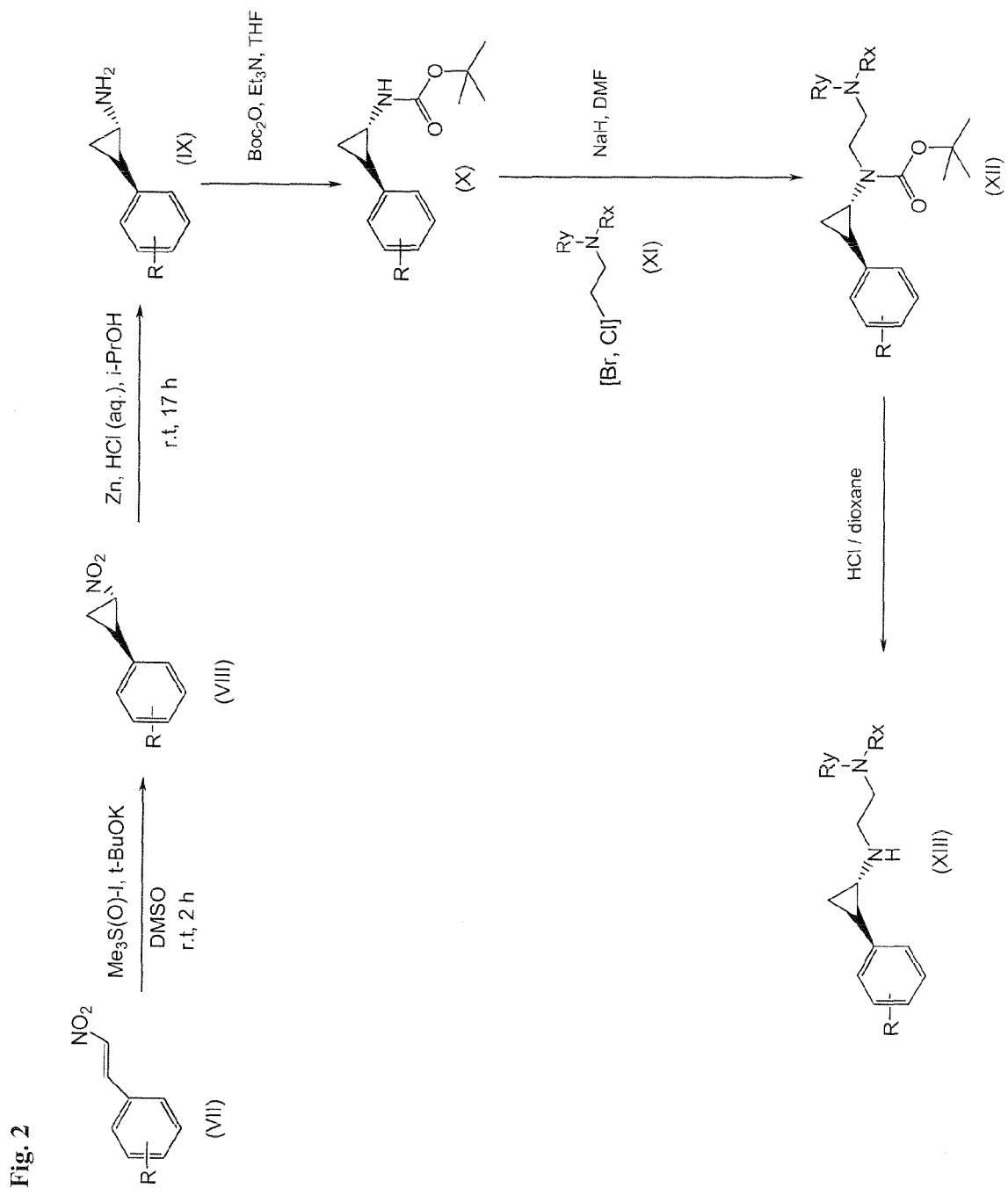
FIG. 2: The compounds of the invention can be synthesized by the general route described in the scheme shown in this figure (Scheme 2). DMSO: dimethyl sulfoxide.

As illustrated in FIG. 2 (Scheme 2; wherein DMSO is Dimethyl sulfoxide), commercially available nitrostyrene of formula (VII) are subjected to a cyclopropanation reaction using trimethylsulfoxonium iodide and potassium tert-butylate. Heteroaryl analogs of nitrostyrenes of Formula I can be used to generate compounds of the invention where (A) is a heteroaryl in place of the phenyl group shown in Scheme 2. The nitro group of the resulting nitrocyclopropyl derivatives of formula (VIII) are then reduced using zinc in hydrochloric acid to afford the cyclopropylamino derivatives of formula (IX). These compounds of formula (IX) react with t-butyl dicarbonate at room temperature using triethylamine as a base and dichloromethane as a solvent leading intermediate of formula (X) in high yield. Alkylation of the derivatives of formula (X) with commercially available derivatives of formula (XI), using NaH as a base and DMF as a solvent, lead to the intermediates of formula (XII). Deprotection of the Boc-group using HCl in dioxane leads to the formation of derivatives of formula (XIII), which are also subject of the present invention.

Figure 3:
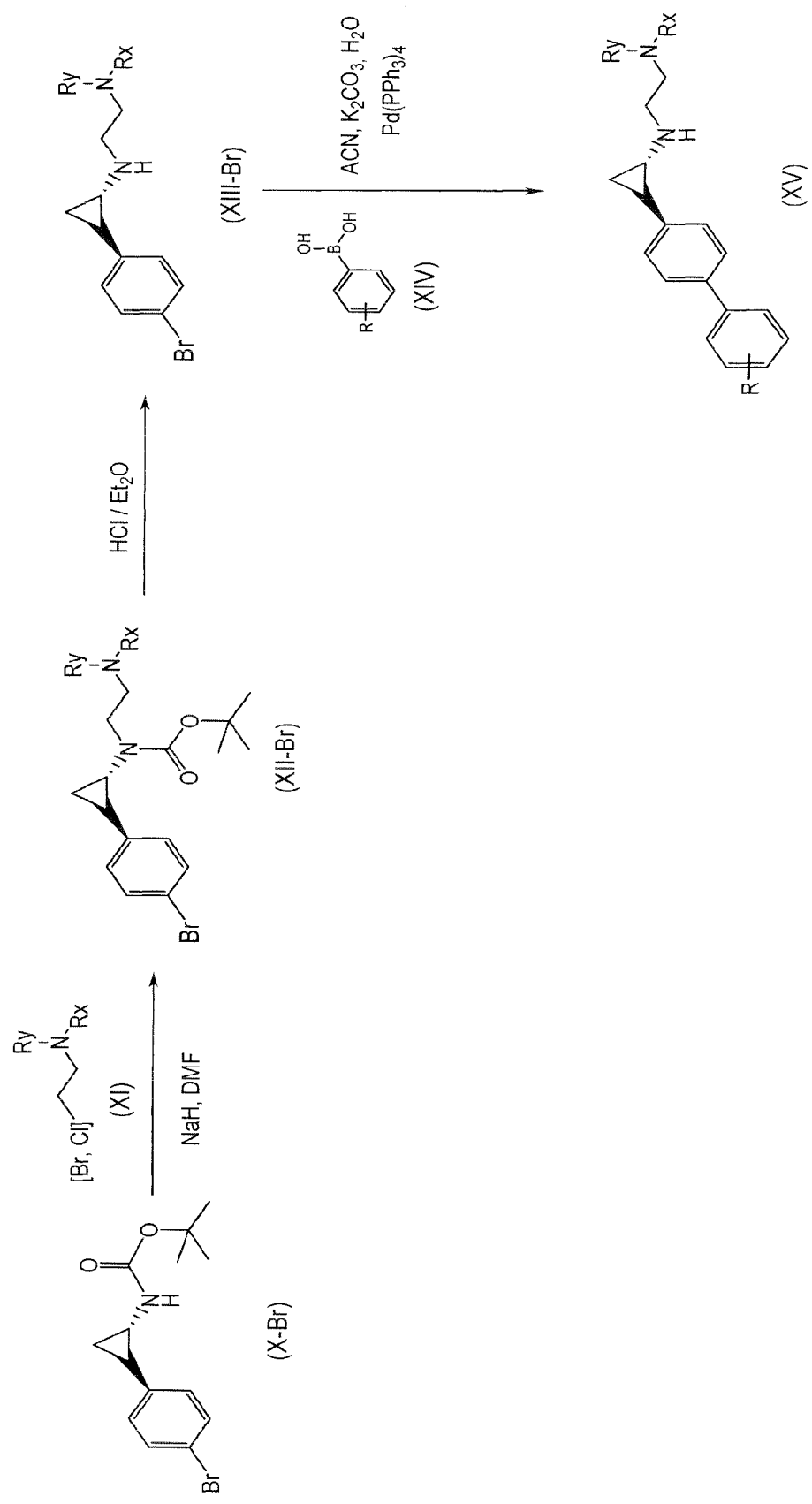
FIG. 3: The compounds of the invention can be synthesized by the general route described in the scheme shown in this figure (Scheme 3). ACN: acetonitrile.

As illustrated in FIG. 3 (Scheme 3; ACN is acetonitrile) the reaction of intermediate H(X-Br) with commercially available derivatives of formula (XI), using NaH as a base and DMF as a solvent, lead to the intermediates of formula (XII-Br). Deprotection of the Boc-group using HCl in Et$_2$O results in the formation of the derivatives of formula (XIII-Br). These N-[(trans)-2-(4-bromophenyl)cyclopropyl]ethane-1,2-diamine derivatives (XIII-Br) react with commercially available boronic acid derivatives of formula (XIV) using acetonitrile and water as a solvent, potassium carbonate as a base and Tetrakis(triphenylphospine) Paladium (0) as a catalyst lead to the formation of N-((trans)-2-(biphenyl-4-yl)cyclopropyl)ethane-1,2-diamine derivatives (XV) which are also subjects of the present invention.

Figure 4:
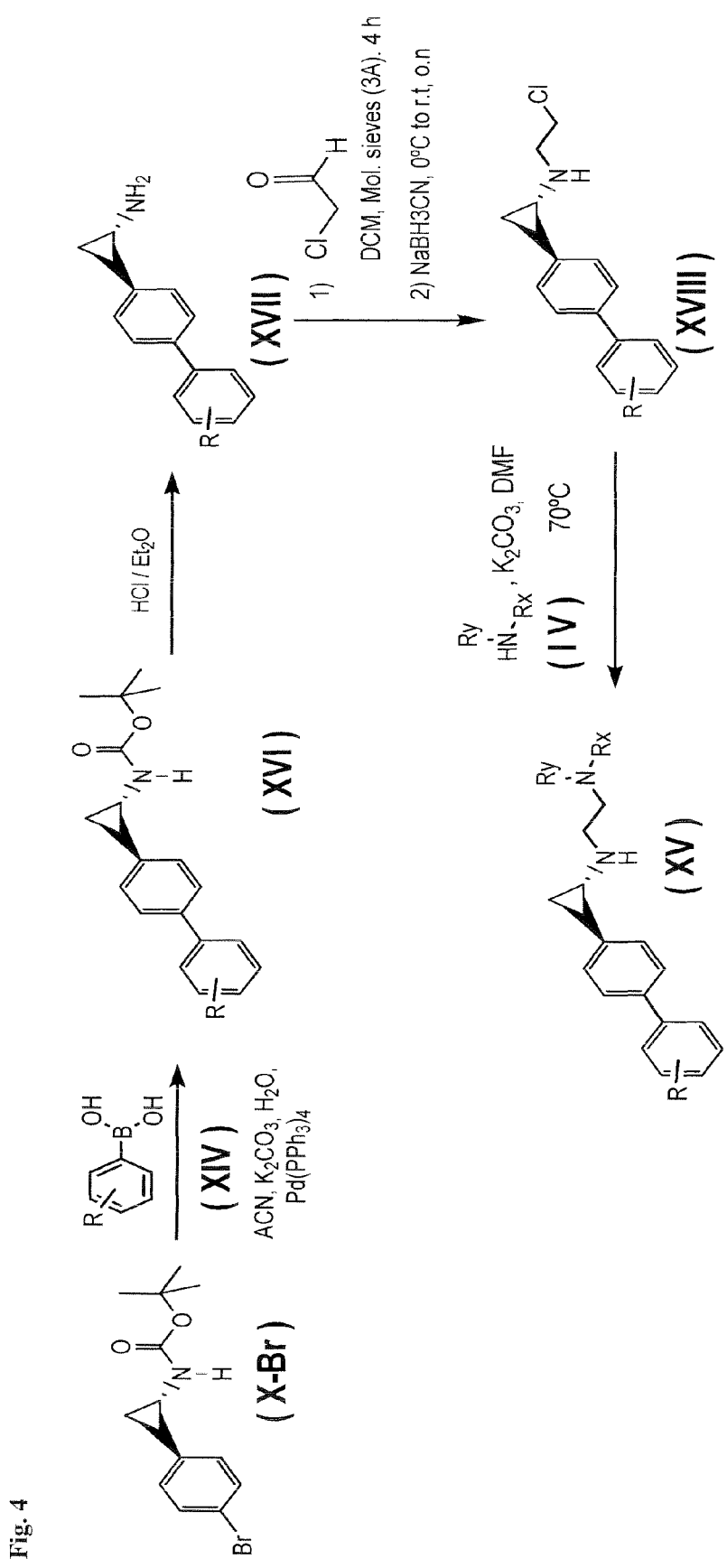
FIG. 4: The compounds of the invention can be synthesized by the general route described in the scheme shown in this figure (Scheme 4). ACN: acetonitrile.

As illustrated in FIG. 4 (Scheme 4, wherein ACN is acetonitrile), the reaction of intermediate H(X-Br) with commercially available boronic acid derivatives of formula (XIV) using acetonitrile and water as a solvent, potassium carbonate as a base and Tetrakis(triphenylphospine) Paladium (0) as a catalyst lead to the formation of the compounds of formula (XVI). Deprotection of the Boc-group using HCl in Et$_2$O results in the formation of the derivatives of formula (XVII). These (trans)-2-(biphenyl-4-yl)cyclopropanamine derivatives react with commercially available chloroacetaldehyde in presence of dried molecular sieves using dichloromethane as a solvent to yield the corresponding imine derivative, which reacts with sodium cyanoborohydride as a reducing agent leading to the formation of (trans)-2-(biphenyl-4-yl)-N-(2-chloroethyl)cyclopropanamine derivatives of formula (XVIII). Alkylation of these products with commercially available amines of formula (IV), using K$_2$CO$_3$ as a base and DMF as a solvent leads to the formation of N-((trans)-2-(biphenyl-4-yl)cyclopropyl)ethane-1,2-diamine derivatives (XV) which are also the subject of the present invention.

Figure 5:
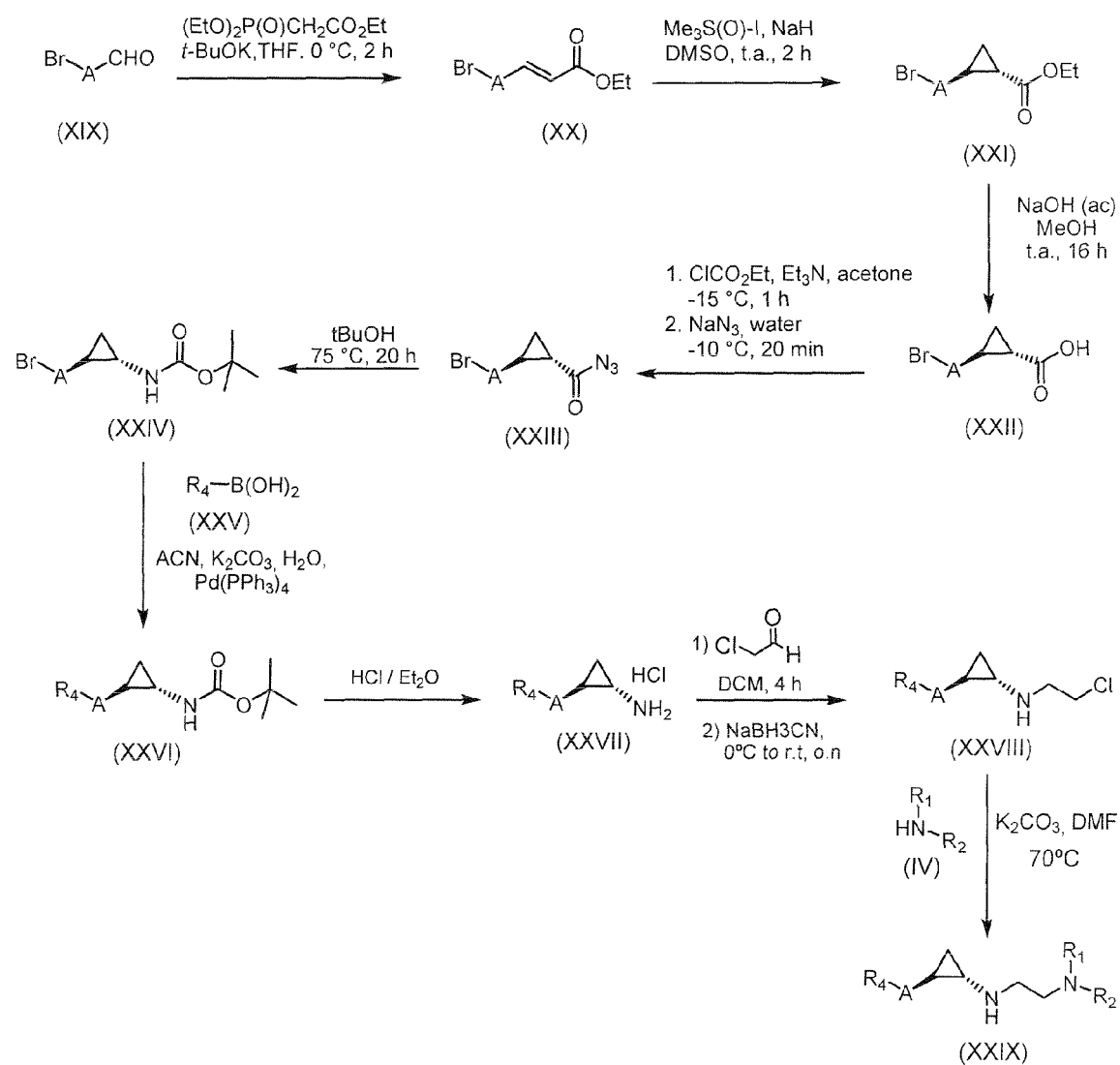
FIG. 5: The compounds of the invention can be synthesized by the general route described in the scheme shown in this figure (Scheme 5). ACN: acetonitrile; DMF: N,N-dimethylformamide; DMSO: dimethyl sulfoxide; THF: tetrahydrofurane.
Figure 6:
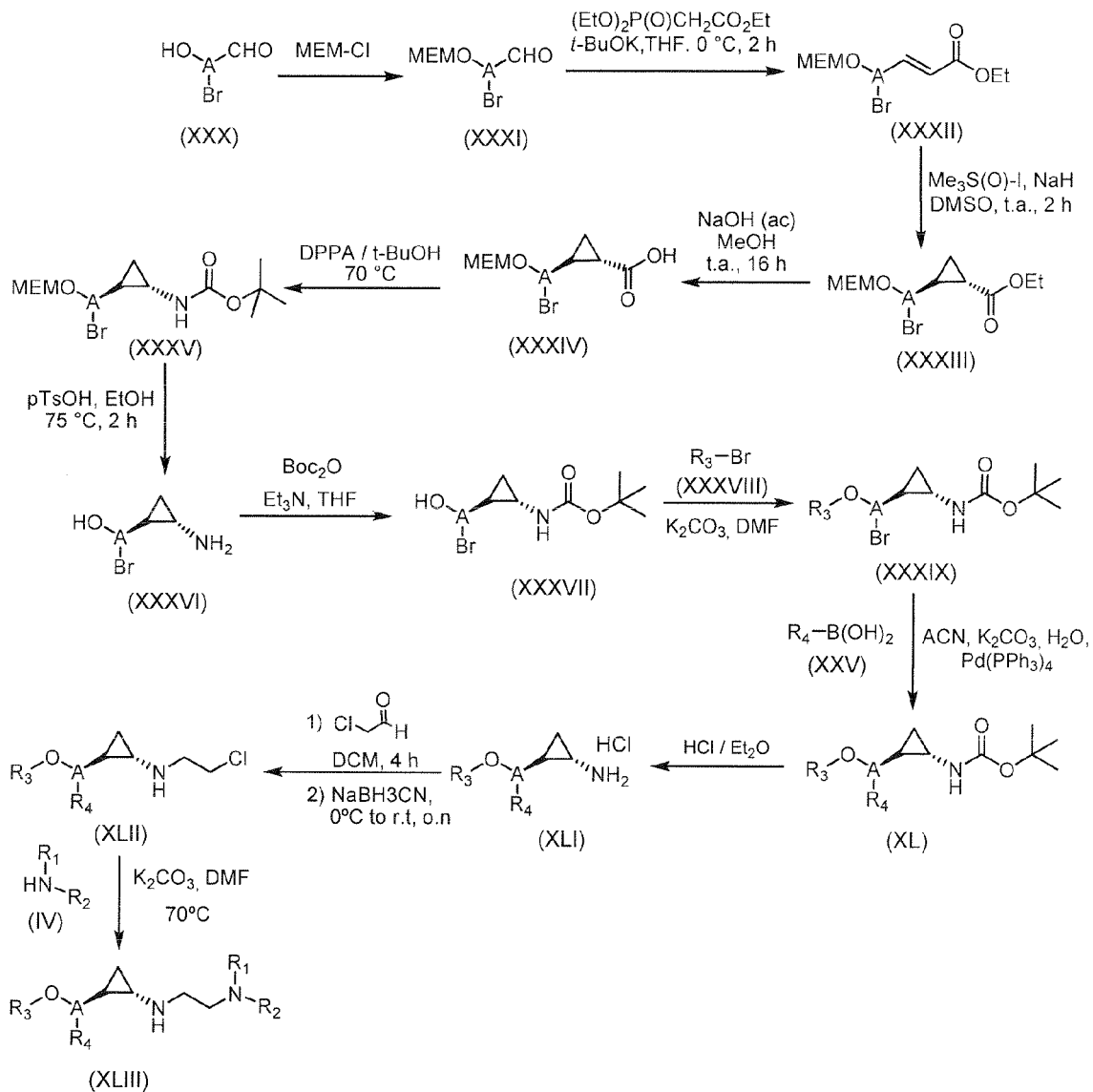
FIG. 6: The compounds of the invention can be synthesized by the general route described in the scheme shown in this figure (Scheme 6). ACN: acetonitrile; DMF: N,N-dimethylformamide; DMSO: dimethyl sulfoxide; DPPA: diphenylphosphoryl azide; MEM-Cl: methoxyethoxymethyl chloride; p-TsOH: p-toluenesulfonic acid; THF: tetrahydrofurane.
Figure 7:
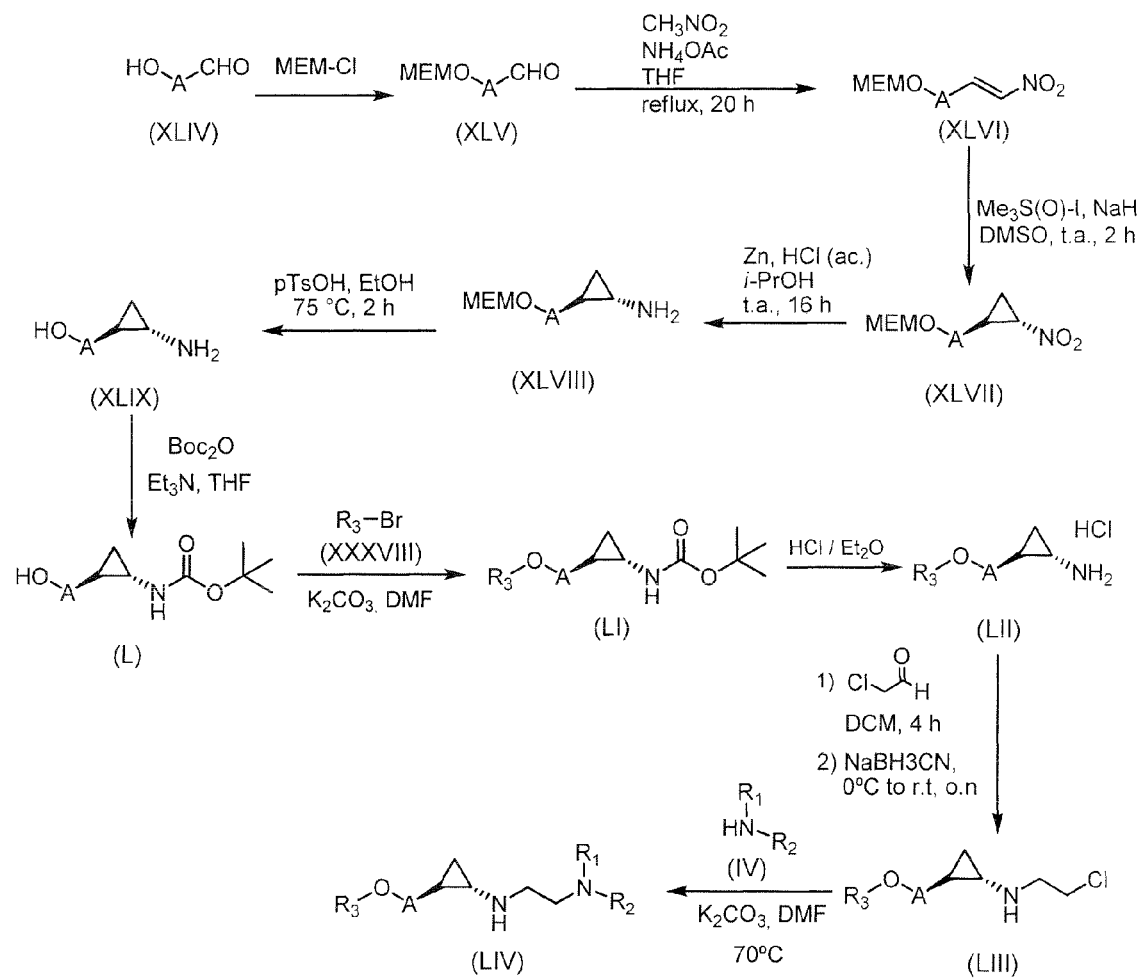
FIG. 7: The compounds of the invention can be synthesized by the general route described in the scheme shown in this figure (Scheme 7). DCM: dichloromethane; DMF: N,N-dimethylformamide; DMSO: dimethyl sulfoxide; MEM-Cl: methoxyethoxymethyl chloride; p-TsOH: p-toluenesulfonic acid; THF: tetrahydrofurane.

As illustrated in FIG. 5 (Scheme 5, wherein: ACN (Acetonitrile), DMF (N,N-Dimethylformamide), DMSO (Dymethyl sulfoxide), THF (Tetrahydrofurane)), commercially available aldehydes of formula (XIX) have been subjected to a Horner-Wadsworth-Emmons reaction using triethyl phosphono acetate and potassium tert-butoxide in tetrahydrofurane at 0° C. to get the ethyl acrylate derivative of formula (XX) which is subjected to cyclopropanation reaction using trimetilsulfoxonium iodide and sodium hydride in dimethyl sulfoxide as a solvent leading to (trans)-ethyl cyclopropanecarboxylate derivatives of formula (XXI) (being trans ((1S, 2R), (1R,2S)) mixture although the individual diastereoisomers corresponding to (1S,2R) and (1R,2S) can be used). Hydrolysis to the corresponding (trans)-cyclopropanecarboxylic acid derivatives of formula (XXII) was performed using NaOH in MeOH. The reaction, first with ethyl chloroformate and triethylamine in acetone and later with sodium azide in water leads to the formation of (trans)-cyclopropanecarbonyl azide derivatives of formula (XXIII). Reaction with tert-butanol results in the formation of tert-butyl (trans)-cyclopropylcarbamate derivatives of formula (XXIV). The reaction with commercially available boronic acid derivatives of formula (XXV) using acetonitrile and water as a solvent, potassium carbonate as a base and Tetrakis(triphenylphospine) Paladium (0) as a catalyst leads to the formation of tert-butyl(trans)-cyclopropylcarbamate derivatives of formula (XXVI). Deprotection of the Boc-group using HCl 2M in diethyl ether using diethyl ether as a solvent leads to the formation of the corresponding hydrochloride salt of the (trans)-cyclopropanamine derivatives of formula (XXVII). The reaction with commercially available chloroacetaldehyde, using dichloromethane as a solvent yield the corresponding imine derivative, which reacts with sodium cyanoborohydride as a reducing agent leading to the formation of chloroethyl cyclopropanamine derivatives of formula (XXVIII). Alkylation of these products with commercially available amines of formula (IV), using K$_2$CO$_3$ as base and DMF as a solvent leads to the formation of derivatives of formula (XXIX), which are also subject of the present invention As illustrated in FIG. 6 (Scheme 6, wherein: ACN (Acetonitrile), DMF (N,N-Dimethylformamide), DMSO (Dymethyl sulfoxide), DPPA (Diphenylphosphoryl azide), MEM-Cl (methoxyethoxymethyl chloride), p-TsOH (p-Toluenesulfonic acid), THF (Tetrahydrofurane)), the reaction of commercial available aldehydes of formula (XXX) with methoxyethoxymethyl chloride in acetone using potassium carbonate as a base leads to the formation of aldehyde derivatives of formula (XXXI). Later Horner-Wadsworth- Emmons reaction using triethyl phosphono acetate and potassium tert-butoxide in tetrahydrofurane at 0° C. leads the ethyl acrylate derivatives of formula (XXXII) which is subjected to cyclopropanation reaction using trimetilsulfoxonium iodide and sodium hydride in dimethyl sulfoxide as a solvent leading to (trans)-ethyl cyclopropanecarboxylate derivatives of formula (XXXIII) (being trans ((1S,2R), (1R,2S)) mixture although the individual diastereoisomers corresponding to (1S,2R) and (1R,2S) can be used). Hydrolysis to the corresponding (trans)-cyclopropanecarboxylic acid derivatives of formula (XXXIV) was performed using NaOH in MeOH. The reaction with diphenylphosphoryl azide in tert-butanol leads to the formation of the tert-butyl(trans)-cyclopropylcarbamate derivatives of formula (XXXV). The deprotection using p-toluenesulfonic acid in ethanol leads to the formation of the derivatives of formula (XXXVI). Reaction with t-butyl dicarbonate in tetrahydrofurane using triethylamine as a base leads to tert-butyl (trans)-cyclopropylcarbamate derivatives of formula (XXXVII). Alkylation with commercially available bromide derivatives of formula (XXXVIII) using potassium carbonate as a base and N,N-dimethylformamide as a solvent results in the formation of derivatives of formula (XXXIX). These compounds react with commercially available boronic acid derivatives of formula (XXV) using acetonitrile and water as a solvent, potassium carbonate as a base and Tetrakis(triphenylphospine) Paladium (0) as a catalyst leads to the formation of tert-butyl(trans)-cyclopropylcarbamate derivatives of formula (XL). Deprotection of the Boc-group using HCl 2M in diethyl ether using diethyl ether as a solvent leads to the formation of the corresponding hydrochloride salt of the (trans)-cyclopropanamine derivatives of formula (XLI). The reaction with commercially available chloroacetaldehyde, using dichloromethane as a solvent yield the corresponding imine derivative, which reacts with sodium cyanoborohydride as a reducing agent leading to the formation of chloroethyl cyclopropanamine derivatives of formula (XLII). Alkylation of these products with commercially available amines of formula (IV), using $K_2CO_3$ as base and DMF as a solvent leads to the formation of derivatives of formula (XLIII), which are also subject of the present invention As illustrated in FIG. 7 (Scheme 7, wherein: DCM (Dichloromethane), DMF (N,N-Dimethylformamide), DMSO (Dimethyl sulfoxide), MEM-Cl (methoxyethoxymethyl chloride), p-TsOH (p-Toluenesulfonic acid), THF (Tetrahydrofurane)), the reaction of commercially available aldehydes of formula (XLIV) with methoxyethoxymethyl chloride in acetone using potassium carbonate as a base leads to the formation of aldehyde derivatives of formula (XLV). This product reacts with nitromethane and ammonium acetate in tetrahydrofurane to get the nitrovinyl derivatives of formula (XLVI). Cyclopropanation reaction using trimethylsulfoxonium iodide and sodium hydride in dimethyl sulfoxide as a solvent leads to the formation of (trans)-nitrocyclopropane derivatives of formula (XLVII) (being trans ((1S, 2R), (1R,2S)) mixture although the individual diastereoisomers corresponding to (1S,2R) and (1R,2S) can be used). The nitro group has been then reduced using zinc in hydrochloric acid to afford the (trans)-cyclopropylamino derivatives of formula (XLVIII). The deprotection using p-toluenesulfonic acid in ethanol leads to the formation of derivatives of formula (XLIX). Reaction with t-butyl dicarbonate in tetrahydrofurane using triethylamine as a base leads to tert-butyl(trans)-cyclopropylcarbamate derivatives of formula (L). Alkylation with commercially available bromide derivatives of formula (XXXVIII) using potassium carbonate as a base and N,N-dimethylformamide as a solvent results in the formation of derivatives of formula (LI). Deprotection of the Boc-group using HCl 2M in diethyl ether using diethyl ether as a solvent leads to the formation of the corresponding hydrochloride salt of the (trans)-cyclopropanamine derivatives of formula (LII). The reaction with commercially available chloroacetaldehyde, using dichloromethane as a solvent yield the corresponding imine derivative, which reacts with sodium cyanoborohydride as a reducing agent leading to the formation of chloroethyl cyclopropanamine derivatives of formula (LIII). Alkylation of these products with commercially available amines of formula (IV), using $K_2CO_3$ as base and DMF as a solvent leads to the formation of derivatives of formula (LIV), which are also subject of the present invention

EXAMPLES

The program used to generate the names corresponding to the structures in the Example compounds below was MDL ISIS Draw 2.5 (using the ACD/Name for ISIS Draw add-in) or CHEMDRAW (ChemBioDraw Ultra version 11.0.1 by CambridgeSoft). This program named the molecules as the (1S,2R) configuration due to the configuration of the input structure and the "trans" term has been substituted in the place of the (1S,2R) term specified by the program. The structures depicted below for the Example compounds below are shown as having one particular stereochemical configuration around the cyclopropyl carbon atoms of the phenylcyclopropylamine core (1S,2R). All the compounds synthesized in the Examples are mixtures having both configurations (1R,2S) and (1S,2R), that is to say they are "trans" in respect to the cyclopropyl ring of the cyclopropyl ring system. This is due to the fact the phenylcyclopropylamine starting material used is "trans". It is contemplated that the cis configuration starting material or the individual diastereomers could be used as starting material, all of which are either commercially or synthetically available. Thus, the invention relates to compounds that have specific stereochemical configurations around the cyclopropyl ring e.g., trans ((1R,2S) and (1S,2R)) and cis ((1R,2R) and (1S,2S)) or the individual diasteromers thereof. A preferred stereochemical configuration around the cyclopropyl ring of phenylcyclopropylamine is trans.

The compounds of the examples can also be synthesized or provided in a salt form. The skilled artisan is aware and capable of making salt forms and/or converting salt forms of the compounds of the invention including those of the Examples. In some cases the compounds of the invention, including those of the Examples can be more stable as salt forms as compared to free base.

In case of conflict between a name and a drawn structure, the drawn structure is the controlling definition.

In reference to the synthetic schemes described herein the following intermediates (and analogous intermediates or derivatives thereof) can be made using the following procedures.

Intermediate A: (Trans)-2-phenylcyclopropanamine

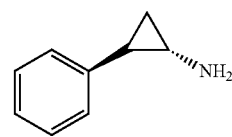

NaOMe (0.80 g, 11.8 mmol) was added over a solution of (trans)-2-phenylcyclopropanamine hydrochloride (2.00 g, 11.8 mmol) in MeOH (40 mL) and stirred 1 hour. The solvent was removed to dryness.

Intermediate B: N-(2-chloroethyl)-N-[(trans)-2-phenylcyclopropyl]amine

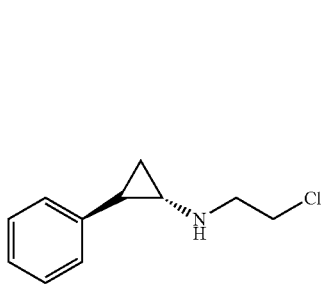

The (trans)-2-phenylcyclopropanamine previously obtained was added to activated and dried molecular sieves (3 A), proceeding with several vacuum and argon cycles. DCM (120 mL) was added and stirred before adding chloroacetaldehyde (1.5 mL, 12.0 mmol) and stirring for 4 hours. The reaction was cooled to 0° C. and NaBH$_3$CN (0.88 g, 14.0 mmol) was added. The mixture was stirred at room temperature overnight. NH$_4$Cl (20 mL) was added and the organic layer was extracted, dried with MgSO$_4$ and filtered. The crude was purified by silica gel chromatography (Hexane-MTBE 70:30) affording 1.68 g (8.56 mmol) of N-(2-chloroethyl)-N-[(trans)-2-phenylcyclopropyl]amine. Yield: 72%. $^1$HNMR (CDCl3) δ (ppm): 1.01 (q, 1H), 1.08 (quin, 1H), 1.93 (m, 1H), 2.37 (quin, 1H), 3.08 (t, 2H), 3.67 (t, 2H), 7.04 (d, 2H), 7.15 (t, 1H), 7.25 (t, 2H). MS (M+H): 195.88

Intermediate C: 1-(benzyloxy)-4-[(trans)-2-nitrocyclopropyl]benzene

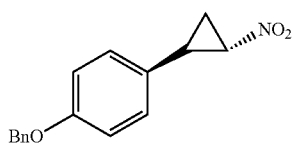

Trimethylsulfoxonium iodide (0.62 g, 2.82 mmol) was added in portions to a solution of t-BuOK (0.32 g, 2.82 mmol) in dry DMSO (5 mL). After 10 min a solution of 1-(benzyloxy)-4-[(E)-2-nitrovinyl]benzene (0.60 g, 2.35 mmol) in DMSO (5 mL) was transferred via canula and the mixture was stirred at room temperature for 6 h. The reaction was poured over water (10 mL) and extracted with Et$_2$O (3×10 mL); the organic layers were washed with brine (2×15 mL), dried over anhydrous Na$_2$SO$_4$ and filtered. After removal of the solvent, the residual orange oil was purified by column chromatography on silica gel (5% EtOAc/hexanes) affording 0.16 g of 1-(benzyloxy)-4-[(trans)-2-nitrocyclopropyl]benzene [Rf=0.5 (20% EtOAc/hexanes), white solid, 26% yield].

Intermediate D: (Trans)-2-[4-(benzyloxy)phenyl]cyclopropanamine

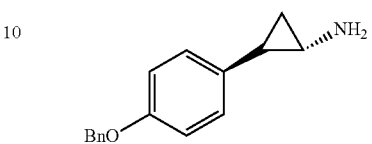

Zn dust (1.97 g, 30 mol) was added in small portions, over a period of 30 min, to a vigorously stirred solution of 1-(benzyloxy)-4-[(trans)-2-nitrocyclopropyl]benzene (Intermediate C, 0.81 g, 3.0 mmol) in i-PrOH (25 mL) and HCl (11 mL of aqueous solution 2.7 N, 30 mmol). After 17 h the mixture was filtered through a pad of celite, that was washed with 10 mL of methanol. The filtrate was concentrated and 10 mL of water were added, washing with CH$_2$Cl$_2$ (3×15 mL). The organic layers were dried over anhydrous Na$_2$SO$_4$ and filtered. After removal of the solvent, the crude product was purified by column chromatography on silica gel (10% MeOH/CH$_2$Cl$_2$) affording 0.50 g of (trans)-2-[4-(benzyloxy)phenyl]cyclopropanamine [Rf=0.2 (10% MeOH/CH$_2$Cl$_2$), white solid, 70% yield]. $^1$H NMR δ (ppm):MeOH. 400 MHz: 7.45-7.27 (m, 5H, ArH); 6.96 (d, J=8.5 Hz, 2H, ArH); 6.86 (d, J=8.5 Hz, 2H, ArH); 5.03 (s, 2H, CH2); 2.41-2.34 (m, 1H, CH); 1.86-1.76 (m, 1H, CH); 0.98-0.85 (m, 2H, CH2).

Intermediate E: Tert-butyl(trans)-2-[4-(benzyloxy)phenyl]cyclopropylcarbamate

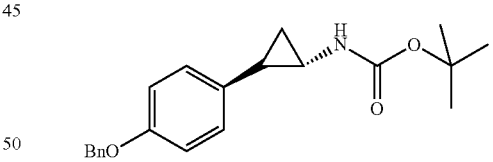

Boc$_2$O (1.65 equiv) was added to a solution of (Trans)-2-[4-(benzyloxy)phenyl]cyclopropanamine (Intermediate D; 1 equiv.) and Et$_3$N (1.65 equiv) in THF and stirred for 3 h. After removal of the solvent, the crude residue was dissolved in EtOAc and consecutively washed with water and HCl (10% aqueous solution) and brine. The organic layer was dried over anhydrous Na$_2$SO$_4$ and filtered; after removal of the solvent, the residue was purified by column chromatography on silica gel (10-20% EtOAc/Hexanes), affording the target compound (Yield 78%). $^1$H NMR δ (ppm): MeOH. 400 MHz: 7.45-7.27 (m, 5H, ArH); 6.93 (d, J=8.5 Hz, 2H, ArH); 6.86 (d, J=8.5 Hz, 2H, ArH); 5.03 (s, 2H, CH2); 2.41-2.34 (m, 1H, CH); 1.86-1.76 (m, 10H, CH; tBu); 0.98-0.85 (m, 2H, CH2).

Intermediate F:
1-bromo-4-[(trans)-2-nitrocyclopropyl]benzene

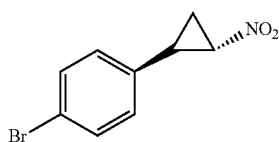

This compound was synthesized using the same methodology described in Intermediate C, using the commercially available 1-bromo-4-[(trans)-2-nitrovinyl]benzene as starting material. 27% yield.

Intermediate G:
(trans)-2-(4-bromophenyl)cyclopropanamine

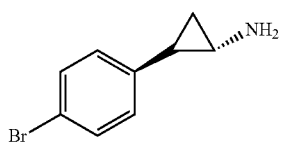

This compound was synthesized using the same methodology described in Intermediate D, using as starting material 1-bromo-4-[(trans)-2-nitrocyclopropyl]benzene. 10% yield.
$^1$HNMR (CD$_3$OD): 1.45 (m, 2H), 2.61 (m, 1H), 2.86 (m, 1H), 6.98 (d, 2H), 7.11 (d, 2H). MS (M+H): 211.9

Intermediate H: Tert-butyl(trans)-2-(4-bromophenyl)cyclopropylcarbamate

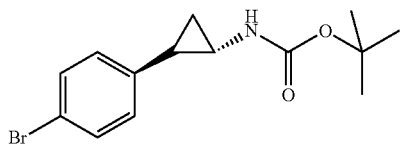

Boc$_2$O (1.65 equiv) was added to a solution of (trans)-2-(4-bromophenyl)cyclopropanamine (Intermediate G; 1 equiv.) and Et$_3$N (1.65 equiv) in THF and stirred for 3 h. After removal of the solvent, the crude residue was dissolved in EtOAc and consecutively washed with water and HCl (10% aqueous solution) and brine. The organic layer was dried over anhydrous Na$_2$SO$_4$ and filtered; after removal of the solvent, the residue was purified by column chromatography on silica gel (10-20% EtOAc/Hexanes), affording tert-butyl (trans)-2-(4-bromophenyl)cyclopropylcarbamate (Yield 85%)

Intermediate I:
4-((2-methoxyethoxy)methoxy)benzaldehyde

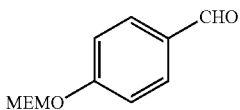

2-Methoxyethoxymethyl chloride (5.10 mL, 45.0 mmol) was slowly added to a mixture of 4-hydroxybenzaldehyde (5.00 g, 40.9 mmol) and K$_2$CO$_3$ (6.20 g, 45.0 mmol) in acetone (70 mL) cooled at 0° C. The mixture was allowed to reach room temperature and stirred for 40 h. After removal of the solvent, the crude residue was dissolved in EtOAc (50 mL) and consecutively washed with water (50 mL) and NaOH (10% aqueous solution, 2×20 mL). The organic layer was dried over anhydrous Na$_2$SO$_4$ and filtered. After removal of the solvent, 6.85 g of 4-((2-methoxyethoxy)methoxy)benzaldehyde were obtained [Rf=0.6 (50% AcOEt/Hexanes), colorless oil, 80% yield], that were used without further purification.

Intermediate J: (E)-1-((2-methoxyethoxy)methoxy)-4-(2-nitrovinyl)benzene

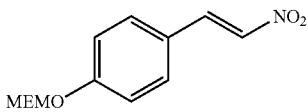

A mixture of 4-((2-methoxyethoxy)methoxy)benzaldehyde (Intermediate I, 1.86 g, 8.85 mmol) and NH$_4$OAc (0.75 g, 9.73 mmol) in dry THF (15 mL) and CH$_3$NO$_2$ (15 mL) was refluxed for 20 h and allowed to reach room temperature. The volume of the reaction was reduced to aprox. ⅓, by rotatory evaporation; the resulting solution was poured into water (15 mL) and extracted with AcOEt (2×15 mL). The organic layers were washed with brine (20 mL), dried over anhydrous Na$_2$SO$_4$ and filtered. After removal of the solvent, the residual brown oil was purified by column chromatography on silica gel (15-30% EtOAc/Hexanes) affording 1.77 g of (E)-1-((2-methoxyethoxy)methoxy)-4-(2-nitrovinyl)benzene [Rf=0.7 (50% AcOEt/Hexanes), yellow solid, 79% yield].

Intermediate K: 1-((2-methoxyethoxy)methoxy)-4-((trans)-2-nitrocyclopropyl)benzene

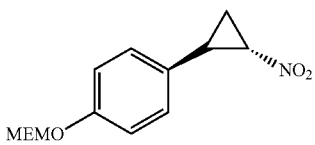

Trimethylsulfoxonium iodide (0.76 g, 3.44 mmol) was added in small portions to a suspension of NaH 0.14 g (60% in mineral oil), 3.44 mmol] in dry DMSO (5 mL). The mixture was stirred until gas evolution ceased and a clear solution was formed (45 min). Then, a solution of (E)-1-((2-methoxyethoxy)methoxy)-4-(2-nitrovinyl)benzene (Intermediate J, 0.73 g, 2.86 mmol) in DMSO (5 mL) was transferred via cannula and the reaction was stirred for additional 20 h. The mixture was poured into water (20 mL) and extracted with Et$_2$O (3×15 mL). The organic layers were washed with brine (20 mL), dried over anhydrous Na$_2$SO$_4$ and filtered; after removal of the solvent, the residual orange oil was purified by column chromatography on silica gel (10-20% EtOAc/Hexanes) affording 0.44 g of 1-((2-methoxyethoxy)methoxy)-4-((trans)-2-nitrocyclopropyl)benzene [Rf=0.4 (50% AcOEt/Hexanes), colorless oil, 36% yield].

Intermediate L: (trans)-2-(4-((2-methoxyethoxy)methoxy)phenyl)cyclopropanamine

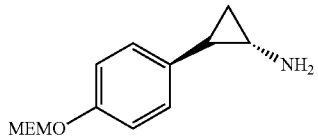

Zn dust (0.99 g, 15.1 mol) was added in small portions, over a period of 20 min, to a vigorously stirred solution of 1-((2-methoxyethoxy)methoxy)-4-((trans)-2-nitrocyclopropyl)benzene (Intermediate K, 0.40 g, 1.51 mmol) in i-PrOH (15 mL) and HCl (5.6 mL of 2.7 N aqueous solution, 15.1 mmol). After 16 h, the mixture was basified with NaOH (10% aqueous solution, 10 mL) and filtered through a pad of celite, that was washed with 10 mL of methanol. The filtrate was concentrated and 15 mL of water were added, extracting with CH$_2$Cl$_2$ (3×15 mL); the organic layers were washed with brine (25 mL), dried over anhydrous Na$_2$SO$_4$ and filtered. After removal of the solvent, the crude product was purified by column chromatography on silica gel (2-5% MeOH/CH$_2$Cl$_2$) affording 0.26 g of (trans)-2-(4-((2-methoxyethoxy)methoxy)phenyl)cyclopropanamine [Rf=0.1 (5% MeOH/CH$_2$Cl$_2$), white solid, 73% yield].

Intermediate M: 4-((trans)-2-aminocyclopropyl)phenol

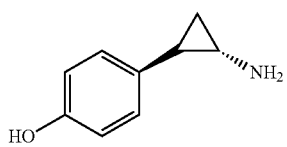

A solution of (trans)-2-(4-((2-methoxyethoxy)methoxy)phenyl)cyclopropanamine (Intermediate L, 62 mg, 0.26 mmol) and p-TsOH.H$_2$O (60 mg, 0.31 mmol) in EtOH (5 mL) was heated at 75° C. for 2 h. The pH of the reaction was adjusted to 7 with NaOH (10% aqueous solution), the mixture was poured into water (10 mL) and extracted with EtOAc (4×10 mL). The organic layer was washed with brine (10 mL), dried over anhydrous Na$_2$SO$_4$ and filtered. After removal of the solvent a brownish residue was obtained (44 mg, 4-((trans)-2-aminocyclopropyl)phenol contaminated with p-TsOH) that was used in the next step without further purification.

Intermediate N: tert-butyl(trans)-2-(4-hydroxyphenyl)cyclopropylcarbamate

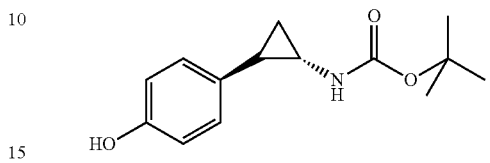

Boc$_2$O (94 mg, 0.43 mmol) was added to a solution of 4-((trans)-2-aminocyclopropyl)phenol (Intermediate M, 0.26 mmol) and Et$_3$N (59 µL, 0.43 mmol) in THF (4 mL) and stirred for 3 h. After removal of the solvent, the crude residue was dissolved in EtOAc (10 mL) and consecutively washed with [water (5 mL) and HCl (10% aqueous solution, 1 mL)] and brine (5 mL). The organic layer was dried over anhydrous Na$_2$SO$_4$ and filtered; after removal of the solvent, the residue was purified by column chromatography on silica gel (10-20% EtOAc/Hexanes), affording 26 mg of tert-butyl(trans)-2-(4-hydroxyphenyl)cyclopropylcarbamate [Rf=0.7 (50% AcOEt/Hexanes), colorless oil, 40% yield].

$^1$H-NMR (CDCl$_3$, 250 MHz, δ): 1.10-1.02 (m, 2H), 1.46 (s, 9H), 1.99-1.94 (m, 1H), 2.66 (br, 1H), 4.90 (br, 1H), 6.46 (br, 1H), 6.69 (d, 2H), 6.93 (d, 2H)

Example 1

N-[2-(4-methylpiperazin-1-yl)ethyl]-N-[(trans)-2-phenylcyclopropyl]amine dihydrochloride salt

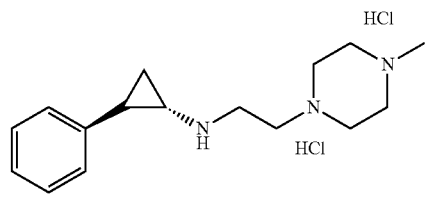

N-methyl piperazine, 0.68 mL (6.13 mmol), was added over a solution of the N-(2-chloroethyl)-N-[(trans)-2-phenylcyclopropyl]amine (Intermediate B) 0.6 g (3.06 mmol) in 60 mL DMF, followed by the addition of K$_2$CO$_3$ (3.06 mmol). The mixture was stirred at 80° C. and the progression was monitored by TLC, after completion, the solvent was evaporated to dryness. DCM and a K$_2$CO$_3$ solution were added to the crude. The organic layer was extracted, washed with water, brine and dried with MgSO$_4$ and filtered. The crude was purified by silica gel chromatography (DCM-MeOH from 100:0 to 80:20). HCl (2M in diethyl ether), 3 mL, was added dropwise to a solution of the N-[(trans)-2-phenylcyclopropyl]ethane-1,2-diamine derivative in diethyl ether (10 mL) until solid precipitation. The mixture was stirred for 2 hours, the solid was filtered, washed with diethyl ether and dried under reduced pressure to give 0.58 g of N-[2-(4-methylpiperazin-1-yl)ethyl]-N-[(trans)-2-phenylcyclopropyl]amine hydrochloride salt. Yield: 56%. $^1$HNMR (DMSO-d6) δ (ppm): 1.24 (q, 1H), 1.63 (quin, 1H), 2.62 (m, 1H), 2.78 (s, 3H), 3.00 (m, 1H), 3.28 (br, 4H), 3.73 (br, 2H), 3.44 (br, 2H), 3.61 (br, 4H), 7.17 (t, 2H), 7.20 (d, 1H), 7.28 (t, 2H), 10.12 (br, 1H), 11.90 (br, 1H). MS (M+H): 260.09

The following compounds can be synthesized following the method described for Example 1 using the corresponding commercially available amines.

Example 2

N-cyclopropyl-N'-[(trans)-2-phenylcyclopropyl]ethane-1,2-diamine dihydrochloride salt

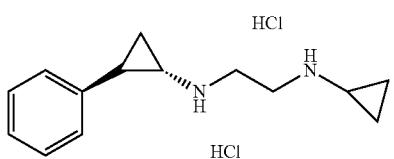

$^1$HNMR (DMSO-d6) δ (ppm): 0.76 (d, 2H), 0.91 (br, 2H), 1.28 (q, 1H), 1.58 (quin, 1H), 2.57 (m, 1H), 2.78 (m, 1H), 3.07 (m, 1H), 3.41 (m, 4H), 7.17 (d, 2H), 7.22 (t, 1H), 7.29 (t, 2H), 9.70 (br, 1H), 10.02 (br, 1H). MS (M+H): 217.05

Example 3

N,N-dimethyl-N'-(2-{[(trans)-2-phenylcyclopropyl]amino}ethyl)ethane-1,2-diamine

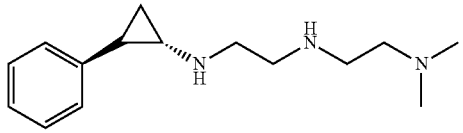

$^1$HNMR (CDCl$_3$) δ (ppm): 1.01 (q, 1H), 1.14 (quin, 1H), 2.25 (s, 3H), 2.32 (s, 3H), 2.45 (q, 2H), 2.57 (t, 2H), 2.82 (t, 2H), 2.89 (t, 2H), 2.96 (t, 2H), 3.37 (t, 1H), 3.57 (q, 1H), 7.04 (d, 2H), 7.15 (t, 1H), 7.25 (t, 2H). MS (M+H): 248.09

Example 4

(3R)-1-(2-{[(trans)-2-phenylcyclopropyl]amino}ethyl)pyrrolidin-3-amine dihydrochloride salt

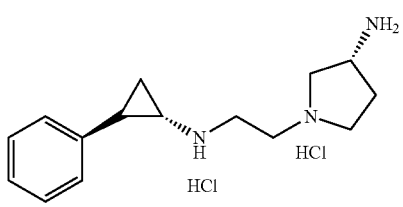

$^1$HNMR (DMSO-d6) δ (ppm): 1.26 (q, 1H), 1.60 (quin, 1H), 2.59 (m, 1H), 3.03 (br, 1H), 3.44 (b, 6H), 3.92 (br, 1H), 7.18 (t, 2H), 7.20 (d, 1H), 7.29 (t, 2H), 8.61 (br, 1H), 10.04 (br, 1H). MS (M+H): 246.01

Example 5

(3S)—N,N-dimethyl-1-(2-{[(trans)-2-phenylcyclopropyl]amino}ethyl)pyrrolidin-3-amine dihydrochloride salt

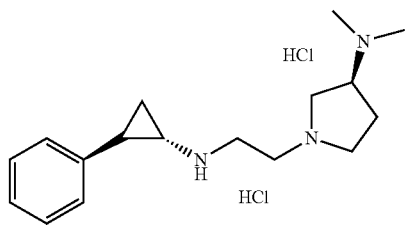

$^1$HNMR (DMSO-d6) δ (ppm): 1.24 (br, 1H), 1.63 (br, 1H), 2.34 (br, 2H), 2.62 (br, 1H), 2.76 (s, 6H), 3.03 (br, 1H), 3.49 (b, 6H), 4.06 (br, 1H), 7.17 (t, 2H), 7.19 (d, 1H), 7.28 (t, 2H), 10.35 (br, 1H), 11.76 (br, 1H). MS (M+H): 274.10

Example 6

(3R)—N,N-dimethyl-1-(2-{[(trans)-2-phenylcyclopropyl]amino}ethyl)pyrrolidin-3-amine

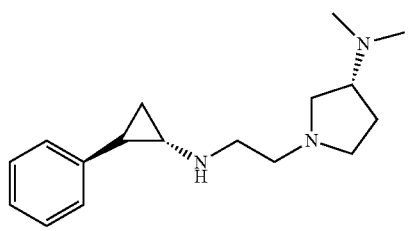

$^1$HNMR (DMSO-d6) δ (ppm): 1.26 (q, 1H), 1.61 (m, 1H), 2.29 (br, 2H), 2.48 (br, 1H), 2.76 (s, 6H), 3.03 (br, 1H), 3.42 (b, 6H), 3.98 (br, 1H), 7.18 (t, 2H), 7.20 (d, 1H), 7.29 (t, 2H). MS (M+H): 274.10

Example 7

N-[(trans)-2-phenylcyclopropyl]-N-(2-piperazin-1-ylethyl)amine dihydrochloride salt

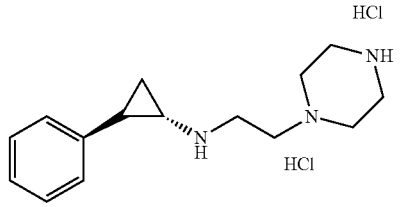

¹HNMR (DMSO-d6) δ (ppm): 1.25 (q, 1H), 1.61 (quin, 1H), 2.59 (m, 1H), 3.00 (m, 1H), 3.21 (br, 4H), 3.28 (br, 2H), 3.44 (m, 2H), 3.7 (m, 4H), 7.17 (t, 2H), 7.20 (d, 1H), 7.28 (t, 2H), 9.52 (br, 1H), 9.79 (br, 1H). MS (M+H): 245.95

Example 8

N1,N1-diethyl-N2-((trans)-2-phenylcyclopropyl)ethane-1,2-diamine dihydrochloride salt

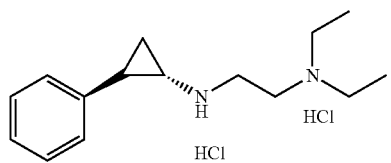

¹HNMR (DMSO-d6) δ (ppm): 1.28 (t, 7H), 1.60 (quin, 1H), 2.59 (m, 1H), 3.01 (m, 1H), 3.18 (q, 4H), 3.43 (br, 2H), 3.50 (br, 2H), 7.18 (t, 2H), 7.21 (d, 1H), 7.29 (t, 2H), 10.14 (br, 1H), 10.72 (br, 1H). MS (M+H): 233.01

Example 9

N-[(trans)-2-phenylcyclopropyl]-N-(2-piperidin-1-ylethyl)amine

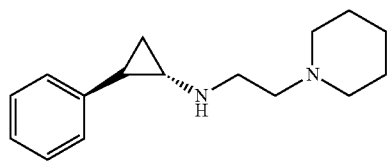

¹HNMR (DMSO-d6) δ (ppm): 1.35 (q, 1H), 1.69 (quin, 1H), 1.87 (s, 4H), 2.70 (m, 1H), 3.11 (s, 2H), 3.43 (br, 4H), 3.51 (br, 3H), 3.62 (br, 2H), 7.26 (t, 2H), 7.30 (d, 1H), 7.38 (t, 2H). MS (M+H): 245.07

Example 10

(trans)-2-(4-(benzyloxy)phenyl)-N-(2-(4-methylpiperazin-1-yl)ethyl)cyclopropanamine dihydrochloride salt

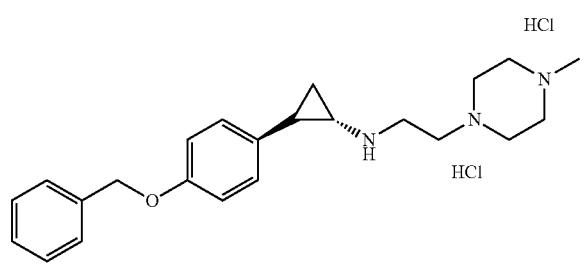

Step 1:

A solution of Intermediate E (300 mg, 1 equiv) in dry DMF (2 vols) was added to a suspension of 1.5 equiv of NaH in dry DMF (10 vols) at 0° C. After stirring for 30 mins 1.1 equiv of 1-(2-bromoethyl)-4-methylpiperazine was added and stirred at 0° C. to RT for 16 h. The progress of the reaction was monitored by TLC, after completion, the reaction mixture was poured over water, extracted with EtOAc (2×20 mL). The combined extracts were washed with water (10 mL), brine (20 mL), dried over anhydrous Na₂SO₄, filtered and evaporated to get 220 mg of crude. It was purified by preparative HPLC to give 90 mg of (trans)-2-(4-(benzyloxy)phenyl)-N-(2-(4-methylpiperazin-1-yl)ethyl)cyclopropanamine. Yield: 28%

Step 2:

HCl in 1,4 dioxane (4 mL) at 0° C. was added to a cooled solution of (trans)-2-(4-(benzyloxy)phenyl)-N-(2-(4-methylpiperazin-1-yl)ethyl)cyclopropanamine (120 mg, 1 equiv) in dioxane (5 mL) and stirred for 16 h. The progress of the reaction was monitored by TLC. After completion, it was filtered to obtain 62 mg of (trans)-2-(4-(benzyloxy)phenyl)-N-(2-(4-methylpiperazin-1-yl)ethyl)cyclopropanamine hydrochloride salt. Yield: 43%. ¹H-NMR (DMSO-d6) δ (ppm): 1.21 (q, 1H), 1.54 (quin, 1H), 2.76 (s, 3H), 2.91 (br, 2H), 3.09 (br, 2H), 3.28 (br, 2H), 3.44 (br, 2H), 5.08 (s, 2H), 6.94 (d, 2H), 7.11 (d, 2H), 7.33 (m, 1H), 7.40 (m, 4H), 9.50 (br, 1H), 10.92 (br, 1H). MS (M+H): 366.2

The following compounds (Examples 11 and 12) were synthesized following the methodology described in Scheme 3.

Example 11

(Trans)-N-(2-(4-methylpiperazin-1-yl)ethyl)-2-(3'-(trifluoromethyl)biphenyl-4-yl)cyclopropanamine dihydrochloride

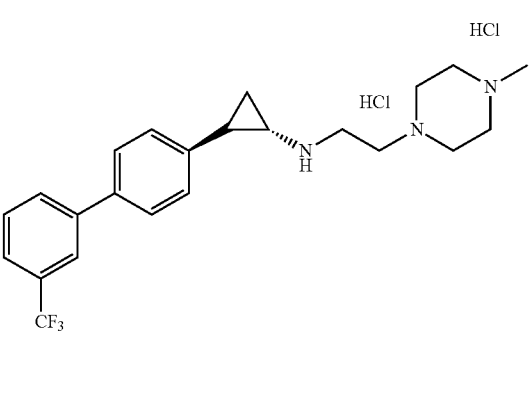

1H-NMR ¹H-NMR (DMSO-d6) δ (ppm): 1.36 (q, 1H), 1.68 (quin, 1H), 2.68 (m, 1H), 2.77 (s, 3H), 3.08 (br, 2H), 3.18

(br, 3H), 3.39 (br, 3H), 3.51 (br, 2H), 7.33 (d, 2H), 7.72 (d, 4H), 7.97 (m, 2H), 9.83 (br, 2H), 11.33 (br, 2H). MS (M+H): 404.1.

Example 12

(Trans)-2-(3'-chlorobiphenyl-4-yl)-N-(2-(4-methylpiperazin-1-yl)ethyl)cyclopropanamine dihydrochloride

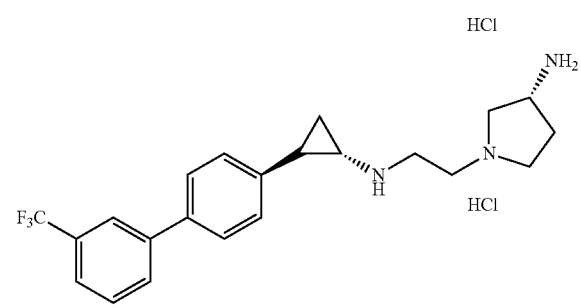

$^1$H-NMR (DMSO-d6) δ (ppm): 1.34 (q, 1H), 1.67 (quin, 1H), 2.66 (m, 1H), 2.77 (s, 3H), 3.07 (br, 2H), 3.18 (br, 3H), 3.38 (br, 6H), 3.49 (br, 2H), 7.30 (d, 2H), 7.41 (d, 1H), 7.50 (t, 1H), 7.64 (t, 3H), 7.71 (s, 1H), 9.78 (br, 2H), 11.29 (br, 2H). MS (M+H): 370.2.

The following compounds (Examples 13 and 14) were synthesized following the methodology described in Scheme 4.

Example 13

(R)-1-(2-((trans)-2-(3'-(trifluoromethyl)biphenyl-4-yl)cyclopropylamino)ethyl)pyrrolidin-3-amine dihydrochloride

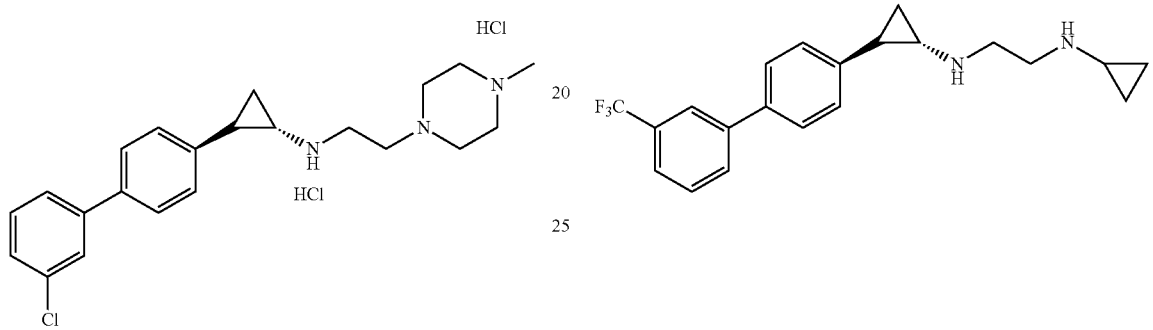

$^1$H-NMR (D2O) δ (ppm): 1.53 (q, 1H), 1.64 (quin, 1H), 2.23 (m, 1H), 2.66 (m, 2H), 3.14 (m, 1H), 3.55 (br, 1H), 3.68 (s, 6H), 3.88 (m, 1H), 4.23 (m, 1H), 7.34 (d, 2H), 7.71 (m, 4H), 7.91 (m, 1H), 7.99 (s, 1H). MS (M+H): 390.1

Example 14

N$^1$-cyclopropyl-N$^2$-((trans)-2-(3'-(trifluoromethyl)biphenyl-4-yl)cyclopropyl)ethane-1,2-diamine

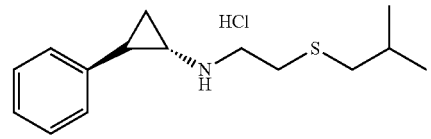

$^1$H-NMR (CDCl$_3$) δ (ppm): 0.34 (m, 2H), 0.46 (m, 2H), 1.05 (q, 1H), 1.15 (quin, 1H), 1.96 (m, 1H), 2.14 (m, 1H), 2.40 (m, 1H), 2.87 (m, 4H), 7.15 (d, 2H), 7.50 (d, 2H), 7.58 (m, 2H), 7.75 (d, 1H), 7.81 (s, 1H). MS (M+H): 361.1.

Example 15

N-(trans)-2-(isobutylthio)-ethyl-2-phenylcyclopropanamine hydrochloride

To a solution of tetrahydrofuran (THF, 10 mL) was added sodium hydride 55 mg (1.35 mmol) and cooled to 0° C. Isobutylthiol (0.14 ml, 1.35 mmol) was then added and the solution was stirred 30 min a room temperature. To this suspension, a solution of intermediate B (0.2 g, 0.67 mmol) in 1 mL of THF was added dropwise and the resulting suspension was stirred at room temperature for 12 h. The suspension was then concentrated, and the residue purified by column chromatography to afford the free base of the desired compound. The free base was then dissolved in dichloromethane and HCl (2 mL, 2M) added. The solid formed was filtered, washed with cold ether and dried to afford 0.17 g (88%) of the desired product. $^1$H-NMR (CDCl$_3$) δ (ppm): 1.05 (m, 7H), 1.21 (m, 1H), 1.44 (m, 1H), 2.41 (m, 1H), 2.92 (m, 1H), 3.20 (m, 2H), 3.61 (m, 1H), 7.16-7.25 (m, 5H), 8.5 (bs, 2H). MS (M+H): 251.

Example 16

N-trans-(2-ethoxyethyl)-2-phenylcyclopropanamine hydrochloride

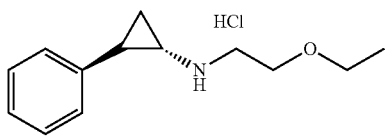

The compound was synthesized following the procedure described for Example 15 using ethyl-bromoethylether as an alkylating reagent. $^1$H-NMR (CDCl$_3$) δ (ppm): 1.05 (t, 3H), 1.21 (m, 1H), 1.44 (m, 1H), 2.41 (m, 1H), 2.92 (m, 1H), 3.20 (m, 2H), 3.42 (q, 2H), 3.61 (m, 2H), 7.16-7.25 (m, 5H), 9.2 (bs, 2H) MS (M+H): 206.

Example 17

N-trans-(2-methoxyethyl)-2-phenylcyclopropanamine hydrochloride

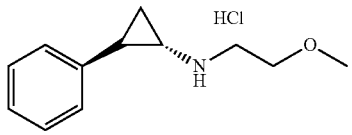

The compound was synthesized following the procedure described for Example 15 using methyl-bromoethylether as an alkylating reagent. $^1$H-NMR (CDCl3) δ (ppm): 1.21 (m, 1H), 1.44 (m, 1H), 2.41 (m, 1H), 2.92 (m, 1H), 3.20 (m, 2H), 3.61 (m, 2H), 7.19-7.25 (m, 5H), 9.2 (bs, 2H). MS (M+H): 192.

Other compounds similar to those of Examples 15-17 that can be synthesized using analogous procedures using the appropriate reagents and starting materials, as readily recognized by the skilled artisan include, but are not limited to,

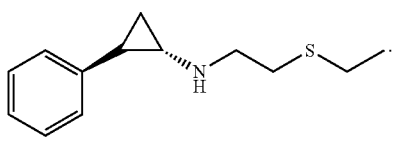

The following compound (Example 18) was synthesized following the procedure described in Scheme 2, intermediate G as starting material and 1-(2-bromoethyl)-4-methylpiperazine as an alkylating reagent.

Example 18

(trans)-2-(4-bromophenyl)-N-(2-(4-methylpiperazin-1-yl)ethyl)cyclopropanamine

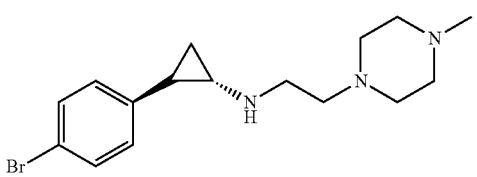

$^1$H-NMR (CDCl$_3$) δ (ppm): 0.93 (q, 1H), 1.08 (quin, 1H), 1.85 (m, 1H), 2.28 (s, 3H), 2.30 (m, 2H), 2.48 (m, 9H), 2.81 (t, 2H), 6.90 (d, 2H), 7.35 (d, 2H). MS (M+H): 338.0

Example 19

(R)-1-(2-((trans)-2-(4-(4-bromobenzyloxy)phenyl)cyclopropylamino)ethyl)pyrrolidin-3-amine hydrochloride

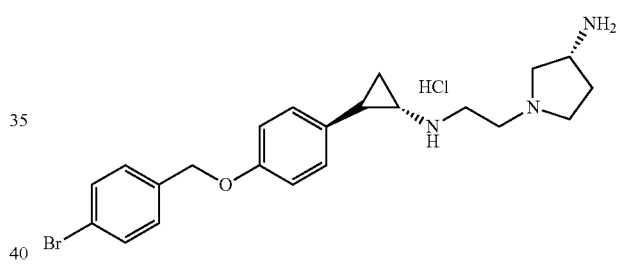

Step 1:

To a solution of tert-butyl(trans)-2-(4-hydroxyphenyl)cyclopropylcarbamate (Intermediate N, 10 g, 40.16 mmol) in DMF, K$_2$CO$_3$ (13.75 g, 100.40 mmol) and 4-bromobenzyl bromide (10.03, 40.16 mmol) was added and stirred for 18 h at RT. After completion of reaction, monitored by TLC, it was poured it into water (100 mL) and extracted with EtOAc (2×100 mL). Combined organic extracts were washed with water (50 mL), brine (50 mL), dried over anhydrous Na$_2$SO$_4$, filtered and evaporated. The crude residue was purified by column chromatography (SiO$_2$) by using EtOAc: Pet ether (2:8) to afford tert-butyl(trans)-2-(4-(4-bromobenzyloxy)phenyl)cyclopropyl carbamate (11 g, 654.86%) as a white solid Step 2:

To a solution of tert-butyl(trans)-2-(4-(4-bromobenzyloxy)phenyl)cyclopropylcarbamate (11 g, 26.37 mmol) in dioxane (110 mL) at 0° C., HCl in Dioxane (110 mL) was added and stirred for 1 h. After completion, the solvent was evaporated and residue was triturated with Et$_2$O (15 mL) to give crude salt. The crude salt was dissolved in water (150 mL), basified with Na$_2$CO$_3$ solution, extracted with EtOAc (3×100 mL). The combined extracts were washed with water (50 mL), brine (50 mL), dried over anhydrous Na$_2$SO$_4$, filtered and evaporated to get (8.2 g, 98%) (trans)-2-(4-(4-bromobenzyloxy)phenyl)cyclopropanamine Step 3:

To a solution of (trans)-2-(4-(4-bromobenzyloxy)phenyl) cyclopropanamine (4.2 g, 13.24 mmol) in DCM (42 mL) 4° A molecular sieves was added followed by chloroacetaldehyde (1.0 g, 13.24 mmol), stirred at RT for 1 h. After completion of reaction, monitored by TLC, the reaction mixture was cooled to −10° C. and Na(CN)BH₃ (0.99 mg, 15.88 mmol) was added and stirred at RT for 2 h. After completion, the reaction mixture was quenched with NH₄Cl (5%) and filtered through a pad of celite. The filtrate was extracted with DCM (2×150 mL) combined extracts were washed with water (50 mL), dried over anhydrous Na₂SO₄, filtered and evaporated. The residue was purified by flash column chromatography by using EtOAc: Pet ether to get (trans)-2-(4-(4-bromobenzyloxy)phenyl)-N-(2-chloroethyl)cyclopropanamine (4 g, 80%)

Step 4:

To a solution of (trans)-2-(4-(4-bromobenzyloxy)phenyl)-N-(2-chloroethyl)cyclopropanamine (5 g, 13.15 mmol) in dry DMF (25 mL), N-Boc pyrrolidine (5.13 g, 27.6 mmol) was added and then stirred at RT for 18 h. After completion, the reaction mixture was poured into ice water (50 mL), extracted with EtOAc (2×50 mL). The combined extracts were washed with water (50 mL), brine, dried over anhydrous Na₂SO₄, filtered and evaporated. The crude residue was purified by column chromatography (SiO₂) using MeOH: CHCl₃ (4:96) to get tert-butyl(R)-1-(2-((trans)-2-(4-(4-bromobenzyloxy) phenyl)cyclopropylamino)ethyl)pyrrolidin-3-yl carbamate (1.7 g, 24.63%) as a white solid.

Step 5:

To a cooled solution of tert-butyl(R)-1-(2-((trans)-2-(4-(4-bromobenzyloxy)phenyl)cyclopropylamino)ethyl)pyrrolidin-3-yl carbamate (0.6 g, 1.132 mmol) in dioxane (6 mL) at 0° C., HCl in 1,4 dioxane (6 mL) was added and then stirred for 16 h at RT. The progress of the reaction was monitored by TLC. After completion, the solvent was evaporated, residue was triturated with Et₂O to get (R)-1-(2-((trans)-2-(4-(4-bromobenzyloxy)phenyl)cyclopropylamino)ethyl)pyrrolidin-3-amine hydrochloride (500 mg, 82%) as a white solid.

¹H-NMR (D2O) δ (ppm): 1.38 (q, 1H), 1.50 (quin, 1H), 2.17 (m, 1H), 2.52 (m, 1H), 2.61 (m, 1H), 2.95 (m, 1H), 3.43 (m, 2H), 3.58 (m, 5H), 3.78 (m, 1H), 4.17 (m, 1H), 5.11 (s, 2H), 6.99 (d, 2H), 7.14 (d, 2H), 7.37 (d, 2H), 7.56 (d, 2H). MS (M+H): 430.1

The following compounds can be synthesized following the method described for Example 19 using the corresponding commercial available benzyl bromide and the corresponding amine.

Example 20

(R)-1-(2-((trans)-2-(4-(3-bromobenzyloxy)phenyl) cyclopropylamino)ethyl)pyrrolidin-3-amine hydrochloride

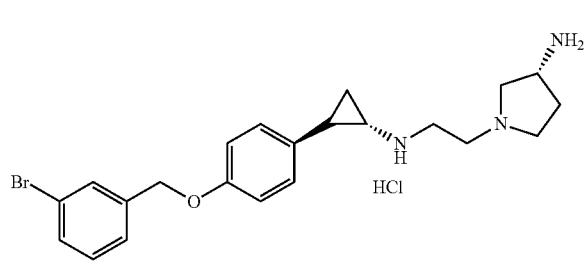

¹H-NMR (DMSO-d6) δ (ppm): 1.22 (q, 1H), 1.57 (quin, 1H), 2.22 (br, 1H), 2.57 (m, 1H), 2.98 (m, 1H), 3.50 (br, 7H), 3.91 (br, 3H), 5.11 (s, 2H), 6.95 (d, 2H), 7.13 (d, 2H), 7.36 (t, 1H), 7.43 (d, 1H), 7.52 (d, 1H), 7.64 (s, 1H), 8.65 (br, 2H), 10.04 (br, 2H). MS (M+H): 430.1

Example 21

(R)-1-(2-((trans)-2-(4-(4-chlorobenzyloxy)phenyl) cyclopropylamino)ethyl)pyrrolidin-3-amine hydrochloride

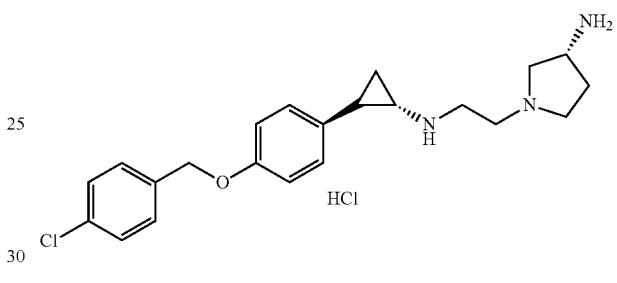

¹H-NMR (DMSO-d6) δ (ppm): 1.22 (q, 1H), 1.54 (quin, 1H), 2.25 (br, 1H), 2.96 (m, 1H), 3.45 (br, 4H), 3.83 (br, 7H), 5.09 (s, 2H), 6.94 (d, 2H), 7.12 (d, 2H), 7.45 (s, 4H), 8.50 (br, 2H), 9.90 (br, 1H). MS (M+H): 386.2

Example 22

(R)-1-(2-((trans)-2-(4-(biphenyl-4-ylmethoxy)phenyl)cyclopropylamino)ethyl)pyrrolidin-3-amine hydrochloride

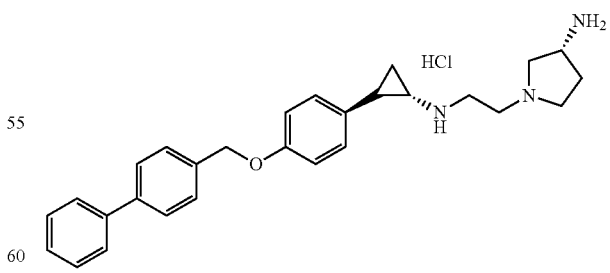

¹H-NMR (D2O) δ (ppm): 1.36 (q, 1H), 1.50 (quin, 1H), 2.19 (m, 1H), 2.51 (br, 1H), 2.61 (br, 1H), 2.94 (br, 1H), 3.46 (br, 1H), 3.59 (br, 6H), 3.82 (br 1H), 4.18 (br, 1H), 5.16 (br, 2H), 7.01 (br, 2H), 7.12 (br, 2H), 7.41 (br, 1H), 7.50 (br, 4H), 7.63 (br, 4H). MS (M+H): 428.2

Example 23

N1-((trans)-2-(4-(3-bromobenzyloxy)phenyl)cyclopropyl)-N2

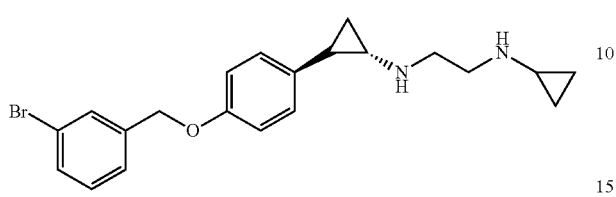

¹H-NMR (CDCl₃) δ (ppm): 0.33 (m, 2H), 0.43 (m, 2H), 0.90 (q, 1H), 1.02 (quin, 1H), 1.84 (m, 1H), 2.11 (m, 1H), 2.26 (m, 1H), 2.83 (m, 4H), 5.00 (s, 2H), 6.85 (d, 2H), 6.97 (d, 2H), 7.24 (t, 1H), 7.34 (d, 1H), 7.44 (d, 1H), 7.58 (s, 1H). MS (M+H): 401.0

Example 24

N1-cyclopropyl-N2-((trans)-2-(4-phenethoxyphenyl)cyclopropyl)ethane-1,2-diamine

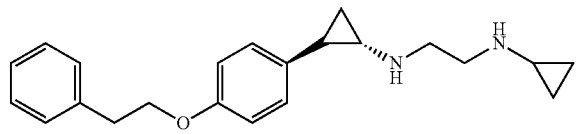

¹H-NMR (CDCl₃) δ (ppm): 0.32 (m, 2H), 0.43 (m, 2H), 0.89 (q, 1H), 1.00 (quin, 1H), 1.83 (m, 1H), 2.10 (m, 1H), 2.25 (m, 1H), 2.83 (m, 4H), 3.08 (t, 2H), 4.14 (t, 2H), 6.79 (d, 2H), 6.96 (d, 2H), 7.27 (m, 4H). MS (M+H): 337.1

Example 25

N1,N1-diethyl-N2-((trans)-2-(4-(3-fluorobenzyloxy)phenyl)cyclopropyl)ethane-1,2-diamine dihydrochloride

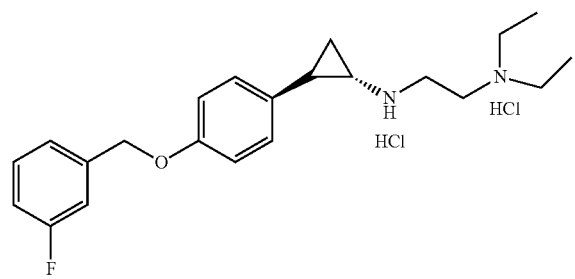

¹H-NMR (D₂O) δ (ppm): 1.29 (t, 6H), 1.40 (q, 1H), 1.53 (quin, 1H), 2.51 (m, 1H), 2.98 (m, 1H), 3.29 (q, 4H), 3.56 (m, 2H), 3.64 (m, 2H), 5.10 (s, 2H), 7.01 (d, 2H), 7.13 (t, 4H), 7.47 (t, 2H). MS (M+H): 357.4

Example 26

(S)-1-(2-((trans)-2-(3'-(trifluoromethyl)biphenyl-4-yl)cyclopropylamino)ethyl)pyrrolidin-3-amine hydrochloride

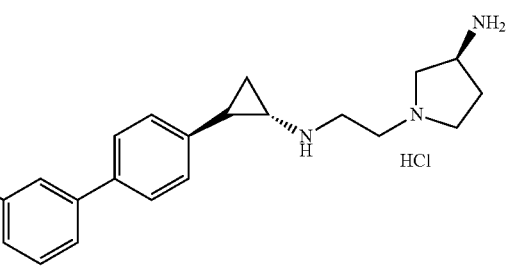

Step 1:

A solution of tert-butyl(trans)-2-(4-bromophenyl)cyclopropylcarbamate (Intermediate H, 5 g, 16.02 mmol), 3-trifluoro methyl boronic acid (3.6 g, 19.23 mmol) and K₂CO₃ (7.9 g, 57.69 mmol) in CH₃CN: H₂O (4:1), was degassed for 20 minutes. Pd (PPh₃)₄ (0.185 g, 0.160 mmol) was added and heated at reflux for 4 h. After completion, the reaction mixture was poured into water (100 mL) and extracted with EtOAc (2×50 mL). The combined organic extracts were washed with water (50 mL), brine (50 mL), dried over anhydrous Na₂SO₄, filtered and evaporated. The crude residue was purified by column chromatography (SiO₂) by using EtOAc: Pet ether (2:8) to afford tert-butyl(trans)-2-(3'-(trifluoromethyl)biphenyl-4-yl)cyclopropylcarbamate (5 g, 83%).

Step 2:

To a solution of tert-butyl(trans)-2-(3'-(trifluoromethyl)biphenyl-4-yl)cyclopropylcarbamate (5 g) in diethyl ether (50 mL) at 0° C., HCl in Diethyl ether (20 mL) was added and stirred for 1 h. After completion, the solvent was evaporated and residue was triturated with Et₂O (20 mL) to give crude salt. The crude salt was dissolved in water (50 mL), basified with Na₂CO₃ solution, extracted with EtOAc (3×50 mL). The combined extracts were washed with water (50 mL), brine (50 mL), dried over anhydrous Na₂SO₄, filtered and evaporated to get crude (trans)-2-(3'-(trifluoromethyl)biphenyl-4-yl)cyclopropanamine (3.6 g, 98.09%) as a white solid Step 3:

To a solution of (trans)-2-(3'-(trifluoromethyl)biphenyl-4-yl)cyclopropanamine (3.6 g, 38.26 mmol) in DCM (36 mL), 4° A molecular sieves was added followed by chloroacetaldehyde (5.8 mL, 38.26 mmol) and then stirred at RT for 1 h. After completion, monitored by TLC, cooled the reaction mixture at −10° C. and Na(CN)BH₃ (2.88 g, 45.92 mmol) was added and stirred at RT for 2 h. After completion, the reaction mixture was quenched with NH₄Cl (5%) and filtered through a pad of celite. The filtrate was extracted with DCM (2×50 mL), combined extracts were washed with water (40 mL), dried over anhydrous Na₂SO₄, filtered and evaporated. The residue was purified by flash column chromatography by using EtOAc: Pet ether to get (trans)-N-(2-chloroethyl)-2-(3'-(trifluoromethyl)biphenyl-4-yl)cyclopropanamine (3.2 g, 72.72%) as a liquid.

Step 4:

To a solution of (trans)-N-(2-chloroethyl)-2-(3'-(trifluoromethyl)biphenyl-4-yl)cyclopropanamine (750 mg, 2.21 mmol) in dry DMF (7.5 mL), (S)-tert-butyl pyrrolidin-3-ylcarbamate (864 mg g, 4.64 mmol) was added and stirred at RT for 48 h. After completion, the reaction mixture was poured into ice water (25 mL), extracted with EtOAc (2×20 mL). The combined extracts were washed with water (25 mL), brine (20 mL), dried over anhydrous Na$_2$SO$_4$, filtered and evaporated. The crude residue was purified by column chromatography (SiO$_2$) using MeOH: CHCl$_3$(4:96) to get tert-butyl (S)-1-(2-((trans)-2-(3'-(trifluoromethyl)biphenyl-4-yl)cyclopropylamino)ethyl)pyrrolidin-3-ylcarbamate (400 mg, 37%) as a white solid.

Step 5:

To a cooled solution of tert-butyl (S)-1-(2-((trans)-2-(3'-(trifluoromethyl)biphenyl-4-yl)cyclopropylamino)ethyl)pyrrolidin-3-ylcarbamate (400 mg) in dioxane (5 mL) at 0° C., HCl in 1,4 dioxane (5 mL) was added and stirred for 16 h at RT. The progress of the reaction was monitored by TLC. After completion, the solvent was evaporated, residue was triturated with Et$_2$O to get (S)-1-(2-((trans)-2-(3'-(trifluoromethyl)biphenyl-4-yl)cyclopropylamino)ethyl)pyrrolidin-3-amine hydrochloride (250 mg, 62%) as a white solid.

$^1$H-NMR (D2O) δ (ppm): 1.36 (q, 1H), 1.47 (quin, 1H), 2.09 (m, 1H), 2.49 (m, 2H), 2.97 (m, 1H), 3.42 (m, 3H), 3.52 (s, 4H), 3.74 (m, 1H), 4.07 (m, 1H), 7.16 (s, 2H), 7.52 (m, 4H), 7.71 (m, 1H), 7.80 (s, 1H). MS (M+H): 390.2

The following compounds can be synthesized following the method described for Example 26 using the corresponding commercially available boronic acid and the corresponding amine.

Example 27

(R)-1-(2-((trans)-2-(3'-methoxybiphenyl-4-yl)cyclopropylamino)ethyl)pyrrolidin-3-amine hydrochloride

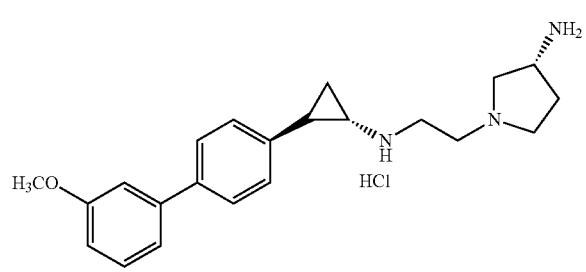

$^1$H-NMR (DMSO-d6) δ (ppm): 1.35 (q, 1H), 1.68 (quin, 1H), 2.25 (br, 2H), 2.65 (m, 1H), 3.13 (m, 2H), 3.50 (br, 6H), 3.78 (s, 3H), 3.93 (br, 2H), 6.92 (d, 1H), 7.17 (s, 1H), 7.23 (d, 1H), 7.30 (d, 2H), 7.37 (t, 1H), 7.61 (d, 2H), 8.73 (br, 3H), 10.15 (br, 2H). MS (M+H): 352.2

Example 28

(R)-1-(2-((trans)-2-(3'-chlorobiphenyl-4-yl)cyclopropylamino)ethyl)pyrrolidin-3-amine hydrochloride

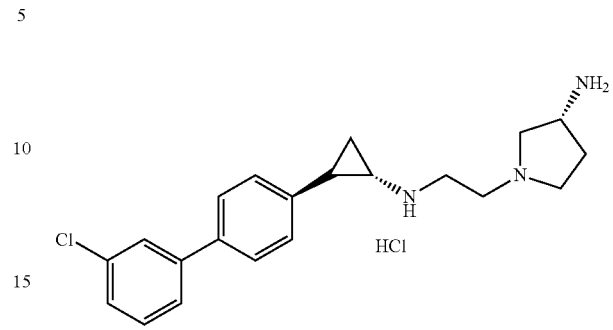

$^1$H-NMR (DMSO-d6) S (ppm): 1.37 (q, 1H), 1.67 (quin, 1H), 2.26 (br, 1H), 2.65 (m, 1H), 3.13 (m, 2H), 3.52 (br, 5H), 3.96 (br, 4H), 7.30 (d, 2H), 7.43 (d, 1H), 7.47 (t, 1H), 7.65 (t, 3H), 7.71 (s, 1H), 8.63 (br, 2H), 10.13 (br, 2H). MS (M+H): 356.1

Example 29

(R)-1-(2-((trans)-2-(4'-chlorobiphenyl-4-yl)cyclopropylamino)ethyl)pyrrolidin-3-amine dihydrochloride

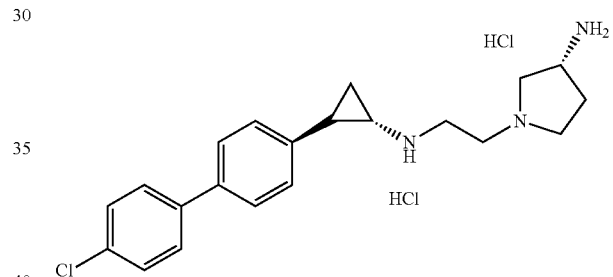

$^1$H-NMR (DMSO-d6) δ (ppm): 1.35 (q, 1H), 1.70 (quin, 1H), 2.13 (br, 1H), 2.35 (br, 1H), 2.70 (m, 1H), 3.13 (m, 1H), 3.50 (br, 3H), 3.63 (br, 4H), 3.98 (br, 2H), 7.30 (d, 2H), 7.43 (d, 1H), 7.50 (d, 2H), 7.63 (d, 2H), 7.70 (d, 2H), 8.70 (br, 3H), 10.20 (br, 2H). MS (M+H): 356.1

Example 30

(R)-1-(2-((trans)-2-(3',5'-dichlorobiphenyl-4-yl)cyclopropylamino)ethyl)pyrrolidin-3-amine hydrochloride

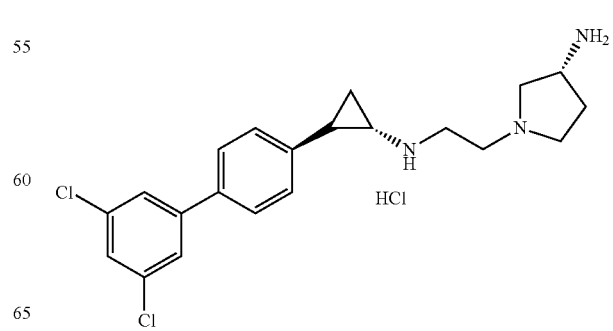

$^1$H-NMR (D2O) δ (ppm): 1.49 (q, 1H), 1.59 (quin, 1H), 2.19 (m, 1H), 2.61 (m, 2H), 3.08 (m, 1H), 3.50 (br, 3H), 3.63 (m, 5H), 3.82 (m, 1H), 4.18 (m, 1H), 7.28 (m, 2H), 7.44 (d, 1H), 7.57 (m, 4H). MS (M+H): 390.0

Example 31

N1-((trans)-2-(3'-chlorobiphenyl-4-yl)cyclopropyl)-N2-cyclopropylethane-1,2-diamine

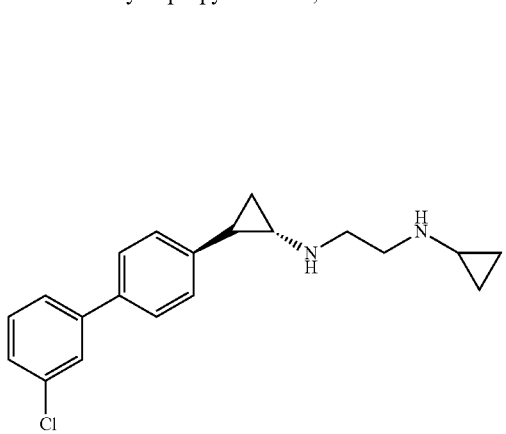

$^1$H-NMR (CDCl$_3$) δ (ppm): 0.33 (m, 2H), 0.44 (m, 2H), 1.01 (q, 1H), 1.11 (quin, 1H), 1.93 (m, 1H), 2.11 (m, 1H), 2.37 (m, 1H), 2.84 (m, 4H), 7.11 (d, 2H), 7.29 (d, 1H), 7.34 (t, 1H), 7.44 (t, 3H), 7.54 (s, 1H). MS (M+H): 327.1

Example 32

N1-((trans)-2-(2-[1,1';4',1"]Terphenyl-4"-yl-cyclopropyl)-N2-cyclopropylethane-1,2-diamine

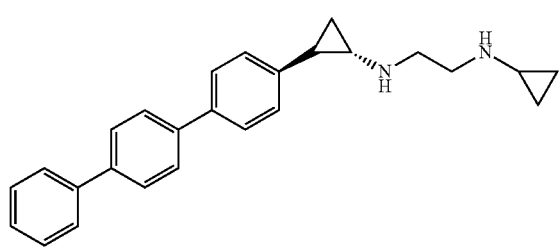

$^1$H-NMR (CDCl$_3$) δ (ppm): 0.35 (m, 2H), 0.45 (m, 2H), 1.04 (q, 1H), 1.12 (quin, 1H), 1.94 (m, 1H), 2.12 (m, 1H), 2.38 (m, 1H), 2.87 (m, 4H), 7.13 (d, 2H), 7.35 (t, 1H), 7.46 (t, 2H), 7.53 (d, 2H), 7.62 (d, 2H), 7.65 (s, 4H). MS (M+H): 369.1

Example 33

(trans)-N-(2-(piperidin-1-yl)ethyl)-2-(3'-(trifluoromethyl)biphenyl-4-yl)cyclopropanamine

$^1$H-NMR (CDCl$_3$) δ (ppm): 1.03 (q, 1H), 1.14 (quin, 1H), 1.46 (br, 2H), 1.63 (br, 4H), 1.95 (m, 1H), 2.5 (m, 8H), 2.89 (m, 2H), 7.13 (d, 2H), 7.48 (d, 2H), 7.54 (m, 2H), 7.73 (d, 1H), 7.80 (s, 1H). MS (M+H): 389.1

Example 34

N1,N1-diethyl-N2-((trans)-2-(3'-(trifluoromethyl)biphenyl-4-yl)cyclopropyl)ethane-1,2-diamine

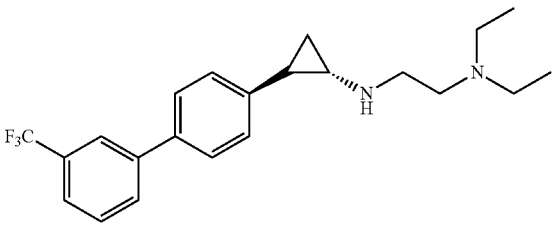

$^1$H-NMR (CDCl$_3$) δ (ppm): 1.03 (t, 7H), 1.16 (quin, 1H), 1.97 (m, 1H), 2.41 (m, 1H), 2.56 (quin, 6H), 2.83 (t, 2H), 7.16 (d, 2H), 7.50 (d, 2H), 7.57 (m, 2H), 7.75 (d, 1H), 7.82 (s, 1H). MS (M+H): 377.1

Example 35

(trans)-N-(2-(piperazin-1-yl)ethyl)-2-(3'-(trifluoromethyl)biphenyl-4-yl)cyclopropanamine hydrochloride

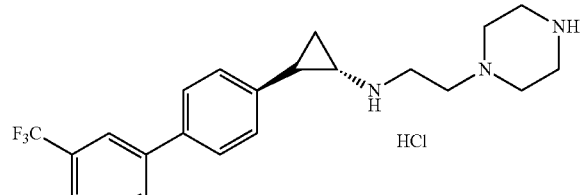

$^1$H-NMR (DMSO-d6) δ (ppm): 1.35 (q, 1H), 1.67 (quin, 1H), 2.67 (m, 1H), 3.10 (br, 1H), 3.29 (br, 8H), 3.42 (br, 3H), 3.57 (s, 1H), 7.32 (d, 2H), 7.70 (d, 4H), 7.95 (s, 1H), 7.98 (d, 1H), 9.46 (br, 2H), 9.81 (br, 2H). MS (M+H): 390.2

Example 36

(R)-1-(2-((trans)-2-(6-(benzyloxy)-4'-(trifluoromethyl)biphenyl-3-yl)cyclopropylamino)ethyl)pyrrolidin-3-amine dihydrochloride

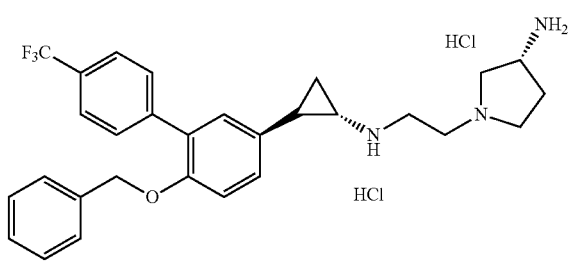

Step 1:
A solution of tert-butyl(trans)-2-(4-(benzyloxy)-3-bromophenyl)cyclopropylcarbamate (1 g, 2.4 mmol), 4-trifluoro methyl boronic acid (545 mg, 2.86 mmol) and $K_2CO_3$ (1.17 g, 8.58 mmol) in ACN:$H_2O$ (4:1), was degassed for 20 minutes. Pd (PPh$_3$)$_4$ (27 mg, 0.02 mmol) was added and heated at reflux for 4 h. After completion, the reaction mixture was poured into water (20 mL) and extracted with EtOAc (2×20 mL). Combined organic extracts were washed with water (20 mL), brine (20 mL), dried over anhydrous $Na_2SO_4$, filtered and evaporated. The crude residue was purified by column chromatography (SiO$_2$) by using EtOAc: Pet ether (2:8) to afford tert-butyl(trans)-2-(6-(benzyloxy)-4'-(trifluoromethyl)biphenyl-3-yl)cyclopropyl carbamate (800 mg, 69.56%).
Step 2:
To a solution of tert-butyl(trans)-2-(6-(benzyloxy)-4'-(trifluoromethyl)biphenyl-3-yl)cyclopropyl carbamate (800 mg, 1.65 mmol) in diethyl ether (8 mL) at 0° C., HCl in Diethyl ether (8 mL) was added and stirred for 1 h. After completion, the solvent was evaporated and residue was triturated with Et$_2$O (5 mL) to give crude salt. The crude salt was dissolved in water (20 mL), basified with Na2CO3 solution, extracted with EtOAc (3×20 mL). The combined extracts were washed with water (20 mL), brine (20 mL), dried over anhydrous $Na_2SO_4$, filtered and evaporated to get crude (trans)-2-(6-(benzyloxy)-4'-(trifluoromethyl)biphenyl-3-yl)cyclopropanamine (520 mg, 82.5%) as a white solid
Step 3:
To a solution of (trans)-2-(6-(benzyloxy)-4'-(trifluoromethyl)biphenyl-3-yl)cyclopropanamine (520 mg, 2.08 mmol) in DCM (6 mL), 4° A molecular sieves was added followed by chloroacetaldehyde (0.33 mL, 2.5 mmol) and stirred at RT for 1 h. After completion, monitored by TLC, the reaction mixture was cooled at −10° C. and Na(CN)BH$_3$ (157 mg, 2.5 mmol) was added and stirred at RT for 2 h. After completion, the reaction mixture was quenched with NH$_4$Cl (5%) and filtered through a pad of celite. The filtrate was extracted with DCM (2×20 mL), combined extracts were washed with water (20 mL), dried over anhydrous $Na_2SO_4$, filtered and evaporated. The residue was purified by flash column chromatography by using EtOAc: Pet ether to get (trans)-2-(6-(benzyloxy)-4'-(trifluoromethyl)biphenyl-3-yl)-N-(2-chloroethyl)cyclopropanamine (500 mg, 83.3%) as a liquid.

Step 4:
To a solution of (trans)-2-(6-(benzyloxy)-4'-(trifluoromethyl)biphenyl-3-yl)-N-(2-chloroethyl)cyclopropanamine (500 mg, 1.12 mmol) in dry DMF (5 mL), (R)-tert-butyl pyrrolidin-3-ylcarbamate (438 mg, 2.3 mmol) was added and stirred at RT for 48 h. After completion, the reaction mixture was poured into ice water (20 mL), extracted with EtOAc (2×20 mL). The combined extracts were washed with water (25 mL), brine, dried over anhydrous $Na_2SO_4$, filtered and evaporated. The crude residue was purified by column chromatography (SiO$_2$) using MeOH: CHCl$_3$ (4:96) to get tert-butyl(R)-1-(2-((trans)-2-(6-(benzyloxy)-4'-(trifluoromethyl)biphenyl-3-yl)cyclopropylamino)ethyl)pyrrolidin-3-ylcarbamate (400 mg, 60.6%) as a white solid.
Step 5:
To a cooled solution of tert-butyl(R)-1-(2-((trans)-2-(6-(benzyloxy)-4'-(trifluoromethyl)biphenyl-3-yl)cyclopropylamino)ethyl)pyrrolidin-3-ylcarbamate (400 mg, 0.67 mmol) in dioxane (8 mL) at 0° C., HCl in 1,4dioxane (4 mL) was added and stirred for 16 h at RT. The progress of the reaction was monitored by TLC. After completion, the solvent was evaporated, residue was triturated with Et$_2$O to get (R)-1-(2-((trans)-2-(6-(benzyloxy)-4'-(trifluoromethyl)biphenyl-3-yl)cyclopropylamino)ethyl)pyrrolidin-3-amine dihydrochloride (380 mg, 95%) as a white solid.
$^1$H-NMR (DMSO-d6) δ (ppm): 1.32 (q, 1H), 1.59 (quin, 1H), 2.25 (br, 2H), 2.62 (m, 1H), 3.08 (m, 1H), 3.40-4.00 (br, 2H), 5.15 (s, 2H), 7.18 (d, 2H), 7.23 (d, 1H), 7.30 (m, 1H), 7.35 (s, 4H), 7.77 (s, 4H), 8.60 (br, 3H), 10.10 (br, 2H). MS (M+H): 496.2

The following compound can be synthesized following the method described for Example 36 using the corresponding commercially available boronic acid.

Example 37

(R)-1-(2-((trans)-2-(6-(benzyloxy)biphenyl-3-yl)cyclopropylamino)ethyl)pyrrolidin-3-amine dihydrochloride

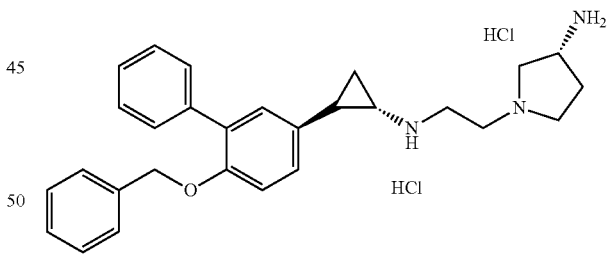

$^1$H-NMR (DMSO-d6) δ (ppm): 1.28 (q, 1H), 1.59 (quin, 1H), 2.25 (br, 2H), 2.62 (m, 1H), 3.06 (m, 1H), 3.40-4.00 (br, 10H), 5.15 (s, 2H), 7.13 (m, 3H), 7.34 (m, 6H), 7.40 (m, 2H), 7.54 (d, 2H), 8.66 (br, 3H), 10.10 (br, 2H). MS (M+H): 428.3

Example 38

Biological Assays

The compounds of the invention can be tested for their ability to inhibit LSD1. The ability of the compounds of the invention to inhibit LSD1 can be tested as follows. Human recombinant LSD1 protein was purchased from BPS Bioscience Inc. In order to monitor LSD1 enzymatic activity and/or its inhibition rate by our inhibitor(s) of interest, di-methylated H3-K4 peptide (Millipore) was chosen as a substrate. The demethylase activity was estimated, under aerobic conditions, by measuring the release of $H_2O_2$ produced during the catalytic process, using the Amplex® Red peroxide/peroxidase-coupled assay kit (Invitrogen).

Briefly, a fixed amount of LSD1 was incubated on ice for 15 minutes, in the absence and/or in the presence of various concentrations of inhibitor (e.g., from 0 to 75 µM, depending on the inhibitor strength). Tranylcypromine (Biomol International) was used as a control for inhibition. Within the experiment, each concentration of inhibitor was tested in triplicate. After leaving the enzyme interacting with the inhibitor, 12.5 µM of di-methylated H3-K4 peptide was added to each reaction and the experiment was left for 1 hour at 37° C. in the dark. The enzymatic reactions were set up in a 50 mM sodium phosphate, pH 7.4 buffer. At the end of the incubation, Amplex® Red reagent and horseradish peroxidase (HPR) solution were added to the reaction according to the recommendations provided by the supplier (Invitrogen), and left to incubate for 30 extra minutes at room temperature in the dark. A 1 µM $H_2O_2$ solution was used as a control of the kit efficiency. The conversion of the Amplex® Red reagent to resorufin due to the presence of $H_2O_2$ in the assay, was monitored by fluorescence (excitation at 540 nm, emission at 590 nm) using a microplate reader (Infinite 200, Tecan). Arbitrary units were used to measure level of $H_2O_2$ produced in the absence and/or in the presence of inhibitor.

The maximum demethylase activity of LSD1 was obtained in the absence of inhibitor and corrected for background fluorescence in the absence of LSD1. The Ki of each inhibitor was estimated at half of the maximum activity.

The results presented in Table 1 below show the results of the LSD1 inhibition studies for a number of the Example compounds. Parnate (2-trans phenylcyclopropylamine) was found to have a Ki of from about 15 to 35 micromolar depending on the enzyme preparation. The studies show that the compounds of the invention have unexpectedly potent LSD1 inhibition.

Example 39

Biological Assays

Monoamine Oxidase Assays for Determining the Selectivity of the Compounds of the Invention for LSD1

Human recombinant monoamine oxidase proteins MAO-A and MAO-B were purchased from Sigma Aldrich. MAOs catalyze the oxidative deamination of primary, secondary and tertiary amines. In order to monitor MAO enzymatic activities and/or their inhibition rate by inhibitor(s) of interest, a fluorescent-based (inhibitor)-screening assay was set up. 3-(2-Aminophenyl)-3-oxopropanamine (kynuramine dihydrobromide, Sigma Aldrich), a non fluorescent compound was chosen as a substrate. Kynuramine is a non-specific substrate for both MAOs activities. While undergoing oxidative deamination by MAO activities, kynuramine is converted into 4-hydroxyquinoline (4-HQ), a resulting fluorescent product.

The monoamine oxidase activity was estimated by measuring the conversion of kynuramine into 4-hydroxyquinoline. Assays were conducted in 96-well black plates with clear bottom (Corning) in a final volume of 100 µL. The assay buffer was 100 mM HEPES, pH 7.5. Each experiment was performed in triplicate within the same experiment.

Briefly, a fixed amount of MAO (0.25 µg for MAO-A and 0.5 µg for MAO-B) was incubated on ice for 15 minutes in the reaction buffer, in the absence and/or in the presence of various concentrations of inhibitor (e.g., from 0 to 50 µM, depending on the inhibitor strength). Tranylcypromine (Biomol International) was used as a control for inhibition.

After leaving the enzyme(s) interacting with the inhibitor, 60 to 90 µM of kynuramine was added to each reaction for MAO-B and MAO-A assay respectively, and the reaction was left for 1 hour at 37° C. in the dark. The oxidative deamination of the substrate was stopped by adding 50 µL (v/v) of NaOH 2N. The conversion of kynuramine to 4-hydroxyquinoline, was monitored by fluorescence (excitation at 320 nm, emission at 360 nm) using a microplate reader (Infinite 200, Tecan). Arbitrary units were used to measure levels of fluorescence produced in the absence and/or in the presence of inhibitor.

The maximum of oxidative deamination activity was obtained by measuring the amount of 4-hydroxyquinoline formed from kynuramine deamination in the absence of inhibitor and corrected for background fluorescence in the absence of MAO enzymes. The Ki of each inhibitor was measure at Vmax/2.

TABLE 1

Summary of Data from MAO-A, MAO-B, and LSD1 Inhibition Studies

| Example No. | MAO A (Ki) | MAO B (Ki) | LSD1 (Ki) |
|---|---|---|---|
| 1 | I | II | IV |
| 2 | II | III | III |
| 3 | I | II | III |
| 4 | I | I | IV |
| 5 | I | I | IV |
| 6 | II | II | IV |
| 7 | I, II | I | IV |
| 8 | II | I | IV |
| 9 | I | II | IV |
| 10 | II | II | IV |
| 11 | II | II | IV |
| 12 | ND | II | IV |
| 13 | II | II | IV |
| 14 | II | II, I II | III |
| 15 | II | II | III |
| 16 | II | II | III |
| 17 | II | II | III |

ND = not determined
The ranges for the Ki value reported in Table 1 are for MAO-A - I = greater than 40 µM and II = between 1 µM and 40 µM; for MAO-B - I = greater than 40 µM, II = between 1 µM and 40 µM, and III = between 0.1 µM and 1 µM; for LSD1 - I = greater than 40 µM, II = between 1 µM and 40 µM, III = between 0.1 µM and 1 µM, and IV between 0.001 µM and 0.1 µM. Example 7 has a MAO-A Ki value of approximately 40 µM.

Most of the compounds of Examples were found to have Ki (IC50) values for MAO-A and MAO-B of greater than 1 µM whereas LSD1 Ki values were in the nanomolar and low nanomolar range many under 100 nanomolar. Trans-2-phenylcyclopropylamine (tranylcypromine) was found to have a Ki for MAO-A of about 2 µM and a Ki of about 0.6 µM for MAO-B and from about 15-35 µM for LSD1 in these assays described herein.

The invention therefore provides inhibitors selective for LSD1. LSD1 selective inhibitors have Ki values for LSD1 which are at least 2-fold lower than the Ki value for MAO-A and/or MAO-B. One example of an LSD1 selective inhibitor is given in e.g., Example 1 and Example 2 which have Ki values for LSD1 which are at least about 10-fold lower than for the Ki values for MAO-A and MAO-B inhibition. Another example of an LSD1 selective inhibitor is in Example 4 which has a Ki value for LSD1 which is more than 100-fold lower than the IC50 for MAO-A and MAO-B.

Other compounds similar to those of the Examples, as illustrated below, that can be synthesized using the synthetic protocols or variations thereof as described herein using the appropriate reagents and starting materials, as readily recognized by the skilled artisan include, but are not limited to:

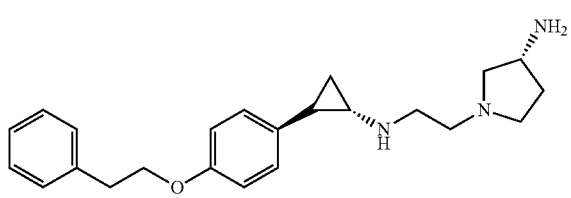

(R)-1-(2-((trans)-2-(4-phenethoxyphenyl)cyclopropylamino)ethyl)pyrrolidin-3-amine

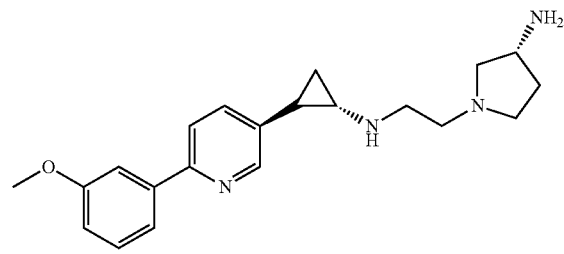

(R)-1-(2-((trans)-2-(6-(3-(trifluoromethyl)phenyl)pyridin-3-yl)cyclopropylamino)ethyl)pyrrolidin-3-amine

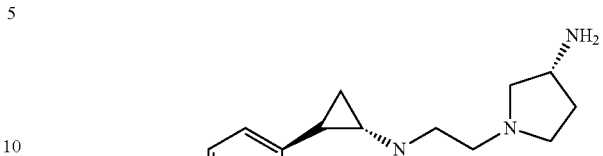

(R)-1-(2-((trans)-2-(6-(3-methoxyphenyl)pyridin-3-yl)cyclopropylamino)ethyl)pyrrolidin-3-amine (R)-1-(2-((trans)-2-(6-(4-chlorophenyl)pyridin-3-yl)cyclopropylamino)ethyl)pyrrolidin-3-amine

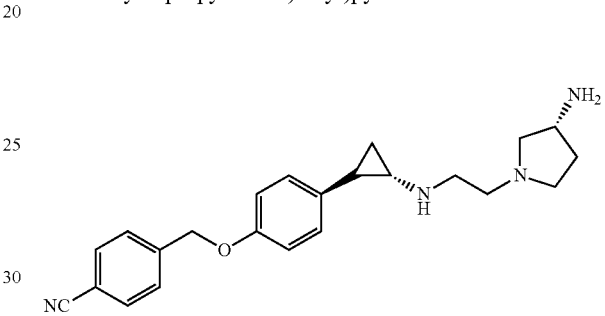

4-((4-((trans)-2-(2-((R)-3-aminopyrrolidin-1-yl)ethylamino)cyclopropyl)phenoxy)methyl)benzonitrile Without being bound by theory, it is believed that these compounds are potent selective inhibitors of LSD1 as described in assays disclosed herein.

Example 40

Cancer Cell Line Study

The human colon cancer cell line HCT116 was obtained from the American Type Culture Collection (ATCC; CCL-247). The HCT116 cell line was maintained in DMEM GlutaMAX (Invitrogen) supplemented with 10% fetal calf serum.

Cells were grown in a humidified incubator at 37 C in 5% $CO_2$.

AlamarBlue Assay

Cells were plated in 96-well plates at a density of 6000 cells/well in 100 μl medium 24 h before addition of drugs. They were then added in concentrations from 100 μM to 0.45 nM (each concentration in triplicate). To do so, a drugs-dilution plate at twice the screening concentrations was prepared. 72 hours later, alamarBlue (Biosource, Invitrogen) viability assay was performed following manufacturer's protocol. In brief, alamarBlue diluted in media was added to cells to have a 5% solution. Cells were incubated at 37 C, 3 hours and at room temperature, 30 min. Cells with no drug and, cells with no drug and lysed with triton X-100 were used as controls. Fluorescence was monitored at 530 nm excitation and 590 nm emission wavelengths. Results were quantified using Infinite F200 Microplate Reader (Tecan Group, Ltd.). EC50 were calculated as the dose of drugs required to inhibit cell growth by 50%, with Origin 7.0 computer program.

The EC50 value (μM) obtained for Example compound no. 10 ((trans)-2-(4-(benzyloxy)phenyl)-N-(2-(4-methylpiperazin-1-yl)ethyl)cyclopropanamine, a compound of Formula (I)) for HCT-116 cells was about 11 μM. Without wishing to be bound by theory, it is the inventor's belief that compounds of Formula I having for (A') an aromatic group (and substituted versions thereof) like, arylalkyl, aryl, and arylalkoxy (and substituted versions thereof) have excellent cell penetration and activity. These types of groups can be meta or para to the cyclopropyl ring of the compounds of Formula I and preferably are para.

Previous reports of LSD1 have found that it is involved in cell proliferation and growth. Some studies have implicated LSD1 as a therapeutic target for cancer. Huang et al. (2007) *PNAS* 104:8023-8028 found that polyamines inhibitors of LSD1 modestly cause the reexpression of genes aberrantly silenced in cancer cells and particularly colorectal cancer (Huang et al. *Clin Cancer Res*. (2009) December 1; 15(23): 7217-28. Epub 2009 Nov. 24. PMID: 19934284). Scoumanne et al. ((2007) *J. Biol. Chem*. May 25; 282(21):15471-5) found that deficiency in LSD1 leads to a partial cell cycle arrest in G2/M and sensitizes cells to growth suppression induced by DNA damage. Kahl et al. ((2006) *Cancer Res*. 66(23):11341-7) found that LSD1 expression is correlated with prostate cancer aggressiveness. Metzger et al. reported that LSD1 modulation by siRNA and pargyline regulates androgen receptor (AR) and may have therapeutic potential in cancers where AR plays a role, like prostate, testis, and brain cancers. Lee et al. ((2006) *Chem. Biol*. 13:563-567) reported that tranylcypromine derepresses Egr-1 gene expression in some cancer lines. A body of evidence is accumulating that Egr-1 is a tumor suppressor gene in many contexts (see e.g., Calogero et al. (2004) *Cancer Cell International* 4:1 exogenous expression of EGR-1 resulted in growth arrest and eventual cell death in primary cancer cell lines; Lucerna et al. (2006) *Cancer Research* 66, 6708-6713 show that sustained expression of Egr-1 causes antiangiogeneic effects and inhibits tumor growth in some models; Ferraro et al. ((2005) *J. Clin. Oncol*. March 20; 23(9):1921-6) reported that Egr-1 is downregulated in lung cancer patients with a higher risk of recurrence and may be more resistant to therapy. Thus, increasing Egr-1 expression via inhibition of LSD1 is a therapeutic approach for some cancers. Recent studies have also implicated LSD1 in brain cancer (Schulte et al. (2009) Cancer Res. March 1; 69(5):2065-71). Other studies have implicated LSD1 in breast cancer (Lims et al. Carcinogenesis. 2009 Dec. 30. [Epub ahead of print] PMID: 20042638).

Thus, a body of evidence has implicated LSD1 in a number of cancers, which suggests that LSD1 is a therapeutic target for cancer. The instant inventors have discovered a class of LSD1 inhibitors that can be used to treat diseases where LSD1 is implicated as a therapeutic target like cancer. Accordingly, the phenylcyclopropylamine compounds of the invention can be used to treat such diseases, like colorectal cancer, brain cancer, breast cancer, lung cancer, and prostate cancer.

Previous studies reported in the literature indicated that substitutions on the amine group of phenylcyclopropylamines reduced the ability of the compound to inhibit amine oxidases, which have significant structural homology to LSD1. For example, Zirkie et al. ((1962) *J. Med. Chem*. 1265-1284) found that a methyl substituent on the amine group decreased activity slightly whereas substitution with larger alkyl groups and groups bearing ring system like aralkyls reduced MAO activity substantially. The inventors of the instant invention have unexpectedly found that a variety of substitutions on the amine group of phenylcyclopropyl amine produce potent LSD1 inhibitors. Furthermore, compounds of Formula I with substituents in the para-position on the phenyl ring of the phenylcyclopropylamino core having an aromatic group result in highly active and selective compounds. The results of the instant invention show that further modifications to the phenylpropylamine core as described herein can result in potent LSD1 inhibitors. The Examples show compounds which selectively inhibit LSD1 compared to MAO-A and MAO-B. Thus, the inventors have identified a new class of phenylcyclopropylamine containing LSD1 inhibitors with unexpected potency and selectivity for LSD1, a biologically relevant target in oncology.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. The mere mentioning of the publications and patent applications does not necessarily constitute an admission that they are prior art to the instant application.

Although the foregoing invention has been described in some detail by way of illustration and example for purposes of clarity of understanding, it will be obvious that certain changes and modifications may be practiced within the scope of the appended claims.

The invention claimed is:

1. A compound of Formula I:

$$(A')_x\text{-}(A)\text{-}(B)\text{-}(Z)\text{-}(L)\text{-}(D) \qquad I$$

wherein:
(A) is heteroaryl or aryl;
each (A'), if present, is independently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, 2, or 3 substituents independently chosen from halo, haloalkyl, aryl, arylalkoxy, alkyl, alkoxy, cyano, sulfonyl, amido, and sulfinyl;
X is 0, 1, 2, or 3;
(B) is a cyclopropyl ring, wherein (A) and (Z) are covalently bonded to different carbon atoms of (B);
(Z) is —NH—;
(L) is chosen from —$CH_2CH_2$—, —$CH_2CH_2CH_2$—, and —$CH_2CH_2CH_2CH_2$—; and
(D) is chosen from —N(—R1)-R2, —O—R3, and —S—R3 wherein:
R1 and R2 are mutually linked to form a heterocyclic ring together with the nitrogen atom that R1 and R2 are attached to, wherein said heterocyclic ring has 0, 1, 2, or 3 substituents independently chosen from $NH_2$, —NH($C_1$-$C_6$ alkyl), —N($C_1$-$C_6$ alkyl)($C_1$-$C_6$ alkyl), alkyl, halo, cyano, alkoxy, haloalkyl, and haloalkoxy, or
R1 and R2 are independently chosen from —H, alkyl, $C_{3-7}$cycloalkyl, haloalkyl, and heterocyclyl, wherein the sum of substituents on R1 and R2 together is 0, 1, 2, or 3, and the substituents are independently chosen from —$NH_2$, —NH($C_1$-$C_6$ alkyl), —N($C_1$-$C_6$ alkyl)($C_1$-$C_6$ alkyl), and fluoro; and
R3 is chosen from —H, alkyl, cycloakyl, haloalkyl, and heterocyclyl, wherein R3 has 0, 1, 2, or 3 substituents independently chosen from —$NH_2$, —NH($C_1$-$C_6$ alkyl), —N($C_1$-$C_6$ alkyl)($C_1$-$C_6$ alkyl), and fluoro;

or an enantiomer, diastereomer, or mixture thereof, or a pharmaceutically acceptable salt thereof;

with the proviso that the following compounds are excluded:

N1-[(trans)-2-phenylcyclopropyl]-N2-undecyl-rel-1,2-ethanediamine;

N1,N1-dimethyl-N2-(2-phenylcyclopropyl)-1,3-propanediamine;

N1,N1-dimethyl-N2-(2-phenylcyclopropyl)-1,2-ethanediamine; and trans-1-phenyl-2-[(2-hydroxyethyl)amino]cyclopropane.

2. The compound of claim 1 or a pharmaceutically acceptable salt thereof, wherein (A) is aryl.

3. The compound of claim 1 or a pharmaceutically acceptable salt or thereof, wherein (A) is phenyl.

4. The compound of claim 1 or a pharmaceutically acceptable salt thereof, wherein X is 1 or 2.

5. The compound of claim 1 or a pharmaceutically acceptable salt thereof, wherein X is 1 and (A') is chosen from aryl and arylalkoxy, wherein said aryl or said arylalkoxy has 0 or 1 substituent chosen from halo and haloalkyl.

6. The compound of claim 5 or a pharmaceutically acceptable salt thereof, wherein (A') is chosen from phenyl, benzyloxy, and phenethyloxy, wherein said phenyl, said benzyloxy, or said phenethyloxy has 0 or 1 substituent chosen from halo and haloalkyl.

7. The compound of claim 5 or a pharmaceutically acceptable salt thereof, wherein the (A') group is in the para position with respect to the cyclopropyl ring (B).

8. The compound of claim 1 or a pharmaceutically acceptable salt thereof, wherein (D) is —N(—R1)-R2, and further wherein R1 and R2 are mutually linked to form a heterocyclic ring together with the nitrogen atom that R1 and R2 are attached to, wherein said heterocyclic ring has 0, 1, 2, or 3 substituents independently chosen from —NH$_2$, —NH(C$_1$-C$_6$ alkyl), —N(C$_1$-C$_6$ alkyl)(C$_1$-C$_6$ alkyl), alkyl, halo, cyano, alkoxy, haloalkyl, and haloalkoxy.

9. The compound of claim 8 or a pharmaceutically acceptable salt thereof, wherein said heterocyclic ring is a 4, 5, or 6 membered heterocyclic ring which is saturated.

10. The compound of claim 8 or a pharmaceutically acceptable salt thereof, wherein said heterocyclic ring is chosen from azetidinyl, pyrrolidinyl, piperidinyl, and morpholino.

11. The compound of claim 8 or a pharmaceutically acceptable salt thereof, wherein said heterocyclic ring has 0 or 1 substituent chosen from —NH$_2$, —N(C$_1$-C$_6$ alkyl)(C$_1$-C$_6$ alkyl), and alkyl.

12. The compound of claim 1 or a pharmaceutically acceptable salt thereof, wherein (D) is —N(—R1)-R2, and further wherein R1 and R2 are independently chosen from —H, alkyl, C$_{3-7}$ cycloalkyl, and haloalkyl, wherein the sum of substituents on R1 and R2 together is 0, 1, 2, or 3, and the substituents are independently chosen from —NH$_2$, —NH(C$_1$-C$_6$ alkyl), —N(C$_1$-C$_6$ alkyl)(C$_1$-C$_6$ alkyl), and fluoro.

13. The compound of claim 1 or a pharmaceutically acceptable salt thereof, wherein (D) is chosen from —O—R3 and —S—R3, and further wherein R3 is chosen from alkyl, cycloalkyl, and haloalkyl, wherein R3 has 0, 1, 2, or 3 substituents independently chosen from —NH$_2$, —NH(C$_1$-C$_6$ alkyl), —N(C$_1$-C$_6$ alkyl)(C$_1$-C$_6$ alkyl), and fluoro.

14. The compound of claim 1 or a pharmaceutically acceptable salt thereof, wherein (A) is heteroaryl.

15. The compound of claim 1 or a pharmaceutically acceptable salt thereof, wherein (A) is a heteroaryl chosen from pyridyl, pyrimidinyl, and thiophenyl.

16. The compound of claim 1 or a pharmaceutically acceptable salt thereof, wherein (L) is —CH$_2$CH$_2$—.

17. The compound of claim 1 or a pharmaceutically acceptable salt thereof, wherein (A) and (Z) are in the trans orientation with respect to the cyclopropyl ring (B).

18. The compound of claim 1 wherein said compound is chosen from:

N1-((trans)-2-(4-(3-bromobenzyloxy)phenyl)cyclopropyl)-N2-cyclopropylethane-1,2-diamine;

N1-((trans)-2-(3'-chlorobiphenyl-4-yl)cyclopropyl)-N2-cyclopropylethane-1,2-diamine;

N1-cyclopropyl-N2-((trans)-2-(4-phenethoxyphenyl)cyclopropyl)ethane-1,2-diamine;

N1,N1-diethyl-N2-((trans)-2-(4-(3-fluorobenzyloxy)phenyl)cyclopropyl)ethane-1,2-diamine;

(trans)-2-(4-bromophenyl)-N-(2-(4-methylpiperazin-1-yl)ethyl)cyclopropanamine;

N1-((trans)-2-(terphenyl-4-yl)cyclopropyl)-N2-cyclopropylethane-1,2-diamine;

(trans)-N-(2-(piperidin-1-yl)ethyl)-2-(3'-(trifluoromethyl)biphenyl-4-yl)cyclopropanamine;

N1,N1-diethyl-N2-((trans)-2-(3'-(trifluoromethyl)biphenyl-4-yl)cyclopropyl)ethane-1,2-diamine;

(trans)-N-(2-(piperazin-1-yl)ethyl)-2-(3'-(trifluoromethyl)biphenyl-4-yl)cyclopropanamine;

(S)-1-(2-((trans)-2-(3'-(trifluoromethyl)biphenyl-4-yl)cyclopropylamino)ethyl)pyrrolidin-3-amine;

(R)-1-(2-((trans)-2-(3'-chlorobiphenyl-4-yl)cyclopropylamino)ethyl)pyrrolidin-3-amine;

(R)-1-(2-((trans)-2-(4'-chlorobiphenyl-4-yl)cyclopropylamino)ethyl)pyrrolidin-3-amine;

(R)-1-(2-((trans)-2-(3'-methoxybiphenyl-4-yl)cyclopropylamino)ethyl)pyrrolidin-3-amine;

(R)-1-(2-((trans)-2-(4-(3-bromobenzyloxy)phenyl)cyclopropylamino)ethyl)pyrrolidin-3-amine; and (R)-1-(2-((trans)-2-(6-(3-(trifluoromethyl)phenyl)pyridin-3-yl)cyclopropylamino)ethyl)pyrrolidin-3-amine;

or pharmaceutically acceptable salt thereof.

19. A pharmaceutical composition comprising the compound of claim 1 or a pharmaceutically acceptable salt thereof and a pharmaceutically acceptable carrier.

20. A method of treating an LSD1-mediated disease or condition comprising administering, to a subject in need of treatment, a therapeutically effective amount of the compound of claim 1 or a pharmaceutically acceptable salt thereof.

21. A method of treating cancer comprising administering, to a subject in need of treatment, a therapeutically effective amount of the compound of claim 1 or a pharmaceutically acceptable salt thereof, wherein the cancer is selected from the group consisting of colorectal cancer, breast cancer, lung cancer and prostate cancer.

22. The method of claim 21, whereby said compound or said pharmaceutically acceptable salt thereof is to be administered in combination with an anti-proliferative drug, an anticancer drug, a cytostatic drug, a cytotoxic drug and/or radiotherapy.

23. The method of claim 20, wherein said subject is a human.

* * * * *